(12) United States Patent
Zhu et al.

(10) Patent No.: US 11,076,597 B2
(45) Date of Patent: Aug. 3, 2021

(54) HIGH STRESS RESISTANT PLANT GROWTH REGULATOR AND PREPARATION METHOD AND USE THEREOF

(71) Applicant: SHANGHAI INSTITUTES FOR BIOLOGICAL SCIENCES, CHINESE ACADEMY OF SCIENCES, Shanghai (CN)

(72) Inventors: Jiankang Zhu, Shanghai (CN); Yulu Zhang, Shanghai (CN); Minjie Cao, Shanghai (CN); Xue Liu, Shanghai (CN); Qiuhua Wang, Shanghai (CN)

(73) Assignee: CAS CENTER FOR EXCELLENCE IN MOLECULAR PLANT SCIENCES, Shanghai (CN)

( * ) Notice: Subject to any disclaimer, the term of this patent is extended or adjusted under 35 U.S.C. 154(b) by 254 days.

(21) Appl. No.: 16/066,755

(22) PCT Filed: Nov. 18, 2016

(86) PCT No.: PCT/CN2016/107516
§ 371 (c)(1),
(2) Date: Jun. 28, 2018

(87) PCT Pub. No.: WO2017/114052
PCT Pub. Date: Jul. 6, 2017

(65) Prior Publication Data
US 2019/0000084 A1  Jan. 3, 2019

(30) Foreign Application Priority Data

Dec. 28, 2015 (CN) .......................... 201511004527.2
May 16, 2016 (CN) .......................... 201610325811.8

(51) Int. Cl.
*A01N 43/86* (2006.01)
*C07D 263/58* (2006.01)
*C07D 215/38* (2006.01)
*A01N 43/42* (2006.01)
*C07D 239/80* (2006.01)
*A01N 43/54* (2006.01)
*C07D 215/227* (2006.01)
*C07D 265/18* (2006.01)

(52) U.S. Cl.
CPC ............. *A01N 43/86* (2013.01); *A01N 43/42* (2013.01); *A01N 43/54* (2013.01); *C07D 215/227* (2013.01); *C07D 215/38* (2013.01); *C07D 239/80* (2013.01); *C07D 263/58* (2013.01); *C07D 265/18* (2013.01); *C07B 2200/07* (2013.01)

(58) Field of Classification Search
None
See application file for complete search history.

(56) References Cited

FOREIGN PATENT DOCUMENTS

| WO | WO2014210555 | 12/2014 | |
|---|---|---|---|
| WO | WO2015155154 | 10/2015 | |
| WO | WO2016022915 | 2/2016 | |
| WO | WO-2018017490 A1 * | 1/2018 | ........... C07D 265/18 |

OTHER PUBLICATIONS

Cambridge Medchem Consulting "Bioisosteric Replacements" https://web.archive.org/web/20130113020012/https://www.cambridgemedchemconsulting.com/resources/bioisoteres/, cached wayback machine Jan. 13, 2013, no pagination (Year: 2013).*

* cited by examiner

*Primary Examiner* — Erin E Hirt
(74) *Attorney, Agent, or Firm* — Adam Warwick Bell; Matthew Rupert Kaser

(57) ABSTRACT

Disclosed are a high stress resistant plant growth regulator and a preparation and use thereof. In particular, the compound provided by the present invention is an ABA substitute for significantly improving the stress resistance of plants, and therefore has a very wide application prospect.

7 Claims, 17 Drawing Sheets

HIGH STRESS RESISTANT PLANT GROWTH REGULATOR AND PREPARATION METHOD AND USE THEREOF

TECHNICAL FIELD

The present invention relates to the field of botany, in particular to high stress resistant plant growth regulator and preparation and use thereof.

BACKGROUND ART

Abscisic Acid (ABA) is a key factor that balances plant endogenous hormones and metabolism of related growth-active substances, which has the ability to promote plants to absorb water and fertilizer in balance and coordinate metabolism in vivo, can effectively regulate the root/crown of the plants, and vegetative growth and reproductive growth in plants, and plays an important role in improving the quality and the yield of crops. Through the application of ABA, there is an important physiological activity effect and application value in improving the quality of agricultural products and many other aspects. In addition, exogenous ABA can cause rapid closure of leaf stomatal and transpiration inhibition, which can be used for the preservation of flower, or preventing wilting during the transportational process of crop seedling transplanting cultivation. ABA can also control flower bud differentiation, regulate flowering phase, which possesses a great application value in the aspects of flower and gardening.

ABA can improve the crop growth in the low temperature, drought, spring chilling, salt and other undesirable growth environments. Therefore, ABA is widely used in a lawn, farmland and garden, especially in the water-deficient areas, such as the western region, which is of great significance to the development of China's agricultural industry.

However, natural active (+)-ABA is unstable and difficult to be synthesized which results in a high production cost. Therefore, ABA has not been widely used for agricultural production, while scientists from all over the world are developing alternatives to natural ABA.

So far although some alternatives to ABA have been developed, the activity of these alternatives is unsatisfactory, whose application value in agricultural production is low. In addition, some alternatives have less environmentally friendliness.

Therefore, there is an urgent need in the art to develop compounds which are environmentally friendly and can effectively increase the plant stress resistance.

SUMMARY OF THE INVENTION

The object of the present invention is to provide compounds, which are environmentally friendly and can effectively increase the plant stress resistance and the preparation and uses thereof.

In the first aspect of the present invention, a compound represented by formula (I), or a salt, or an optical isomer or a raceme, or a solvate, or a precursor thereof is provided,

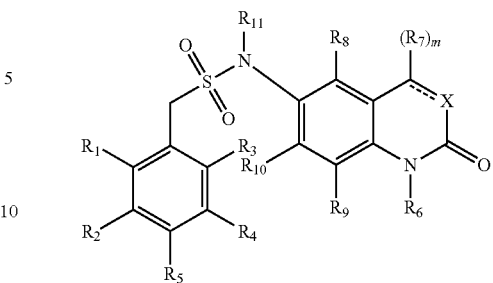

wherein,
$R_1$ is H, halogen, $C_1$-$C_3$ alkyl, or $C_1$-$C_3$ haloalkyl;
$R_2$ is H, halogen, $C_1$-$C_3$ alkyl, or $C_1$-$C_3$ haloalkyl;
$R_3$ is H, halogen, $C_1$-$C_3$ alkyl, or $C_1$-$C_3$ haloalkyl;
$R_4$ is H, halogen, $C_1$-$C_3$ alkyl, or $C_1$-$C_3$ haloalkyl;
$R_5$ is halogen, $C_1$-$C_3$ alkyl, $C_1$-$C_3$ haloalkyl, $SF_5$ or $C_3$-$C_8$ cycloalkyl;
$R_6$ is substituted or unsubstituted $C_1$-$C_7$ alkyl, substituted or unsubstituted $C_2$-$C_7$ alkenyl, substituted or unsubstituted $C_2$-$C_7$ alkynyl, substituted or unsubstituted $C_3$-$C_7$ cycloalkyl, or substituted or unsubstituted —$R_a$—O—$R_b$, wherein $R_a$ is $C_1$-$C_2$ alkylene and $R_b$ is H, $C_1$-$C_3$ alkyl; and the "substituted" means substituted with one or more substituents selected from the group consisting of: halogen, —$OR_b$, —CN, —$N(R_b)_2$, and nitro;
$R_7$ is selected from the group consisting of: H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_5$-$C_{10}$ heterocyclyl, $R_c$—C(O)—, —$OR_b$, —CN, and —$N(R_b)_2$; $R_c$ is selected from the group consisting of: hydroxyl, mercapto, substituted or unsubstituted $C_1$-$C_6$ alkyl, substituted or unsubstituted $C_1$-$C_6$ alkoxy; wherein the heterocyclyl contains 1 to 2 heteroatoms selected from N, O, S, and the "substituted" means substituted with one or more substituents selected from the group consisting of: halogen, —$OR_b$, —CN, —$N(R_b)_2$, and nitro;
$R_8$, $R_9$, $R_{10}$ are each independently selected from the group consisting of:
(i) H;
(ii) substituted or unsubstituted $C_1$-$C_6$ alkyl, $C_3$-$C_8$ alkoxy, substituted or unsubstituted $C_3$-$C_8$ cycloalkyl, halogen, $R_c$—C(O)—, —OH, —$NH_2$; $R_{11}$ is selected from the group consisting of: hydroxyl, mercapto, substituted or unsubstituted $C_1$-$C_6$ alkyl, substituted or unsubstituted $C_1$-$C_6$ alkoxy; wherein the "substituted" means substituted with one or more substituents selected from the group consisting of: halogen, —$OR_b$, —CN, —$N(R_b)_2$, and nitro;
$R_{11}$ is H, $C_1$-$C_3$ alkyl, or $C_1$-$C_3$ haloalkyl;
X is $CR_{12}$, $NR_{13}$, O, or S, wherein $R_{12}$ is selected from the group consisting of: H, halogen, $C_1$-$C_3$ alkyl, $C_2$-$C_3$ alkenyl, $C_2$-$C_3$ alkynyl, $C_1$-$C_3$ haloalkyl, and a combination thereof;
$R_{13}$ is none or selected from the group consisting of: H, halogen, $C_1$-$C_3$ alkyl, $C_2$-$C_3$ alkenyl, $C_2$-$C_3$ alkynyl, $C_1$-$C_3$ haloalkyl, and a combination thereof;
m=1 or 2;
" ===== " represents a single bond or a double bond; provided that, when X is $CR_{12}$, " ===== " is a double bond.

In another preferred embodiment, $R_6$ is $C_1$-$C_7$ alkyl, $C_2$-$C_7$ alkenyl, $C_2$-$C_7$ alkynyl, $C_3$-$C_7$ cycloalkyl, or —$R_a$—O—$R_b$, wherein $R_a$ is $C_1$-$C_2$ alkylene and $R_b$ is H, $C_1$-$C_3$ alkyl.

In another preferred embodiment, $R_7$ is selected from the group consisting of: substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_5$-$C_{10}$ heterocyclyl, $R_c$—C(O)—, —$OR_b$, —CN, and —$N(R_b)_2$; $R_c$ is selected from the group consisting of: hydroxyl, mercapto, substituted or unsubstituted $C_1$-$C_6$ alkyl, substituted or unsubstituted $C_1$-$C_6$ alkoxy; wherein the heterocyclyl contains 1 to 2 heteroatoms selected from N, O, S, and the "substituted" means substituted with one or more substituents selected from the group consisting of: halogen, —$OR_b$, —CN, —$N(R_b)_2$, and nitro.

In another preferred embodiment, when X is $CR_{12}$ and $R_{12}$ is H, " ===== " is a double bond.

In another preferred embodiment, $R_7$ is H.

In another preferred embodiment, when X is $CR_{12}$, $R_8$, $R_9$, $R_{10}$ are not H at the same time.

In another preferred embodiment, when X is $CR_{12}$, $R_8$, $R_9$, $R_{10}$ are H at the same time.

In another preferred embodiment, when $R_{13}$ is none, " ===== " is a double bond and m=1.

In another preferred embodiment, when $R_{13}$ is selected from the group consisting of: H, halogen, $C_1$-$C_3$ alkyl, $C_2$-$C_3$ alkenyl, $C_2$-$C_3$ alkynyl, $C_1$-$C_3$ haloalkyl, and a combination thereof, " ===== " is a single bond and m=1 or 2.

In another preferred embodiment, when X is O or S, " ===== " is a single bond.

In another preferred embodiment, the halogen comprises F, Cl, Br or I.

In another preferred embodiment, the halogen is F.

In another preferred embodiment, the compound has a structure of formula Ia:

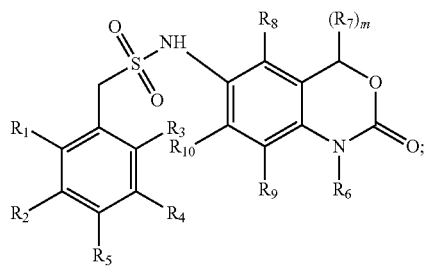

Ia wherein the definitions of $R_1$-$R_{10}$, and m are described as above.

In another preferred embodiment, the compound has a structure of formula Ib:

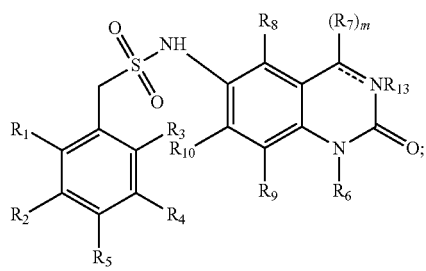

Ib wherein the definitions of $R_1$-$R_{10}$, $R_{13}$, m, and " ===== " are described as above.

In another preferred embodiment, the compound has a structure of formula Ic:

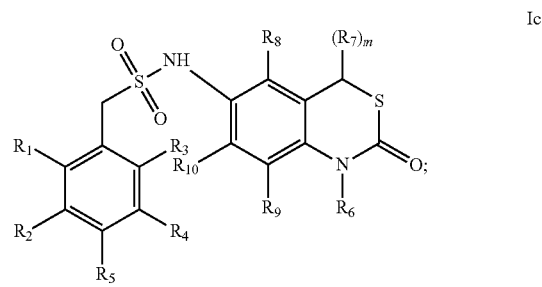

Ic wherein the definitions of $R_1$-$R_{10}$, and m are described as above.

In another preferred embodiment, the compound has a structure of formula Id:

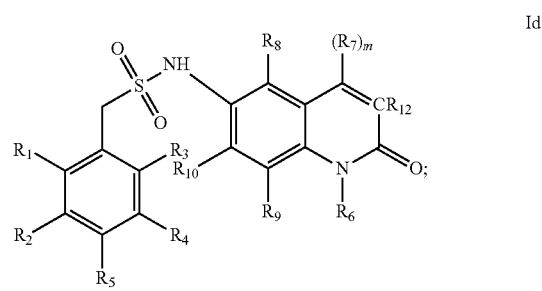

Id wherein the definitions of $R_1$-$R_{10}$, $R_{12}$, and m are described as above.

In another preferred embodiment, all of $R_1$, $R_2$, $R_3$, and $R_4$ are H.

In another preferred embodiment, 1, 2, 3, or 4 of $R_1$, $R_2$, $R_3$, and $R_4$ are halogen.

In another preferred embodiment, the halogen comprises F, Cl, Br or I.

In another preferred embodiment, the halogen is F.

In another preferred embodiment, 4 of $R_1$, $R_2$, $R_3$, and $R_4$ are F.

In another preferred embodiment, $R_5$ is $C_1$-$C_3$ alkyl, $C_1$-$C_3$ haloalkyl, $SF_5$ or $C_3$-$C_6$ cycloalkyl.

In another preferred embodiment, $R_5$ is methyl or cyclopropyl.

In another preferred embodiment, $R_6$ is substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_5$ cycloalkyl, or substituted or unsubstituted wherein $R_a$ is $C_1$-$C_2$ alkylene and $R_b$ is H, or $C_1$-$C_3$ alkyl; and the "substituted" means substituted with one or more substituents selected from the group consisting of: halogen, —$OR_b$, —CN, —$N(R_b)_2$, or nitro.

In another preferred embodiment, $R_6$ is n-propyl, ethyl, isopropyl, isobutyl, or fluoro n-propyl.

In another preferred embodiment, $R_6$ is $C_3$ alkyl, $C_3$ alkenyl, or $C_3$ alkynyl.

In another preferred embodiment, $R_6$ is n-propyl.

In another preferred embodiment, $R_7$ is selected from the group consisting of: H, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $C_3$-$C_6$ cycloalkyl, substituted or unsubstituted $C_5$-$C_8$ heterocyclyl, $R_c$—C(O)—, —OH, —CN, and —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the heterocyclyl contains 1 to 2 heteroatoms selected from N, O, S, and the "substituted" means substituted with one or more substituents selected from the group consisting of: halogen, —OH, —CN, —NH$_2$, and nitro; and $R_8$, $R_9$, $R_{10}$ are each independently selected from the group consisting of:
(i) H;
(ii) substituted or unsubstituted $C_1$-$C_4$ alkyl, $C_3$-$C_6$ alkoxy, halogen, $R_c$—C(O)—, —OH, —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the "substituted" means substituted with one or more substituents selected from the group consisting of: halogen, —OH, —CN, —NH$_2$, and nitro.

In another preferred embodiment, $R_7$ is selected from the group consisting of: H, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $C_3$-$C_6$ cycloalkyl, substituted or unsubstituted $C_5$-$C_8$ heterocyclyl, $R_c$—C(O)—, —OH, —CN, and —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the heterocyclyl contains 1 heteroatom selected from N, O, S, and the "substituted" means substituted with one or more substituents selected from the group consisting of: halogen, —OH, —CN, —NH$_2$, and nitro; and $R_8$, $R_9$, $R_{10}$ are each independently selected from the group consisting of:
(i) H;
(ii) substituted or unsubstituted $C_1$-$C_4$ alkyl, $C_3$-$C_6$ alkoxy, halogen, $R_c$—C(O)—, —OH, —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the "substituted" means substituted with one or more substituents selected from the group consisting of: halogen, —OH, —CN, —NH$_2$, and nitro.

In another preferred embodiment, $R_7$ is selected from the group consisting of: substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $C_3$-$C_6$ cycloalkyl, substituted or unsubstituted $C_5$-$C_8$ heterocyclyl, $R_c$—C(O)—, —OH, —CN, and —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the heterocyclyl contains 1 to 2 heteroatoms selected from N, O, S, and the "substituted" means substituted with one or more substituents selected from the group consisting of: halogen, —OH, —CN, —NH$_2$, and nitro.

In another preferred embodiment, $R_7$ is selected from the group consisting of: substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $C_3$-$C_6$ cycloalkyl, substituted or unsubstituted $C_5$-$C_8$ heterocyclyl, $R_c$—C(O)—, —OH, —CN, and —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the heterocyclyl contains 1 heteroatom selected from N, O, S, and the "substituted" means substituted with one or more substituents selected from the group consisting of: halogen, —OH, —CN, —NH$_2$, and nitro; and $R_8$, $R_9$, $R_{10}$ are each independently selected from the group consisting of:
(i) H;
(ii) substituted or unsubstituted $C_1$-$C_4$ alkyl, $C_3$-$C_6$ alkoxy, halogen, $R_c$—C(O)—, —OH, —NH$_2$; $R_c$ is selected from the group consisting of: hydroxyl, mercapto, substituted or unsubstituted $C_1$-$C_4$ alkyl, substituted or unsubstituted $C_1$-$C_4$ alkoxy; wherein the "substituted" means substituted with one or more substituents selected from the group consisting of: halogen, —OH, —CN, —NH$_2$, and nitro.

In another preferred embodiment, $R_7$, $R_8$, $R_9$, and $R_{10}$ are the specific groups corresponding to each specific compound in the Examples of this application.

In another preferred embodiment, the compound is selected from the group consisting of:

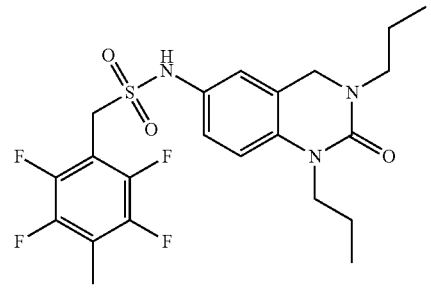

NC3F4

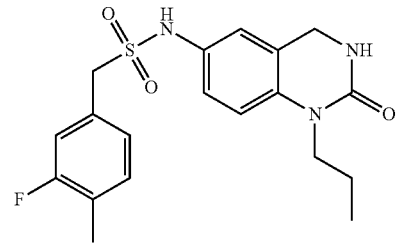

NC0FD1

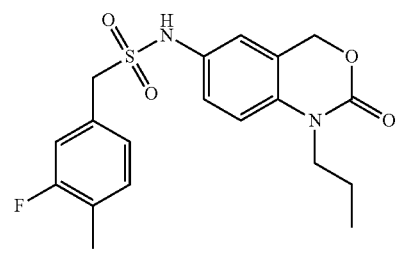

OFD1

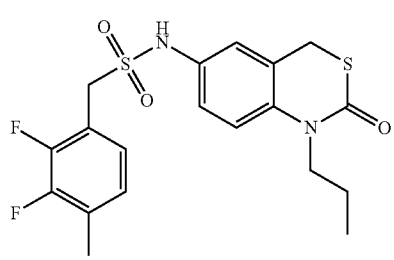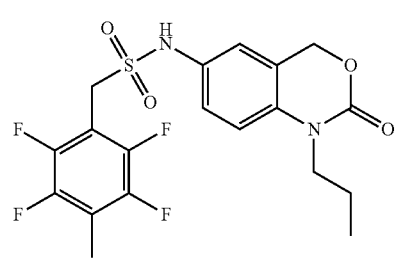

-continued
SF0
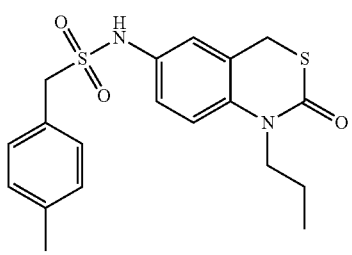
NC0FU1
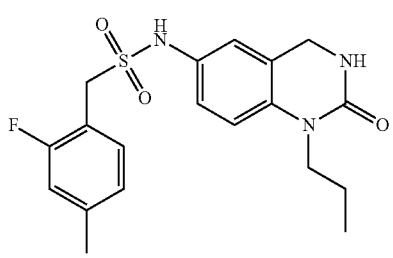
OFD2
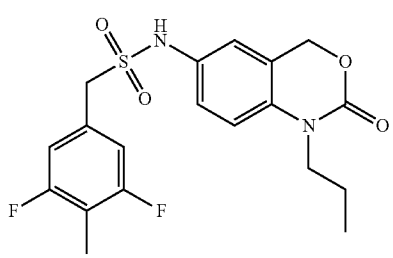
SFD2
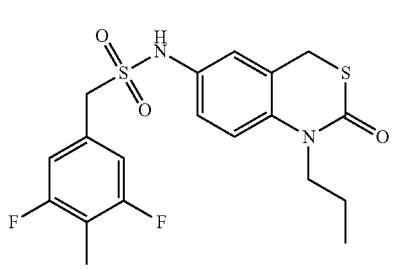
1022B
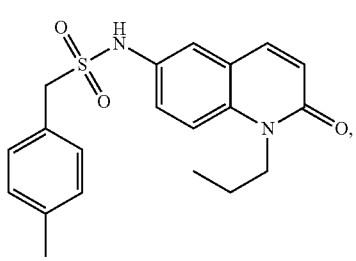
NDFUF1
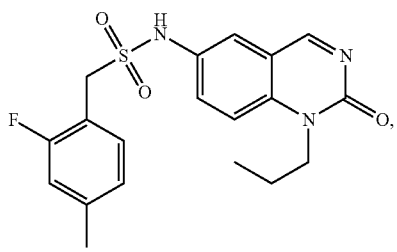
-continued
NDFDF1
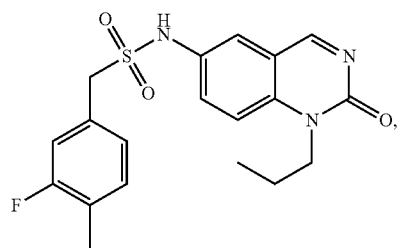
NDF0
NDF4
NDFD2
NDFS2
1-3
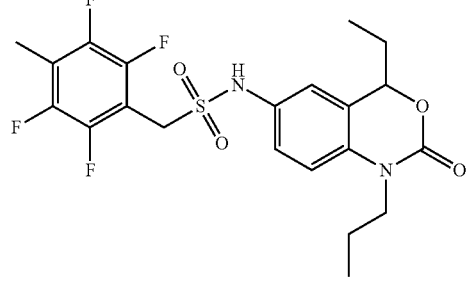

1-4
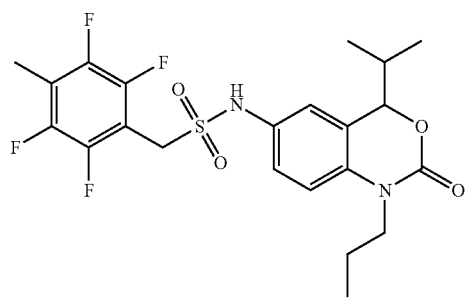
1-5
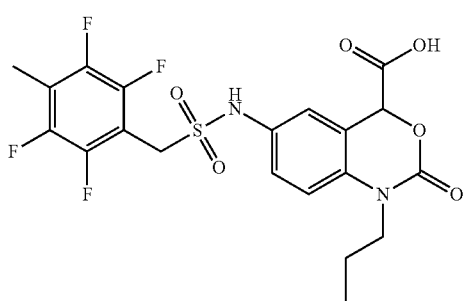
1-6
2-1
2-2
2-3
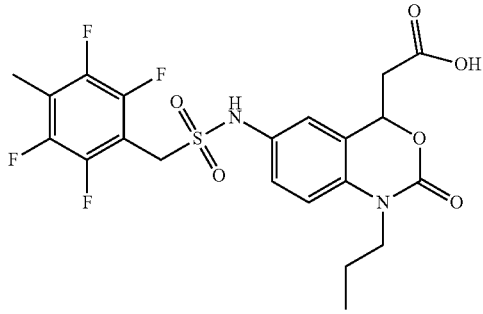
2-4
3-1
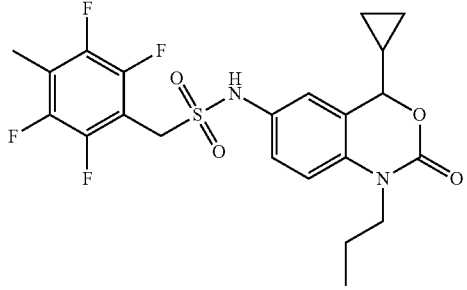
3-2
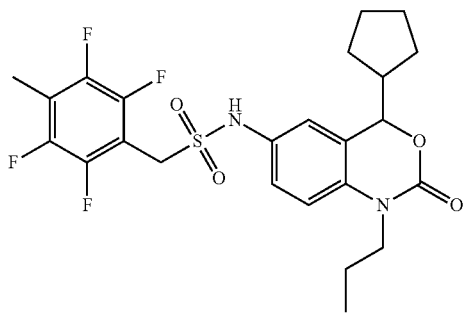
3-3
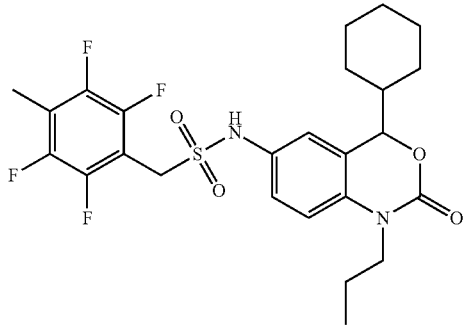

3-4
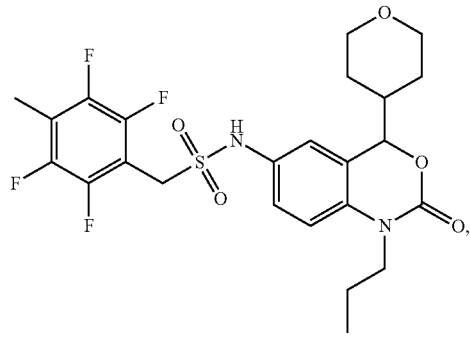
4-OH
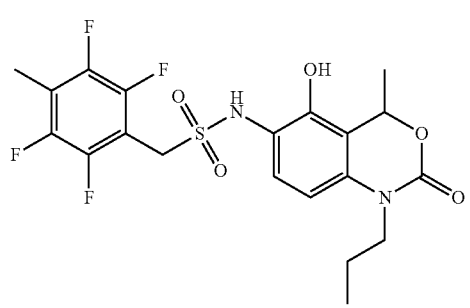
4-F
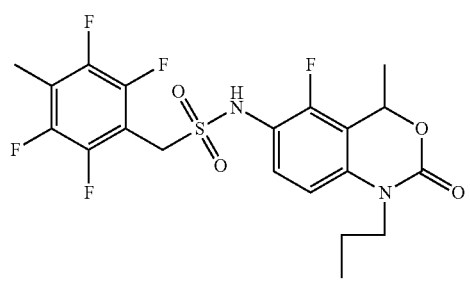
4-NH2
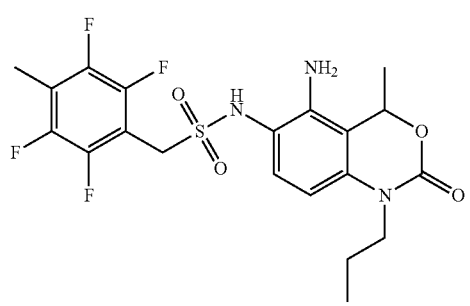
4-CH3
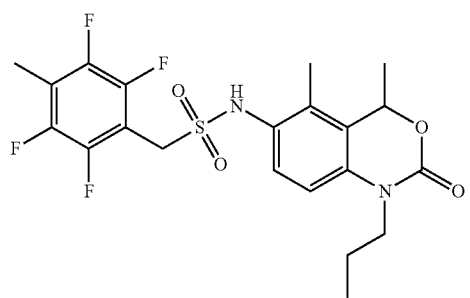
4-COOH
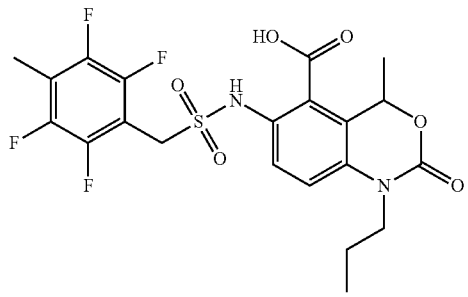
4-CH2OH
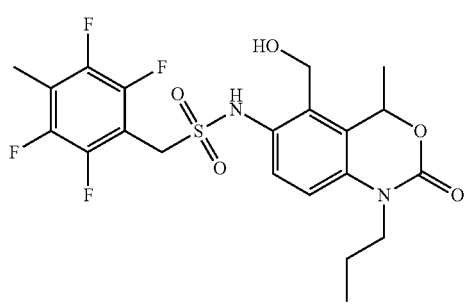
5-OH
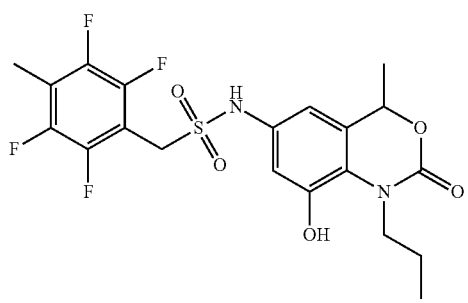
5-CH3
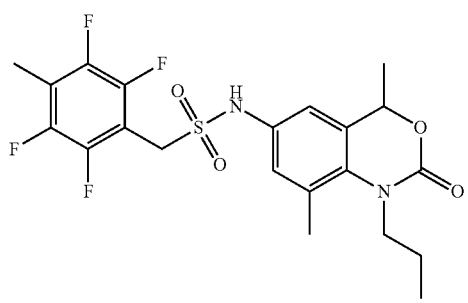
5-NH2
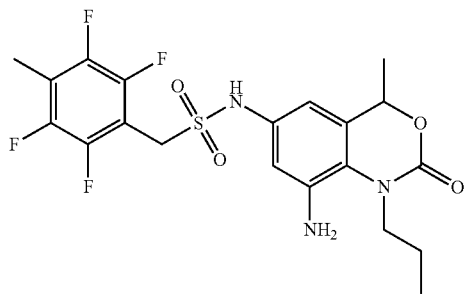

5-F

5-COOH

5-CH2OH

6-ALLF

7-CF3

7-CF3

8-Tri-H

8-Tri-F

8-Tri-Fd

8-Tris-2F

-continued
8-Tris-2Fd
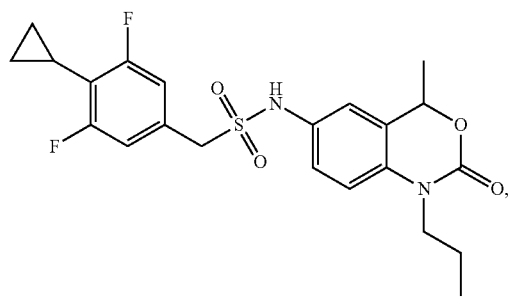
0224
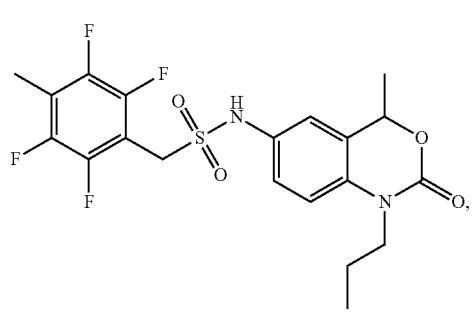
0304
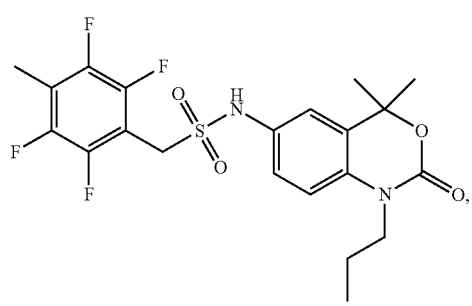
0706
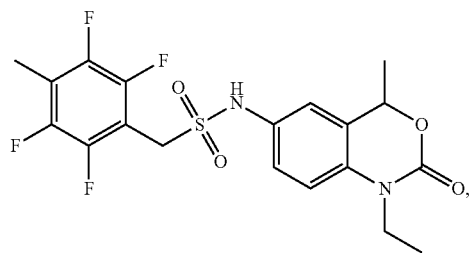
0708
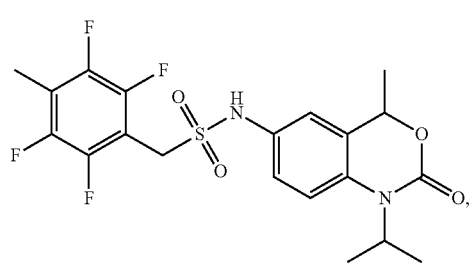
-continued
0713
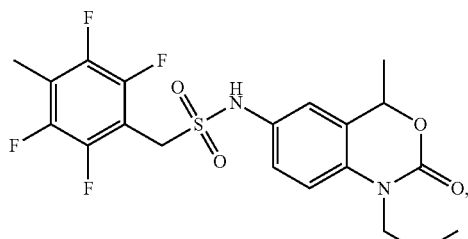
0715
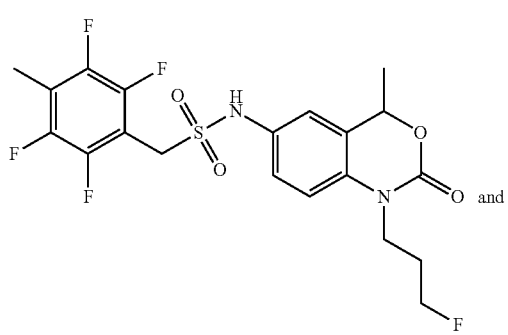
and
1028c
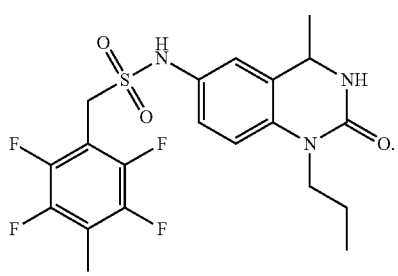
In another preferred embodiment, the compound is selected from the group consisting of:
0224
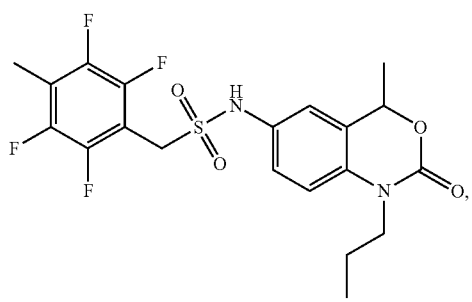
0304
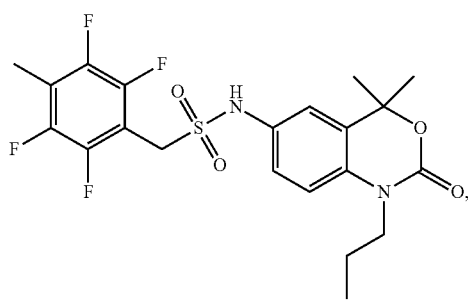

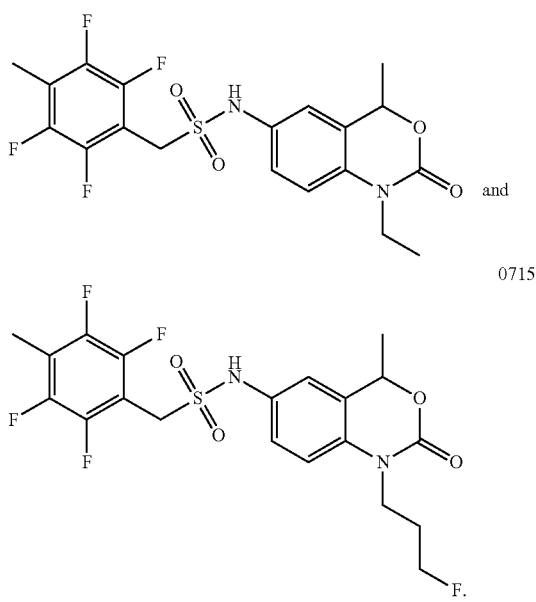

In the second aspect of the present invention, a use of a compound represented by formula (I), or a salt, or an optical isomer, or a raceme, or a solvate, or a precursor thereof according to the first aspect of the present invention is provided for the preparation of an agricultural formulation or a composition, which is used for (i) the enhancement of plant stress resistance; (ii) the preparation of an agonist for ABA receptor; and/or (iii) the preparation of an inhibitor for the seed germination.

In another preferred embodiment, the agonist promotes the interaction of the ABA receptor PYL protein with the PP2C protein phosphatase.

In another preferred embodiment, the agricultural formulation or the composition is used for one or more of the following uses:

(i) promoting the interaction of the ABA receptor PYL protein with the PP2C protein phosphatase;
(ii) reducing the transpiration of the leaves;
(iii) inhibiting the seed germination.

In another preferred embodiment, the stress resistance is ABA-related abiotic stress resistance.

In another preferred embodiment, the stress resistance is selected from the group consisting of: a drought resistance, a cold tolerance, a salt tolerance, an osmotic pressure resistance, a heat resistance, and a combination thereof.

In another preferred embodiment, the plant is a plant that contains ABA receptor(s) of PYR/PYL family.

In another preferred embodiment, the plant comprises a moss, a fern, a gymnosperm, a monocotyledon and a dicot.

In another preferred embodiment, the plant comprises an agricultural plant, a horticultural plant, and a forestry plant.

In another preferred embodiment, the plant comprises a woody plant, and an herb.

In another preferred embodiment, the plant comprises a complete plant, an organ (such as a root, a stem, a leave, a branch, a flower, a fruit, or a seed), a tissue (such as a callus), or a cell.

In another preferred embodiment, the plant is selected from the group consisting of: Poaceae, Asteraceae, Liliaceae, Cruciferae, Rosaceae, Leguminosae, Theaceae, Sterculiaceae, Pinaceae, Juglandaceae, Piperaceae, Magnoliaceae, Ericaceae, Actinidiaceae, Vitaceae, Begoniaceae, Bromeliaceae, Ginkgoaceae, Illiciaceae, Zingiberaceae, Punicaceae, Apocynaceae, Berberidaceae, Rutaceae, Solanaceae, Cupressaceae, Aquifoliaceae, Palmae, and a combination thereof.

In another preferred embodiment, the plant is selected from the group consisting of: *Arabidopsis*, tobacco, cotton, lettuce, rice, wheat, corn, peanut, sorghum, oats, rye, sugarcane, soybean, potato, buckwheat, pepper, grape, pear, apple, banana, *ginseng*, tomato, cayenne pepper, eggplant, cauliflower, chinese cabbage, oilseed rape, cucumber, watermelon, onion, sunflower, lily, rose, *chrysanthemum*, peony, carnation, camphor tree, Chinese parasol tree, pine tree, and a combination thereof.

In the third aspect of the present invention, an agricultural formulation is provided, which comprises:

(i) a compound represented by formula (I), or a salt, or an optical isomer, or a raceme, or a solvate, or a precursor thereof according to the first aspect of the present invention; and (ii) an agriculturally acceptable carrier.

In another preferred embodiment, in the agricultural formulation, the content of component (i) is 0.1-1000 μM, preferably 1-200 μM, more preferably 5-100 μM.

In another preferred embodiment, the agricultural formulation contains 0.0001-99 wt %, preferably 0.1-90 wt % of component (i), based on the total weight of the agricultural formulation.

In another preferred embodiment, the agricultural formulation further comprises an additional drought-resistant agent (such as a drought-resistant seed dressing agent, a drought-resistant moisture holding agent, or a drought-resistant spray agent) or other agricultural active ingredients.

In another preferred embodiment, the agricultural active ingredient is selected from the group consisting of: fungicides, herbicides, pesticides, nematicides, insecticides, plant activators, synergists, plant growth regulators, and acaricides.

In another preferred embodiment, the agricultural formulation further comprises a surfactant (such as a cationic surfactant, an anionic surfactant, an amphoteric surfactant, or a non-ionic surfactant).

In another preferred embodiment, the dosage form of the agricultural formulation is selected from the group consisting of: solutions, emulsions, suspensions, powders, foaming agents, pastes, granules, aerosols, and a combination thereof.

In the fourth aspect of the present invention, a method for enhancing the plant stress resistance is provided, by administering to a plant a compound of formula I, or a salt, or an optical isomer, or a racemate, or a solvate, or a precursor thereof according to the first aspect of the present invention or an agricultural formulation according to the third aspect of the present invention.

In another preferred embodiment, the administering is selected from the group consisting of: spraying or irrigating.

In another preferred embodiment, the dosage for administering is 2-100 g/hectare, preferably 4-80 g/hectare, more preferably 6-60 g/hectare.

In another preferred embodiment, the dosage for administering is 1-5000 μg/plant, preferably 10-2500 μg/plant, more preferably 20-1000 μg/plant.

In the fifth aspect of the present invention, a method for preparing a compound of formula I or a salt thereof, comprising steps of:

(a) reacting a compound of formula I-A with a compound of formula I-S2 in an inert solvent, thereby forming a compound of formula I:

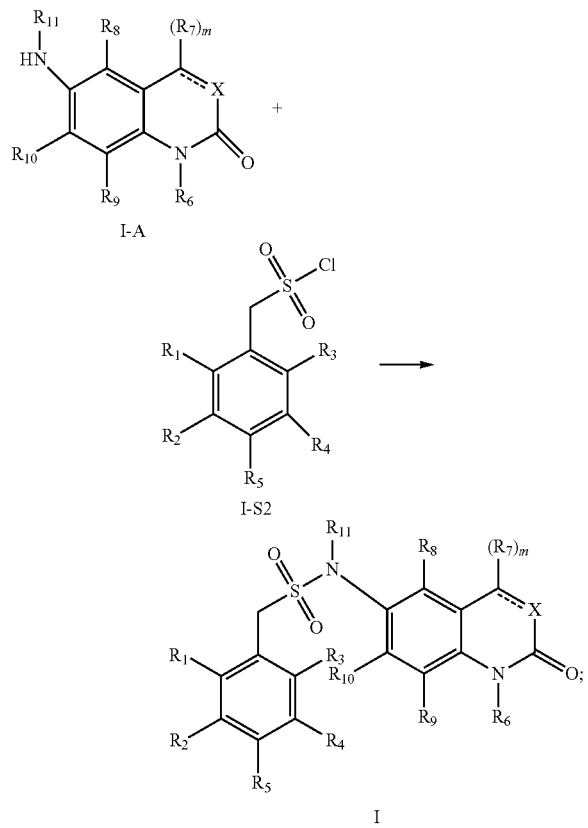

In each formula, $R_1$, $R_2$, $R_3$, $R_4$, $R_5$, $R_6$, $R_7$, $R_8$, $R_9$, $R_{10}$, $R_{11}$, m, X, "=====" are defined as in the first aspect of the present invention.

In another preferred embodiment, the inert solvent is selected from the group consisting of: N, N-dimethylformamide (DMF), dichloromethane (DCM), acetonitrile (ACN), and a combination thereof.

In another preferred embodiment, the reaction is carried out in the presence of an acid-binding agent.

In another preferred embodiment, the acid-binding agent is selected from the group consisting of: potassium carbonate ($K_2CO_3$), triethylamine ($Et_3N$), pyridine (Py), and a combination thereof.

In another preferred embodiment, in step (a), the reaction temperature is 0-150° C. (or refluxing temperature), preferably 10-60° C., more preferably 20-40° C.

In another preferred embodiment, in step (a), the reaction time is 0.1-72 hours, more preferably 1-24 hours, more preferably 8-20 hours, more preferably 4-12 hours.

In another preferred embodiment, in formula I-A, X is O, and "=====" is a single bond.

In another preferred embodiment, the compound I-S2 is prepared by the following method:

(i) reacting a compound of formula I-SS1 with thiourea in an inert solvent, thereby forming a compound of formula I-S2:

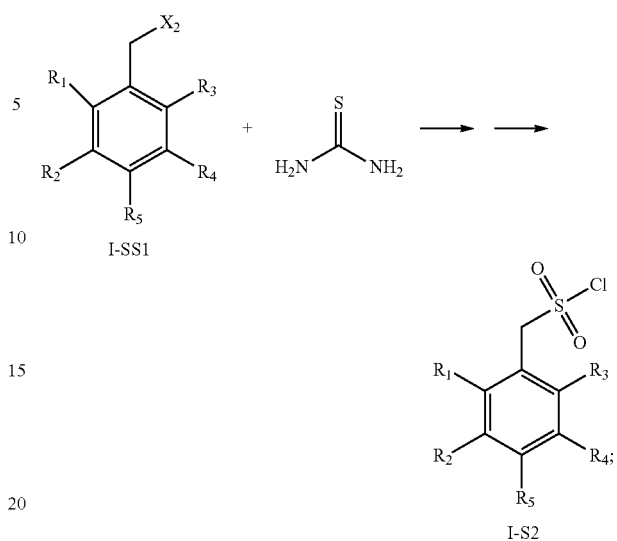

in each formula, $R_1$, $R_2$, $R_3$, $R_4$, and $R_5$ are defined as in the first aspect of the present invention, $X_2$ is a leaving group (such as Cl, Br or I).

In another preferred embodiment, the inert solvent is selected from the group consisting of: ethanol, acetonitrile, tetrahydrofuran, and a combination thereof.

In another preferred embodiment, the reaction is carried out in the presence of acid.

In another preferred embodiment, the acid is selected from the group consisting of: hydrochloric acid, hydrobromic acid, and a combination thereof.

In another preferred embodiment, in step (i), the reaction temperature is 0-150° C. (or refluxing temperature), preferably 10-50° C., more preferably 15-25° C.

In another preferred embodiment, in step (i), the reaction time is 0.1-72 hours, more preferably 1-24 hours, more preferably 2-12 hours.

It should be understood that, within the scope of the present invention, each technical feature of the present invention described above and in the following (as examples) may be combined with each other to form a new or preferred technical solution, which is not listed here due to space limitations.

DESCRIPTION OF FIGURE

The patent or application file contains at least one drawing and at least one photograph executed in color. Copies of this patent or patent application publication with color drawing(s) will be provided by the Office upon request and payment of the necessary fee. Applicant submits that the color versions of the figures are part of the original disclosure. No new matter has been added.

FIG. 4 shows that treatment of the compounds 0224, 0304, 0706, 0715 or 0428 of the present invention has significantly reduced the leaf transpiration rate, resulting in an increased leaf temperature in *Arabidopsis*. Wherein FIG. 4a shows that after treating with 5 µM ABA or compound 0224, the leaf temperature is significantly increased compared to that with control (DMSO) treatment, and the duration of compound 0224 is longer. FIG. 4b shows that after treating with 5 µM compound 0304, the leaf temperature is significantly increased compared to that with control (DMSO) treatment. While after the concentration of compound 0224 has been decreased to 2 µM or 1 µM, the leaf temperature is still significantly increased compared to that with control (DMSO) treatment, and the effect is gradually decreased, indicating that there is a concentration-dependent effect for the inhibitory effect of compound 0224 on leaf transpiration. FIG. 4c shows that after treating with 5 µM compound 0706 or 0715, the leaf temperature is significantly increased compared to that with control (DMSO) treatment, the duration of which is equivalent to that of 0224. FIG. 4d shows that after treating with 5 µM, 2 µM and 1 µM compound 0428, the leaf temperature is significantly increased compared to that with DMSO treatment, and the leaf temperature is increased with the increase of the concentration, indicating that there is a concentration-dependent effect for the inhibitory effect of compound 0428 on the leaf transpiration.

and ABA. Compound 0428 can promote the interaction of the *Arabidopsis* protein phosphatase HAB1 with soybean GmPYL6 or rice OsPYL2, and this interaction is dose-dependent.

Figure 14A:
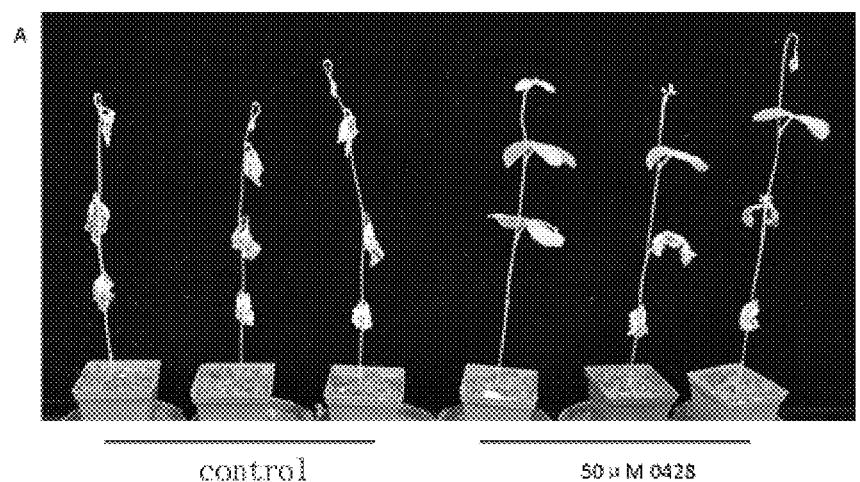
Figure 14B:
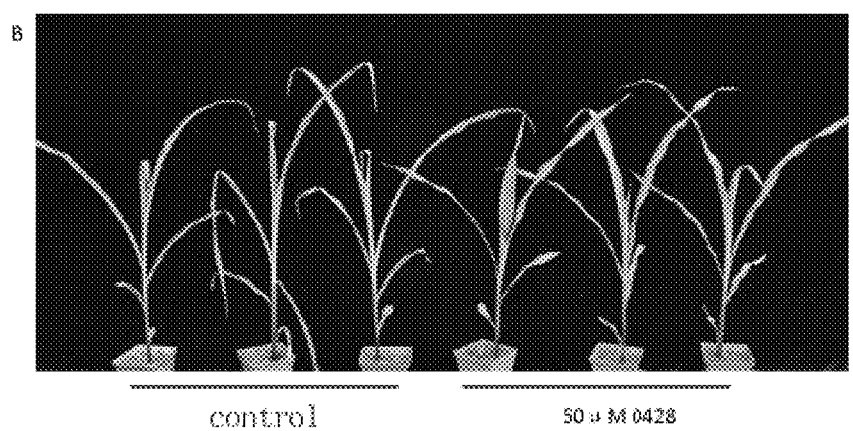

FIGS. 14a and 14b show the results of soil drought experiments on soybean and corn, respectively. The corn at small bell-mouthed period and soybean at the triple trifoliate stage are selected, and the compounds of the present invention (such as, compound 0428) are sprayed on the first day and the second day after the onset of drought. The overall growth condition of the corn after 4 days of drought treatment and the soybean after 9 days of drought treatment is shown in the figure. The concentration of compound 0428 in the experiment is 50 μM. The growth condition of corn and soybean treated with compound 0428 is significantly better than that in the control group.

Figure 15:
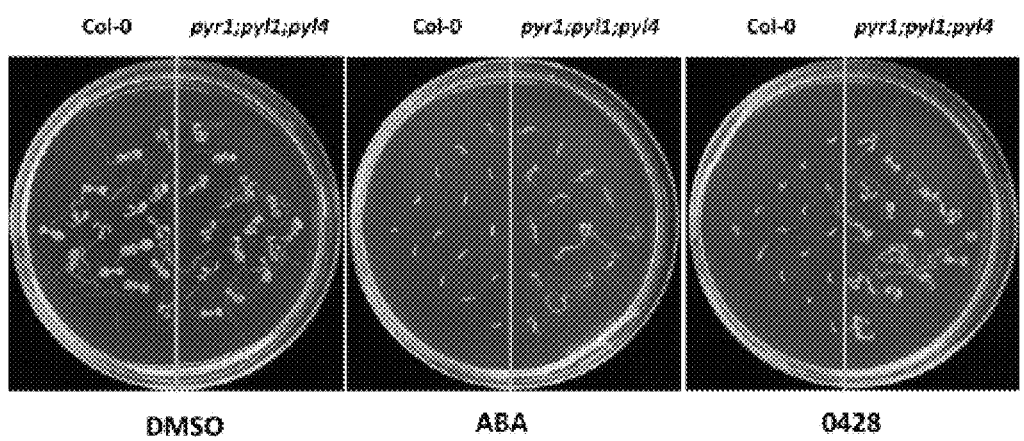

FIG. 15 shows the effect of compound 0428 and ABA on the seed germination of Col-0 and pyr1;pyl1;pyl4 triple mutant at a concentration of 2 μM. Col-0 is sown on the left half and the pyr1;pyl1;pyl4 triple mutant is sown on the right half of the culture dish. The photos are taken 7 days after seed germination (9 days after sowing) of the pyr1;pyl1;pyl4 triple mutants. DMSO treatment is used as a control group. The results show that the compound 0428 can inhibit the seed germination of the Col-0, but the inhibitory effect on the seed germination of the pyr1;pyl1;pyl4 triple mutants is significantly reduced, indicating that the seed germination inhibition of the compound 0428 in the *Arabidopsis* is mediated through ABA receptors, rather than toxic effects.

Figure 16:
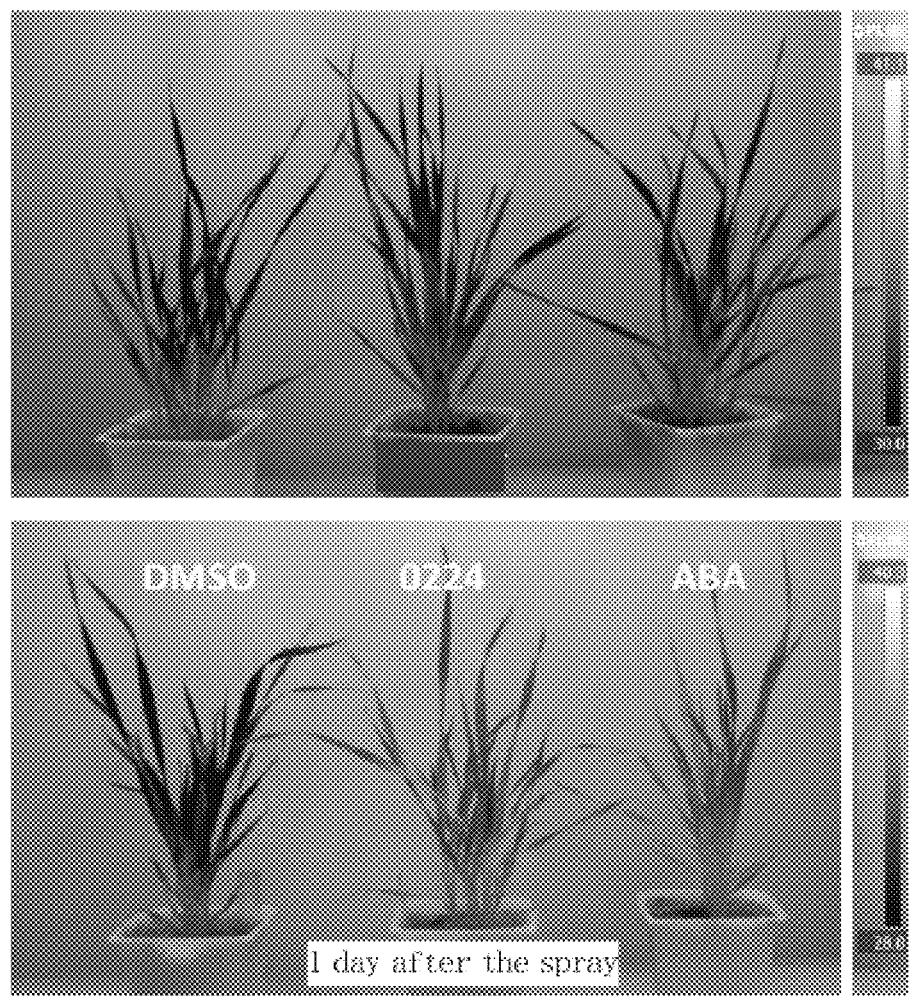

FIG. 16 shows that treatment with the compound 0224 of the present invention has significantly reduced the transpiration rate of the wheat leaf, resulting in an increased leaf temperature. 18 days after sowing, the wheat plants are stopped watering and the compound 0224 of the present invention is sprayed. Compared with the control group (DMSO), 100 μM compound 0224 can significantly reduce the transpiration rate of the wheat leaf.

Figure 17:
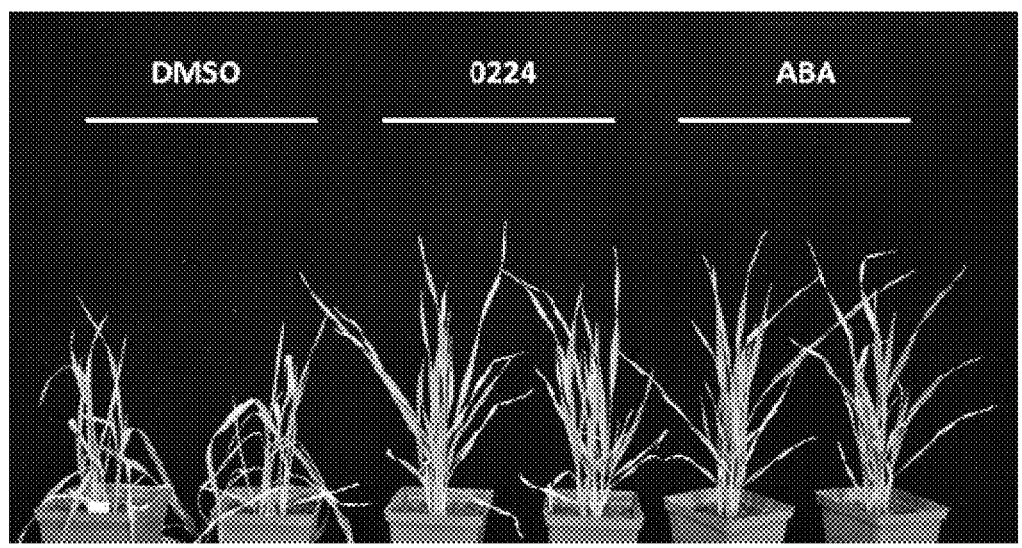

FIG. 17 shows the results of soil drought experiments on wheat. The wheat in FIG. 16 was photographed after 6 days of drought, and the photos show that the growth condition of wheat treated with 100 μM compound 0224 or ABA is significantly better than that in the control group (DMSO).

DETAILED DESCRIPTION

After an extensive and in-depth study, the present inventors have firstly developed a class of ABA alternatives (the compounds of the present invention) with high abscisic acid (ABA) activities. The compounds of the present invention can significantly enhance the multi-resistance of the plant (such as drought resistance, cold tolerance, etc.). In addition, the compounds of the present invention are easy to be prepared, and have the advantages such as excellent environmental friendliness and a rapid action and so on, and therefore they have a broad application prospect. On this basis, the inventors complete the present invention.

Experiments have shown that the compounds of the present invention can bind to a number of PYR/PYL receptors, and in vitro activity of which is better than Abscisic Acid (ABA), and can significantly increase the stress resistance of a variety of different plants.

Group Definition

As used herein, the term "substituted or unsubstituted" means that the group may be unsubstituted, or the H in the group is substituted with one or more (such as, 1-10, preferably 1-5, more preferably 1-3, most preferably 1-2) substituents.

As used herein, the "substitution" or "substituted" means that the group has one or more (preferably 1-6, more preferably 1-3) substituents selected from the group consisting of: halogen, hydroxyl, —$NH_2$, nitro, —CN, $C_1$-$C_4$ alkyl, $C_1$-$C_4$ haloalkyl, $C_1$-$C_4$ alkoxy, $C_3$-$C_6$ cycloalkyl, $C_1$-$C_3$ carboxyl, $C_2$-$C_4$ alkenyl, $C_2$-$C_4$ alkynyl.

As used herein, the term "$C_1$-$C_7$ alkyl" refers to a straight or branched alkyl group having 1 to 7 carbon atoms, such as methyl, ethyl, propyl, isopropyl, butyl, isobutyl, sec-butyl, t-butyl, or the like. When not otherwise specified, the term includes substituted or unsubstituted C alkyl.

As used herein, the term "$C_1$-$C_6$ alkyl" refers to a straight or branched alkyl group having 1 to 6 carbon atoms, such as methyl, ethyl, propyl, isopropyl, butyl, isobutyl, sec-butyl, t-butyl, or the like. When not otherwise specified, the term includes substituted or unsubstituted $C_1$-$C_6$ alkyl.

As used herein, the term "$C_1$-$C_4$ alkyl" refers to a straight or branched alkyl group having 1 to 4 carbon atoms, such as methyl, ethyl, propyl, isopropyl, butyl, isobutyl, sec-butyl, t-butyl, or the like. When not otherwise specified, the term includes substituted or unsubstituted $C_1$-$C_4$ alkyl.

As used herein, the term "$C_1$-$C_3$ alkyl" refers to a straight or branched alkyl group having 1 to 3 carbon atoms, such as methyl, ethyl, propyl, isopropyl, or the like. When not otherwise specified, the term includes substituted or unsubstituted $C_1$-$C_3$ alkyl.

As used herein, the term "$C_1$-$C_2$ alkylene" refers to a divalent hydrocarbon group having 1-2 carbon atoms, such as methylene, ethylene, or the like. When not otherwise specified, the term includes substituted or unsubstituted $C_1$-$C_2$ alkylene.

As used herein, the term "$C_2$-$C_7$ alkenyl" refers to a straight or branched alkenyl group having 2 to 7 carbon atoms, such as ethenyl, allyl, 1-propenyl, isopropenyl, 1-butenyl, 2-butenyl, or the like. When not otherwise specified, the term includes substituted or unsubstituted $C_2$-$C_7$ alkenyl.

As used herein, the term "$C_2$-$C_6$ alkenyl" refers to a straight or branched alkenyl group having 2 to 6 carbon atoms, such as ethenyl, allyl, 1-propenyl, isopropenyl, 1-butenyl, 2-butenyl, or the like. When not otherwise specified, the term includes substituted or unsubstituted $C_2$-$C_6$ alkenyl.

As used herein, the term "$C_2$-$C_3$ alkenyl" refers to a straight or branched alkenyl group having 2 to 3 carbon atoms, such as ethenyl, allyl, 1-propenyl, isopropenyl or the like. When not otherwise specified, the term includes substituted or unsubstituted $C_2$-$C_3$ alkenyl.

As used herein, the term "$C_2$-$C_7$ alkynyl" refers to a straight or branched alkynyl group having 2 to 7 carbon atoms, such as ethynyl, propynyl, or the like. When not otherwise specified, the term includes substituted or unsubstituted $C_2$-$C_7$ alkynyl.

As used herein, the term "$C_2$-$C_6$ alkynyl" refers to a straight or branched alkynyl group having 2 to 6 carbon atoms, such as ethynyl, propynyl, or the like. When not otherwise specified, the term includes substituted or unsubstituted $C_2$-$C_6$ alkynyl.

As used herein, the term "$C_2$-$C_3$ alkynyl" refers to a straight or branched alkynyl group having 2 to 3 carbon atoms, such as ethynyl, propynyl, or the like. When not otherwise specified, the term includes substituted or unsubstituted $C_2$-$C_3$ alkynyl.

As used herein, the term "$C_3$-$C_8$ cycloalkyl" refers to a cyclic alkyl having 3 to 8 carbon atoms, such as cyclopropyl, cyclobutyl, cyclopentyl, cyclohexyl, cycloheptyl, or the like. When not otherwise specified, the term includes substituted or unsubstituted $C_3$-$C_8$ cycloalkyl.

As used herein, the term "$C_3$-$C_7$ cycloalkyl" refers to a cyclic alkyl having 3 to 7 carbon atoms, such as cyclopropyl, cyclobutyl, cyclopentyl, cyclohexyl, cycloheptyl, or the like. When not otherwise specified, the term includes substituted or unsubstituted $C_3$-$C_7$ cycloalkyl.

As used herein, the term "$C_3$-$C_6$ cycloalkyl" refers to a cyclic alkyl having 3 to 6 carbon atoms, such as cyclopropyl, cyclobutyl, cyclopentyl, cyclohexyl, cycloheptyl, or the like. When not otherwise specified, the term includes substituted or unsubstituted $C_3$-$C_6$ cycloalkyl.

As used herein, the term "$C_5$-$C_{10}$ heterocyclyl" refers to a saturated, partially saturated, or unsaturated group (but not aromatic) having a single ring or fused ring (including bridged ring systems and spiro ring systems, having 5 to 10 carbon atoms and 1 to 2 heteroatoms selected from nitrogen, sulfur or oxygen). In a fused ring system, one or more rings may be cycloalkyl, aryl or heteroaryl, provided that the point of attachment passes non-aromatic rings. The term includes substituted or unsubstituted heterocyclyl.

As used herein, the term "$C_5$-$C_8$ heterocyclyl" refers to a saturated, partially saturated, or unsaturated group (but not aromatic) having a single ring or fused ring (including bridged ring systems and spiro ring systems, having 5 to 8 carbon atoms and 1 to 2 heteroatoms selected from nitrogen, sulfur or oxygen). In a fused ring system, one or more rings may be cycloalkyl, aryl or heteroaryl, provided that the point of attachment passes non-aromatic rings. The term includes substituted or unsubstituted heterocyclyl.

As used herein, the term "$C_1$-$C_3$ haloalkyl" refers to a straight or branched alkyl group having 1 to 3 carbon atoms in which hydrogen is substituted with one or more halogen, for example, halomethyl, haloethyl, halopropyl, haloisopropyl, or the like. When not otherwise specified, the term includes substituted or unsubstituted $C_1$-$C_3$ haloalkyl.

As used herein, the term "$C_1$-$C_6$ alkoxy" refers to a group having a "($C_1$-$C_6$ alkyl)-O—" structure, for example, $CH_3$—O—, $C_2H_5$—O—, $C_3H_7$—O—, $(CH_3)_2CH$—O—, $nC_4H_9$—O—, $tC_4H_9$—O—, or the like, and when not otherwise specified, the term includes substituted or unsubstituted $C_1$-$C_6$ alkoxy.

As used herein, the term "$C_1$-$C_4$ alkoxy" refers to a group having a "($C_1$-$C_4$ alkyl)-O—" structure, for example, $CH_3$—O—, $C_2H_5$—O—, $C_3H_7$—O—, $(CH_3)_2CH$—O—, $nC_4H_9$—O—, $tC_4H_9$—O—, or the like, and when not otherwise specified, the term includes substituted or unsubstituted $C_1$-$C_4$ alkoxy.

As used herein, the term "halogen" refers to fluorine, chlorine, bromine, or iodine, preferably fluorine or chlorine, most preferably fluorine.

As used herein, the term "halogenated" refers to a group that is substituted with one or more of the same or different halogen atoms described as above, which may be partially halogenated or perhalogenated, such as trifluoromethyl, pentafluoroethyl, heptafluoroisopropyl, or the like.

The compounds of the present invention may contain one or more asymmetric centers and therefore occur as racemates, racemic mixtures, single enantiomers, diastereomeric compounds, and single diastereomers. The asymmetric center that can exist depends on the nature of the various substituents on the molecule. Each such asymmetric center will independently produce two optical isomers, and all possible optical isomers and diastereomeric mixtures and pure or partially pure compounds are included within the scope of this invention. The invention includes all isomeric forms of the compounds.

Compounds of the Present Invention and the Preparation Method Thereof

As used herein, the terms "compounds of the present invention", "ABA substitutes of the present invention", and "compound of formula I" can be used interchangeably, all of which refer to compounds having the structure shown in Formula I. In addition, the terms also include salts, optical isomers, racemates, solvates (such as hydrates), and/or precursors of the compounds of formula I,

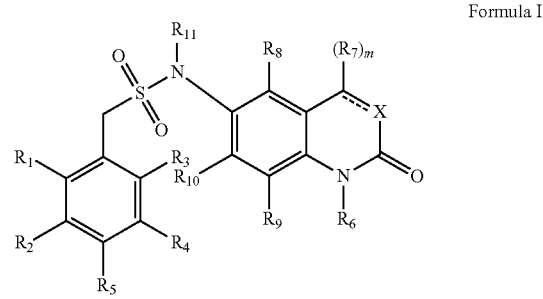

Formula I wherein $R_1$-$R_{10}$, $R_{11}$, m, X, and "═══" are defined as above.

In another preferred embodiment, the compound has a structure of Formula Ia:

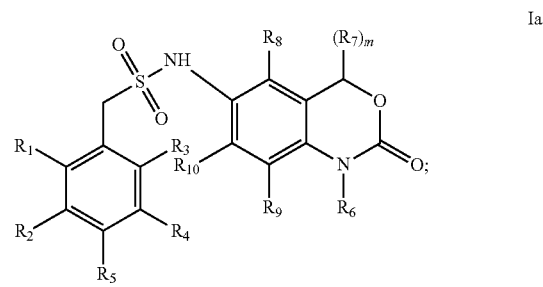

Ia wherein $R_1$-$R_{10}$, and m are defined as above.

In another preferred embodiment, the compound has a structure of Formula Ib:

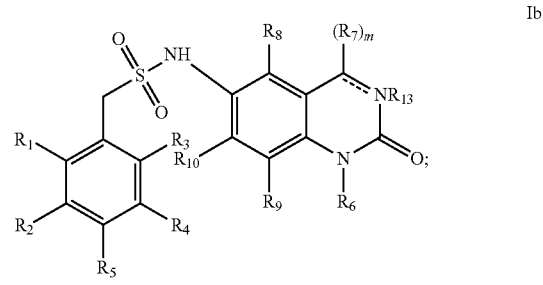

Ib wherein $R_1$-$R_{10}$, $R_{13}$, m, and "═══" are defined as above.

In another preferred embodiment, the compound has a structure of Formula Ic:

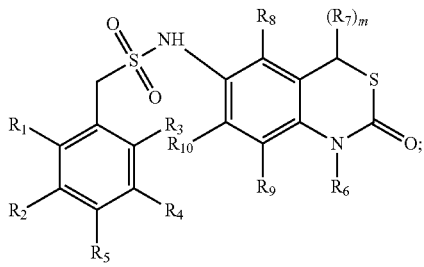

wherein $R_1$-$R_{10}$, and m are defined as above.

In another preferred embodiment, the compound has a structure of Formula Id:

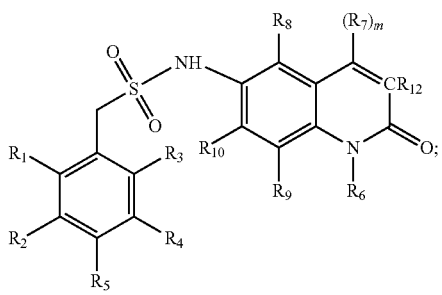

wherein $R_1$-$R_{10}$, $R_{12}$, and m are defined as above.

The preparation method of the compounds of formula I according to the present invention is described more specifically as below, but which are not intended to limit the invention in any way. The compounds of the present invention may also be conveniently prepared by a combination of various synthesis methods described in the presenting specification or known in the art, and such combinations are readily available to those skilled in the art. In general, in the preparation method of the present invention, most of the reactions are performed in an inert solvent at a temperature of 0° C. to 150° C. (or refluxing temperature) (preferably, 10-60° C., or 20-40° C.) for a period of time (such as, 0.1-72 hours, preferably 2-20 hours).

As used herein, the room temperature refers to 4-35° C., preferably 20-30° C.

Preferably, the compounds of formula I according to the present invention can be prepared by the following schemes, the exemplary methods described in examples and the relevant published literature used by those skilled in the art.

Typically, the preparation method of the compounds of Formula Ia of the present invention can include, but is not limited to, the following schemes.

Scheme I (Taking X=O, $R_6$=Propyl, $R_7$=Methyl, $R_8$=H, $R_9$=H, $R_{10}$=H, m=1 as an Example)

(1) Preparation of 1-propyl-4-methyl-6-amino-1,4-dihydrobenzoxazole-2-one

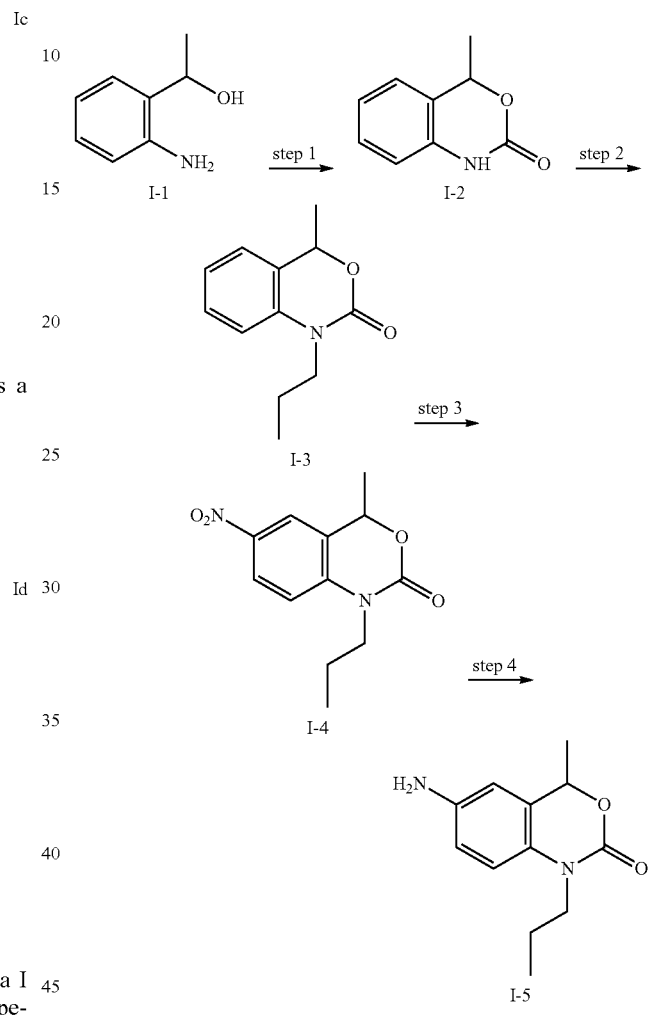

In step 1, firstly, reacting the compound of formula I-1 with N,N'-carbonyldiimidazole (CDI) in an inert solvent (such as tetrahydrofuran) at a certain temperature (such as, 20-40° C.) for a period of time, thereby forming a compound of formula I-2.

Step 2: in the presence of an alkali (such as sodium hydride), reacting the compound of formula I-2 with iodopropane in an inert solvent (such as N—N-dimethylformamide) at a certain temperature (such as 20-40° C.) for a period of time, thereby forming a compound of formula I-3.

Step 3: In the presence of an acid (such as sulfuric acid), reacting the compound of formula I-3 with potassium nitrate at a certain temperature (such as 0-10° C.) for a period of time, thereby forming a compound of formula I-4.

Step 4: In an inert solvent (such as methanol), the compound of formula Ia-4 is subjected to a reduction reaction with palladium on carbon as a catalyst at a certain temperature (such as 20-40° C.), thereby forming a compound of formula I-5.

(2) Preparation of 4-methylhalobenzylsulfonyl Chloride

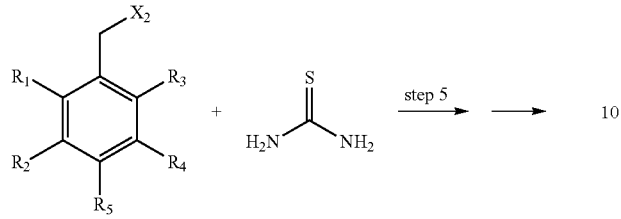

I-SS1 (R$_5$ = methyl)

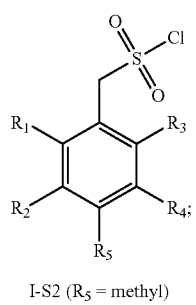

I-S2 (R$_5$ = methyl)

Step 5: In an inert solvent (such as ethanol, acetonitrile), reacting the compound of formula I-SS1 (such as 2, 3, 5, 6-tetrafluoro-4-methylbenzyl bromide or 2, 3, 5, 6-tetrafluoro-4-methylbenzyl chloride) with thiourea, thereby forming a reaction product; and then in the presence of an acid (such as concentrated hydrochloric acid), reacting the reaction product with sodium chlorite in an inert solvent (such as acetonitrile) at a certain temperature (such as 15-25° C.), thereby forming a compound of formula I-S2.

(3) Preparation of a Compound of Formula Ia

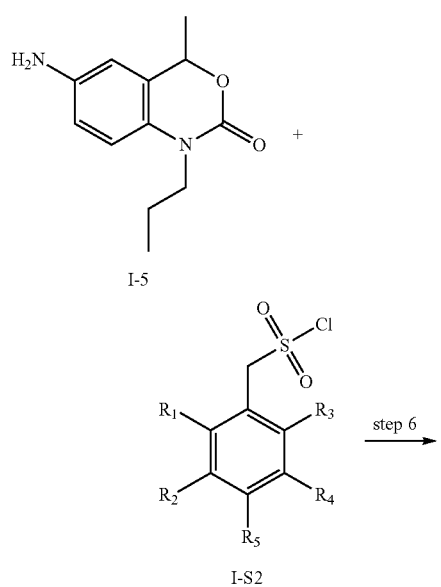

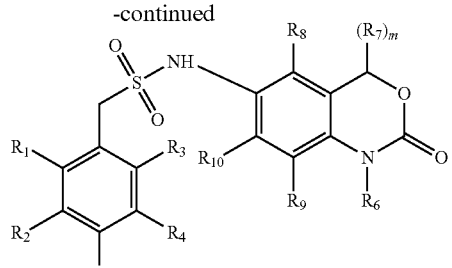

Ia(R$_6$ = propyl, R$_7$ = methyl, m = 1)

Step 6: in the presence of an acid binding agent (such as potassium carbonate), reacting the compound of formula I-5 with the compound of formula I-S2 in an inert solvent (such as DMF) at a certain temperature (such as 20-50° C.) for a period of time, thereby forming a compound of formula Ia.

In scheme I, X$_2$ is a leaving group, which is chlorine, bromine or iodine. Other substituents and groups are as defined in the specification.

Agricultural Formulations

The active substances (compounds of formula I, or salts thereof, or optical isomers thereof, or racemates thereof, or solvates thereof, or precursors thereof) of the present invention may be prepared into agricultural formulations in conventional manners, for example, solutions, emulsions, suspensions, dusts, foaming agents, pastes, granules, aerosols, natural and synthetic materials impregnated with active substances, microcapsules in polymers, coating materials for seeds.

These formulations can be produced by known methods, for example, by mixing the active compounds with extenders which are liquid or liquefied or solid diluents or carriers and optionally with surfactants, that is, emulsifiers and/or dispersants and/or foam formers. For example, when water is used as an extender, organic solvents can also be used as auxiliaries.

It is basically suitable when using a liquid solvent as a diluent or a carrier, for example, aromatic hydrocarbons such as xylene, toluene or alkyl naphthalene; chlorinated aromatic or chlorinated aliphatic hydrocarbons such as chlorobenzene, vinyl chloride or methylene chloride; aliphatic hydrocarbons such as cyclohexane, or paraffins such as mineral oil fractions; alcohols and their ethers and esters such as ethanol or ethylene glycol; ketones such as acetone, methyl ethyl ketone, methyl isobutyl ketone or cyclohexanone; or less commonly used polar solvents such as dimethylformamide and dimethyl sulfoxide, and water.

In the case of liquefied diluents or carriers, they refer to a liquid that will become a gas at an atmospheric temperature and an atmospheric pressure, such as an aerosol propellant such as halogenated hydrocarbons as well as butane, propane, nitrogen and carbon dioxide.

The solid carrier may be ground natural minerals such as kaolin, clay, talc, quartz, activated clay, montmorillonite, or diatomaceous earth, as well as ground synthetic minerals such as highly dispersed silicic acid, alumina and silicates. Solid carriers for granules are ground and fractionated natural zircons such as calcite, marble, pumice, sepiolite and dolomite, as well as synthesized granules by inorganic and organic coarse powder, and organic materials such as particles of sawdust, coconut shell, corn cobs, tobacco stems and so on.

Nonionic and anionic emulsifiers can be used as emulsifiers and/or foam formers. For example, polyoxyethylene-fatty acid esters, polyoxyethylene-fatty alcohol ethers, for example alkylaryl polyglycol ethers, alkyl sulfonates, alkyl sulfates, arylsulfonates and albumin hydrolysate. Dispersants include, for example, lignin sulfite waste liquors and methylcellulose.

Binders, such as carboxymethylcellulose and natural and synthetic polymers in the form of powders, granules or emulsions, may be used in the formulation, such as acacia, polyvinyl alcohol and polyvinyl acetate.

Colorant may be used, for example inorganic dyes such as iron oxide, cobalt oxide and Prussian Blue; organic dyes such as organic dyes of azo dyes or metal titanium cyanine dyes; and trace nutrients such as salts of iron, manganese, boron, copper, cobalt, aluminum and zinc and the like.

In the present invention, the "agricultural formulation" is generally an agricultural plant growth regulator, which comprises a compound of formula I or a salt, an optical isomer, a racemate, a solvate or a precursor thereof as an active ingredient for enhancing the plant stress resistance (such as drought resistance); and an agriculturally acceptable carrier.

As used herein, the "agriculturally acceptable carrier" is an agriculturally acceptable solvent, suspension, or excipient which is used to deliver the compounds of formula I or salts, optical isomers, racemates, solvates, or precursors thereof of the present invention to a plant. The carrier can be liquid or solid. An agriculturally acceptable carrier suitable for use in the present invention is selected from the group consisting of: water, buffers, DMSO, surfactants such as Tween-20, and a combination thereof. Any agriculturally acceptable carrier known to those skilled in the art may be used in the present invention.

The agricultural formulations of the present invention may be formulated with other drought-resistant agents into a mixture to be present in their product formulations or in the dosage forms prepared from these formulations, such other drought-resistant agents include (but are not limited to) drought-resistant seed dressing agents, drought-resistant moisture holding agents, or drought-resistant spray agents.

In addition, the agricultural formulations of the present invention may also be formulated with synergists into a mixture to be present in their product formulations or in the dosage forms prepared from these formulations, and these synergists are compounds which enhance the action of the active compound. Since the active compound itself is active, the synergists may not be added.

The dosage forms of the agricultural formulations of the present invention can be varied, and all of those which can allow the effective delivery of the active ingredient into the plant in vivo can be used. From the standpoint of easy for preparation and administration, the preferred agricultural formulation is a spray or a solution.

The agricultural formulations of the present invention usually contain from 0.0001 to 99 wt %, preferably from 0.1 to 90 wt %, of the compounds of the present invention, based on the total weight of the agricultural formulation. The concentration of the compounds of the present invention in commercial formulations or used dosage forms can be widely varied. The concentration of the compounds of the present invention in commercial formulations or used dosage forms may range from 0.0000001-100% (g/v), preferably between 0.0001 and 1% (g/v).

Method for Enhancing the Plant Stress Resistance

The present invention provides a method for enhancing the plant stress resistance, such as drought resistance, cold tolerance, comprising steps of: administering to a plant a compound of formula I or a salt, an optical isomer, a racemate, a solvate or a precursor thereof, or a corresponding agricultural formulation thereof.

Administration can be carried out by various methods which are already known, for example, by spraying, atomizing, dusting or broadcast sowing the compound or the agricultural formulation containing the compound on plant leaves, propagation material, or by other manners to contact the plant with the compound or the agricultural formulation containing the compound, if to contact seeds, they are treated by coating, wrapping or other ways. Another method of treating plants or seeds directly before planting is to introduce the agricultural formulation of the present invention into the soil or other medium to be sown. In some embodiments, a carrier can also be used, which may be in a solid, liquid state as described above.

In a preferred embodiment, the compound or the agricultural formulation containing the compound may also be delivered to the plant by spraying (such as aircraft spraying) or irrigating.

The Main Advantages of the Present Invention Include:

For the first time, a class of ABA alternatives (compounds of the present invention) with a high abscisic acid (ABA) activity has been developed. The compounds of the present invention can significantly enhance a variety of stress resistances (such as drought resistance, cold tolerance, etc.) of the plant. In addition, the compounds of the present invention are easy for preparations, and have an excellent environmental friendliness, and therefore have a broad application prospect. On this basis, the present invention has been completed.

Experiments have shown that the compounds of the present invention (such as compounds 0224, 0304, 0706, 0708, 0713, 0715, 0428, 1022B and the like) can bind to a number of different PYL receptors, in vitro activity of which is significantly better than that of Abscisic Acid (ABA) and can significantly enhance the stress resistance of a variety of different plants.

(1) The present invention has synthesized a series of highly active alternatives of natural abscisic acid (ABA) for the first time. The compounds of the present invention can significantly enhance a variety of stress resistances in plants (such as drought resistance and cold tolerance). Also, all of the optical isomers or racemates of the present compounds have a high activity.

(2) The activity of the compounds of the present invention is significantly better than abscisic acid (ABA) and the existing ABA analogs.

(3) The compounds of the present invention can promote the interaction between a plurality of PYR/PYL receptor proteins and PP2C protein phosphatase HAB1.

(4) The synthesis methods of the compounds of the present invention are simple and cost low.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise indicated, percentages and parts are by weight and parts by weight.

Unless otherwise specified, materials and reagents used in the examples of the present invention are all commercially available products.

Materials and General Methods

Materials

The model plants used in the experiments are all conventional or commercial available varieties, wherein *Arabidopsis thaliana* includes: Colombia (Col-0) ecotype and Col-0 ecotype-based ABA synthesis mutants aba2-1 and triple mutant (pyr1;pyl1;pyl4) of PYL receptors. Soybean varieties are commercially available Shandou 125 (0224, 0304, 0706, 0708, 0713, 0715 and 1028c) and Hanxia 10 (0428, 1022B and NC0F4), cotton varieties are commercially available upland cotton R15, and wheat varieties are commercially available Xinong 979, corn varieties are commercially available Yedan 13.

The compounds of the present invention (such as 0224, 0304, 0706, 0708, 0713, 0715, 1028c, 0428, 1022B and NC0F4, etc.) are shown in each example.

Plant Growth

The growth temperature for *Arabidopsis thaliana* is 22° C. The photoperiod of plants grown in a plant growth media is long-day (24-hour light), and the photoperiod of plants grown in soil (such as, in leaf transpiration experiments and soil drought experiments) is short day (8-hour light/16-hour darkness), and the light intensity is 75 $\mu mol \cdot m^{-2} \cdot s^{-1}$.

The growth temperature for soybean and cotton is 26° C. and the photoperiod is 14-hour light/10-hour darkness. The growth temperature for corn is 27° C., and the photoperiod is 11-hour light/13-hour darkness. The growth temperature for wheat is 27° C., and the photoperiod is 11-hour light/13-hour darkness. The light intensity is 400 $\mu mol \cdot m^{-2} \cdot s^{-1}$.

Unless stated otherwise, all of the plant growth media used in the experiments are ½ MS (Murashige and Skoog) solid media containing 1% (w/v) of sucrose and 0.6% (w/v) of agar (purchased from Phyto Technology Laboratories Company).

Protein Expression and Purification

The construction method of recombinant plasmids for the *Arabidopsis thaliana* genes PYL1 (amino acid sequence 36-211), PYL2 (amino acid sequence 14-188) with dual tags of 6×His and SUMO sequence and the *Arabidopsis thaliana* gene HAB1 (amino acid sequence 172-511) with the Biotin tag sequence is described in detail in "A gate-latch-lock mechanism for hormone signaling by abscisic acid receptors" (Nature, Vol 462, 2009). The construction method of recombinant plasmids for PYR1 and PYL7 (whole gene coding sequence) and Soybean GmPYL6 and rice OsPYL2 with dual tags of 6×His and SUMO sequence is the same as that for *Arabidopsis* PYL2.

The above recombinant plasmid is transformed into competent cell of *E. coli* BL21 (DE3) (purchased from NEB company), and inoculated into 200 ml of LB liquid medium containing Amp resistance (purchased from OXOID company) and cultured overnight at 37° C. at 200 rpm; and inoculated into 2 L of LB liquid medium containing Amp resistance at a ratio of 1:50-1:100 for an extended culture, and cultured at 37° C., 200 rpm for 3-4 hours, and at a low temperature of 16° C. until $OD_{600}$ is about 0.8-1.0. Recombinant plasmids for PYR1/PYL1/PYL2/PYL7/GmPYL6/OsPYL2 with dual tags of 6×His and SUMO sequence were induced overnight with 100 μM of IPTG while HAB1 recombinant plasmid with the Biotin tag sequence was induced simultaneously with 100 μM of IPTG and 40 μM of biotin.

After 16 hours of induction, the bacterial solution was centrifuged at 4000 rpm for 20 minutes at 4° C. in a low-speed high-capacity centrifuge, and the bacteria cells were collected. Bacteria cells were resuspended in 50 ml of extraction buffer (containing 20 mM Tris, pH 8.0, 200 mM NaCl and 10% (v/v) glycerol) for per 2 L of bacterial solution and then subjected to pressure-breaking at 1000 Pa and 4° C. for 3-5 times. The broken cells were subjected to ultracentrifugation, centrifuged at 16000 rpm for 30 minutes, and this process was repeated twice. The supernatant was collected and subjected to an affinity chromatography column.

For PYR/PYL proteins with dual tags of 6×His and SUMO sequences, 50 ml of affinity chromatography Ni column (50 ml Ni-NTA column, available from GE) was used. Firstly, the column was equilibrated with 600 ml of 10% buffer B (containing 20 mM Tris, PH 8.0, 200 mM NaCl, 500 mM imidazole and 10% glycerol), and then eluted with 200 ml of 50% buffer B and finally eluted with 100 ml of 100% buffer B. Proteins for crystal analysis were mixed with ulp1 enzyme at a molar ratio of 1000:1 for enzymatic dialysis overnight. The digested proteins were subjected to affinity chromatography on a Ni column once more. The collected solution was subjected to a HiLoad 26/60 Superdex200 gel filtration column (commercially available from GE) and eluted with an elution solution (containing 25 mM Tris, pH 8.0, 200 mM ammonium acetate, 1 mM dithiotreitol and 1 mM EDTA) to further separate and purify the protein.

For a HAB1 protein with a Biotin tag sequence, it was subjected to a 50 ml MBP affinity column (available from GE). The column was firstly equilibrated with 600 ml of 10% buffer C (containing 20 mM Tris, pH 8.0, 200 mM NaCl, 10 mM Maltose and 10% Glycerol), and eluted with 200 ml of 50% buffer C and finally eluted with 100 ml of 100% buffer C. The collection solution was subjected to a HiLoad 26/60 Superdex200 gel filtration column and eluted with an elution solution (containing 20 mM Tris, pH 8.0, 200 mM NaCl and 10% Glycerol) to further separate and purify the protein.

AlphaScreen Assay

The AlphaScreen kit (available from Perkin Elmer) was used, and the method was as follows: a 10× buffer (50 mM MOPS, pH 7.4, 50 mM NaF, 50 mM CHAPS, 0.1 mg/ml bovine serum albumin) diluted at 1:10, each of 100 nM HAB1 with Biotin tag sequence and PYR1/PYL1/PYL2/PYL7/GmPYL6/OsPYL2 protein with dual tags of 6×His and SUMO sequences, corresponding concentrations of (+)-ABA/0224/0304/0706/0708/0713/0715/0428/NC0F4, and 5 μg/ml donor beads and acceptor beads (available from Perkin Elmer) were contained in 150 μl of experimental system. After incubating for 1.5 hours at room temperature in the dark, it was placed into an Envision Plate Reader (available from Perkin Elmer) under the programmed AlphaScreen procedure for readings.

HAB1 Phosphatase Activity Assay 50 mM imidazole, pH 7.2, 5 mM $MgCl_2$, 0.1% β-mercaptoethanol, 0.5 μg·ml$^{-1}$ BSA, 100 nM HAB1 protein with a Biotin tag sequence, 500 nM PYL2 receptor protein with 6×His-SUMO dual tag sequence and the corresponding concentration of (+)-ABA/0224/0304/0706/0708/0713/0715/1028c/0428/1022B/NC0F4 were contained in the reaction system. The reaction system was incubated at room temperature for 30 minutes, followed by a further reaction for 30 minutes after adding an 11-amino acid phosphorylated polypeptide as a substrate. The phosphorylated polypeptide is amino acid 170-180 of SnRK2.6 protein kinase, wherein phosphorylated serine at position 175 (with a sequence of HSQPKpSTVGTP, purchased from Kingsley Company) was a known HAB1 dephosphorylation target site. After 30 minutes, chromogenic reagent (purchased from BioVision) was added and the absorbance at 650 nm was read on a microplate reader (Molecular Devices).

Gene Expression Analysis

The whole plant or leaves were taken, and RNA extraction was carried out by using conventional methods. After reverse transcription, the fluorescence quantitative PCR was carried out. Three biological samples were taken for each treatment which was performed twice. The ACT7 gene was used as a reference gene.

Protein Crystal Analysis

Prior to crystallization, the *Arabidopsis thaliana* PYL2 and HAB1 proteins with tag-removed by digested were mixed with (+)-ABA or the compound 0428 at a molar ratio of 1:1:5 and concentrated to 6 mg/ml for crystal formation. Crystal formation was carried out by the pendant-drop method; the well buffer for crystallization contained 0.2 M Di-sodium tartrate and 20% PEG 3350. After one day, the crystals could be seen, which grew to 100-120 μm in about 3-4 days. Crystals were analyzed by X-ray diffraction and the diffraction data were collected, and the structure of the complex was analyzed according to the relevant PYR/PYL receptor structure model.

Seed Germination and Soil Drought Experiments (1) Seed Germination

Take the compounds 0428 and 0224 of the present invention as examples. The seeds of *Arabidopsis thaliana* Col-0 ecotype and PYL receptor triple mutant (pyr1;pyl1;pyl4) were sterilized with NaClO and placed at 4° C. for 3 days of the vernalization, and then sown in ½ MS solid medium containing 1 μM (+)-ABA/0224 compound or 0.05% DMSO (control) or in ½ MS solid medium containing 2 μM (+)-ABA/compound 0428 of the present invention or 0.05% DMSO (control). Two lines of plant were sown simultaneously on each medium of 6 cm diameter, with 15-20 seeds sown for each line and 4 replicates for each compound. Culture medium was placed at 22° C. with long-day culture. The seeds germinated on a solid medium containing 1 μM (+)-ABA/0224 compound were photographed 6 days after sowing, and seeds germinated on solid medium containing 2 μM (+)-ABA/0428 compound were photographed 9 days after sowing.

(2) Plant Leaf Transpiration Experiment

ABA synthesis mutant aba2-1 was used in *Arabidopsis* leaf transpiration experiment. Under condition of environmental stress, the content of endogenous ABA in this mutant does not increase, and is only 1/40 of that in wild-type *Arabidopsis* Col-0 under the same condition. Therefore, this mutant is used to exclude the effect of endogenous ABA on the transpiration experiment. The plants were sprayed with a solution containing 0.05% tween-20 and corresponding concentrations of (+)-ABA/0224/0304/0706/0715/0428 or 0.05% Tween-20 and 0.05% DMSO (control) after three weeks of continuous watering with an amount of 1.2 ml/pot. Leaf transpiration experiments of soybeans were conducted at 26° C. with long-day lighting and soybeans were sprayed with a solution containing 0.1% tween-20 and 20 μM (+)-ABA/0224/0304 compound or 0.1% Tween-20 and 0.05% DMSO (control) 14 days after sowing with an amount of 4 ml/pot; the leaf transpiration experiments of cottons were sprayed with a solution containing 0.1% tween-20 and 20 μM (+)-ABA/0224 compound or 0.1% Tween-20 and 0.05% DMSO, respectively, 25 days after sowing with an amount of 4 ml/pot; the leaf transpiration experiments of wheats were sprayed with a solution containing 0.1% tween-20 and 100 μM (+)-ABA/0224 compound or 0.1% Tween-20 and 0.05% DMSO (control) 18 days after sowing with an amount of 6 ml/pot. Images were taken daily using the FLIR A655sc thermal imager at the same time before and after spraying.

(3) Soil Drought Experiment

Seeds of *Arabidopsis* Col-0 ecotype were sterilized with NaClO and then sown on ½ MS solid medium at 4° C. for 3 days of vernalization. After 6 days of growing, the well-grown seedlings having uniform size were selected and transferred into 8×7×6 cm$^3$ pots. Each pot was filled with the same weight of soil and same number of plants (six plants) was transferred to reduce experimental error. All the pots were subjected to a short-day culture at 22° C. After two weeks, watering was stopped for drought treatment. A solution containing 0.05% Tween-20 and 5 μM 0224/0706/0715/0428 or 0.05% Tween-20 and 0.05% DMSO (control) was sprayed onto the leaf surface once per week with a spray amount of 2 ml solution/pot. The position of the flowerpot was changed every day during the process of drought to reduce the error caused by environmental factors. During the whole drought period, the solution was sprayed twice in total and photos were recorded after four weeks.

Soybean, cotton and wheat for leaf transpiration experiments were used simultaneously for soil drought experiments, each pot was filled with the same weight of soil to reduce experimental error. All the soybean plants were subjected to a long-day culture at 26° C. 14 days after sowing, watering was stopped and the plants with the consistent growth condition were selected for drought treatment. At the start of the drought, a solution containing 0.1% Tween-20 and 20 μM (+)-ABA/0224/0304 or 0.1% Tween-20 and 0.05% DMSO (control) was sprayed onto the leaf surface once with a spray amount of 4 ml solution/pot. Meanwhile, the position of the pot was changed and re-watered 6 days after the drought, and the photos were taken 1 day after re-watering. The drought experiment of cotton was similar to that of soybeans, watering was stopped 25 days after sowing, the plants with the consistent growth condition were selected for drought treatment. At the start of the drought, a solution containing 0.1% Tween-20 and 20 μM (+)-ABA/0224 or 0.1% Tween-20 and 0.05% DMSO (control) was sprayed onto the leaf surface once with a spray amount of 4 ml solution/pot, and then sprayed once every 3 days. Meanwhile, the position of the pot was changed and re-watered 6 days after the drought, and the photos were taken before re-watering and 1 day after re-watering. In the drought experiment of wheat, the wheat with the consistent growth condition 16 days after sowing was selected for the drought treatment, at the start of the drought, a solution with 0.1% Tween-20 and 100 μM (+)-ABA/0224 or 0.1% Tween-20 and 0.05% DMSO (control) was sprayed once, and then sprayed once every 3 days with a spray amount of 4 ml/pot. Meanwhile, the position of the pot was changed and the photos were taken 6 days after the drought.

Soil drought experiments used for compound 0428 on soybean and maize were similar to that used for compound 0224 on soybeans, with only one plant contained in each pot. All soybean plants were long-day cultured at 26° C. Watering was stopped after the plant had three leaves in each of three groups and the plants with consistent growth were selected for drought treatment. As for corn, watering was stopped during the small bell-mouthed period for drought treatment. A solution containing 0.05% tween-20 and 50 μM (+)-0428 or 0.05% Tween-20 and 0.05% DMSO (control) was sprayed once on leaf surface on the first day and the second day of the drought, respectively, with a spray amount of 4 ml/pot. Meanwhile the pot position was also changed.

The soybeans were re-watered 9 days after the drought, the corn was re-watered 4 days after the drought, and the photos were taken the next day.

Example 1 Preparation of Compound 0224

1.1 Preparation of 4-methyl-1,4-dihydrobenzoxazole-2-one

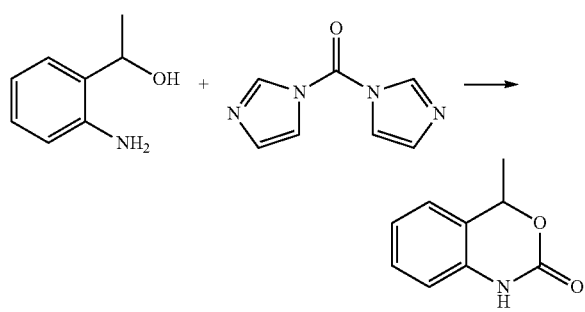

3.4 g of 1-(2-aminophenyl) ethanol and 1.6 g of CDI were added into 50 ml of anhydrous tetrahydrofuran, and the reaction was maintained at room temperature for 2 hours; the reaction was quenched by adding 1 M HCl solution and extracted with ethyl acetate. The organic phase was combined, washed with saturated aqueous sodium chloride, and the organic phase was dried over anhydrous sodium sulfate. Concentrated was performed under reduced pressure. Purification was performed through the silica gel column chromatography to give 3.8 g of a light yellow solid with a yield of 93%.

$^1$HNMR (400 MHz, DMSO-d6): δ 10.16 (s, 1H), 7.25 (t, 1H), 7.20 (d, 1H), 7.02 (t, 1H), 6.08 (d, 1H), 5.49 (m, 1H), 1.57 (d, 3H) ppm.

1.2 Preparation of 4-methyl-1-propyl-1,4-dihydrobenzoxazole-2-one

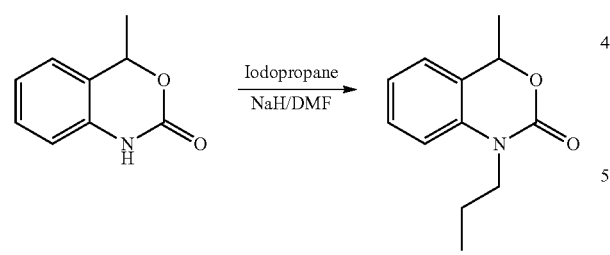

3.0 g of 4-methyl-1,4-dihydrobenzoxazole-2-one was added into 80 ml of N,N-dimethylformamide, and stirred under ice-water bath, 1.05 equivalents of sodium hydride was added in batches, after addition, the mixture was stirred for 0.5 hours. 1.05 equivalents of iodopropane were added dropwise, the ice-water bath was removed and the reaction was performed for 12 hours; the reaction was quenched by adding saturated ammonium chloride solution, and extracted with ethyl acetate. The organic phase was combined, washed with saturated aqueous sodium chloride, and the organic phase was dried over anhydrous sodium sulfate. The solvent and excess iodopropane were distilled off under reduced pressure to give 3.1 g of 4-methyl-1-propyl-1,4-dihydrobenzoxazole-2-one as an oil, which was used in the next step without further purification, and the crude yield was 85%.

1.3 Preparation of 4-methyl-6-nitro-1-propyl-1,4-dihydrobenzoxazole-2-one

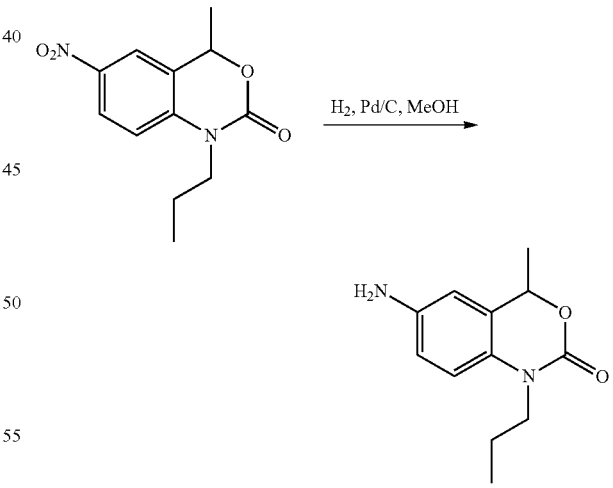

20 ml of sulfuric acid was added into a flask containing 3.0 g of 4-methyl-1-propyl-1,4-dihydrobenzoxazole-2-one under ice-water bath and stirred intensely for 0.5 hours; 1.1 equivalents of potassium nitrate in sulfuric acid solution was slowly added dropwise with a dropping funnel, the ice bath temperature was maintained and the reaction was performed for 1-2 hours; the reaction solution was poured into ice water and stirred for 0.5 h. It was filtered and the filter cake was washed with plenty of water. The crude product was recrystallized with ethanol to give 2.5 g of 4-methyl-6-nitro-1-propyl-1,4-dihydrobenzoxazole-2-one with a yield of 74%.

$^1$HNMR (400 MHz, DMSO-d$_6$): δ 8.27 (dd, 1H), 8.05 (d, 1H), 7.07 (d, 1H), 5.47 (m, 1H), 3.82 (t, 2H), 1.78 (m, 2H), 1.77 (d, 3H), 1.04 (t, 3H) ppm.

1.4 Preparation of 6-amino-4-methyl-1-propyl-1,4-dihydrobenzoxazole-2-one 1.7 g of 4-methyl-6-nitro-1-propyl-1,4-dihydrobenzoxazole-2-one was added into methanol and palladium carbon was added as a catalyst. The reaction system was recharged with hydrogen three times, and the mixture was stirred at room temperature for 8 hours. The reaction solution was filtered through a glass sand funnel charged with diatomaceous earth and the solid was removed. Purification was performed through the silica gel column chromatography to give 1.5 g of a yellow solid with a yield of 90%.

$^1$H NMR (400 MHz, DMSO-d$_6$): δ 6.77 (d, 1H), 6.60 (dd, 1H), 6.48 (d, 1H), 5.27 (m, 1H), 3.82 (t, 2H), 3.49 (s, 2H), 1.74 (m, 2H), 1.63 (d, 3H), 0.98 (t, 3H) ppm.

1.5 Preparation of 2,3,5,6-tetrafluoro-4-methylbenzylsulfonyl Chloride

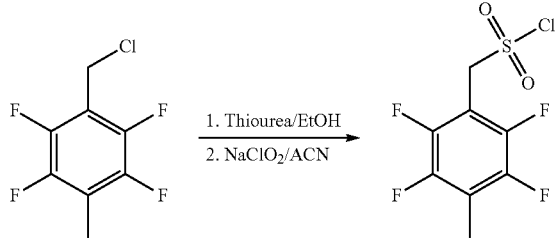 [SMILES: Cc1c(F)c(F)c(CCl)c(F)c1F ; Cc1c(F)c(F)c(CS(=O)(=O)Cl)c(F)c1F]

2,3,5,6-tetrafluoro-4-methylbenzyl chloride and 1 equivalent of thiourea were dissolved in ethanol and then the mixture was slowly heated to reflux, after the reaction was performed for 4-6 hours, the reaction solution was concentrated. Acetonitrile and concentrated hydrochloric acid were added. The temperature was controlled below 5-10° C., 3.5 equivalents of sodium chlorite were added in batches under intense stirring. The reaction was performed at 15-20° C. for 8-16 hours. The reaction was stopped by adding water and extracted with ethyl acetate for three times, and the extract liquor was concentrated to give a light yellow solid, which was used in the next step without further purification.

1.6 Preparation of Compound 0224

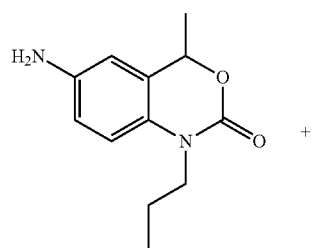

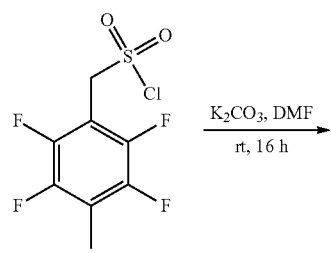

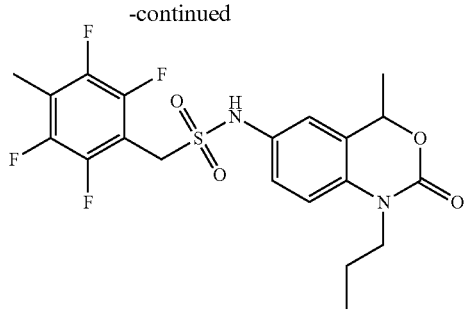

0224

1.0 g of 6-amino-4-methyl-1-propyl-1,4-dihydrobenzoxazole-2-one and 1 equivalent of 2,3,5,6-tetrafluoro-4-methylbenzylsulfonyl chloride was added into DMF and 3 equivalents of potassium carbonate was added as an acid-binding agent. The reaction was maintained at room temperature and stirred for 12-16 hours. After the reaction was completed, ice water was added and the mixture was extracted with ethyl acetate, and dried over anhydrous sodium sulfate to concentrate the organic phase. The crude product was purified with silica gel column chromatography to give 1.7 g of a light yellow solid with a yield of 75%.

$^1$HNMR (400 MHz, DMSO-d$_6$): δ10.18 (s, 1H), 7.17-7.06 (m, 3H), 5.36 (m, 1H), 4.61 (s, 2H), 3.77 (m, 2H), 2.22 (s, 3H), 1.61 (m, 2H), 1.49 (d, 3H), 0.92 (t, 3H) ppm.

Example 2 Preparation of Compound 0304

2.1 Preparation of 2-(2-aminophenyl)propan-2-ol

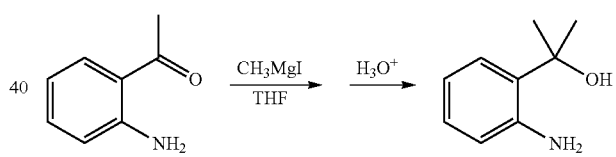

5.0 g of o-aminoacetophenone was added into 150 ml of anhydrous tetrahydrofuran and 2 equivalents of methyl magnesium iodide in tetrahydrofuran solution were added dropwise at −40 degrees Celsius. The reaction was slowly warmed to room temperature and stirred for 12 hours. The reaction was quenched by adding the saturated aqueous ammonium chloride and extracted with ethyl acetate. The mixture was dried over anhydrous sodium sulfate. The organic phase was concentrated to give 4.2 g of a yellow crude product, without further purification and the yield was 75%.

2.2 Preparation of 4,4-Dimethyl-1,4-dihydrobenzoxazole-2-one

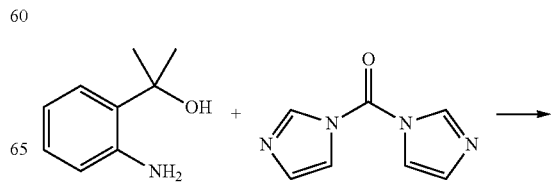

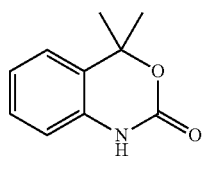

3.4 g of 2-(2-aminophenyl)-2-propanol and 5.5 g of CDI were added into 50 ml of anhydrous tetrahydrofuran and the mixture was reacted at room temperature for 12 hours; the reaction was quenched by adding 1 M HCl solution and extracted with ethyl acetate. The organic phase was combined, washed with saturated aqueous sodium chloride, and the organic phase was dried over anhydrous sodium sulfate. The solvent was distilled off under reduced pressure to give 3.7 g of a light yellow solid with a yield of 92%.

$^1$HNMR (400 MHz, CDCl$_3$): δ9.61 (s, 1H), 7.25 (m, 1H), 7.15 (d, 1H), 7.07 (m, 1H), 6.92 (dd, 1H), 1.74 (s, 6H) ppm.

2.3 Preparation of 4,4-dimethyl-1-propyl-1,4-dihydrobenzoxazole-2-one

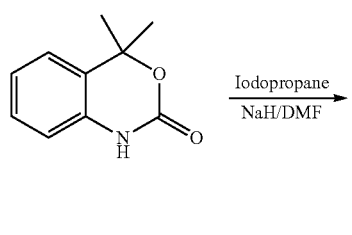

4.0 g of 4,4-dimethyl-1,4-dihydrobenzoxazole-2-one was added into 80 ml of N,N-dimethylformamide and stirred under ice bath, 1.05 equivalents of sodium hydride was added in batches. After the addition, the mixture was stirred for 0.5 hours; 1.05 equivalents of iodopropane was added dropwise, the ice-water bath was removed, and the reaction was performed for 12 hours; the reaction was quenched by adding the saturated ammonium chloride solution and extracted with ethyl acetate, and the organic phase was combined and washed with saturated sodium chloride solution, the organic phase was dried over anhydrous sodium sulfate. The solvent and excess iodopropane were distilled off under reduced pressure. Purification was performed through the silica gel column chromatography to give 2.9 g of 4,4-dimethyl-1-propyl-1,4-dihydrobenzoxazole-2-one as an oil with a yield of 60%.

$^1$HNMR (400 MHz, CDCl$_3$): δ7.33 (m, 1H), 7.20-7.18 (d, 1H), 7.10 (m, 1H), 6.96 (d, 1H), 3.91 (t, 2H), 1.76 (m, 2H), 1.71 (s, 6H), 1.02 (t, 3H) ppm.

2.4 Preparation of 4,4-dimethyl-6-nitro-1-propyl-1,4-dihydrobenzoxazole-2-one

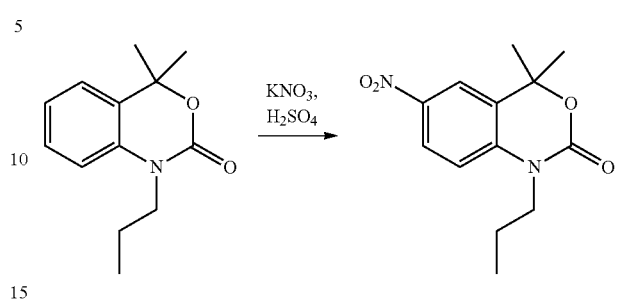

20 ml of sulfuric acid was added into a flask containing 2.0 g of 4,4-dimethyl-1-propyl-1,4-dihydrobenzoxazole-2-one under ice-water bath and stirred intensely for 0.5 hour; 1.1 equivalents of potassium nitrate in sulfuric acid solution was slowly added dropwise with a dropping funnel, the ice bath temperature was maintained and the reaction was performed for 1-2 hours; the reaction solution was poured into ice water and stirred for 0.5 hour. It was filtered and the filter cake was washed with plenty of water. The crude product was recrystallized with ethanol to give 1.8 g of 4,4-dimethyl-6-nitro-1-propyl-1,4-dihydrobenzoxazole-2-one with a yield of 78%.

$^1$HNMR (400 MHz, CDCl$_3$): δ8.25 (dd, 1H) 8.08 (d, 1H), 7.06 (d, 1H), 3.97 (t, 2H), 1.80 (m, 2H), 1.76 (s, 6H), 1.05 (t, 3H).

2.5 Preparation of 6-Amino-4,4-dimethyl-1-propyl-1,4-dihydrobenzoxazole-2-one

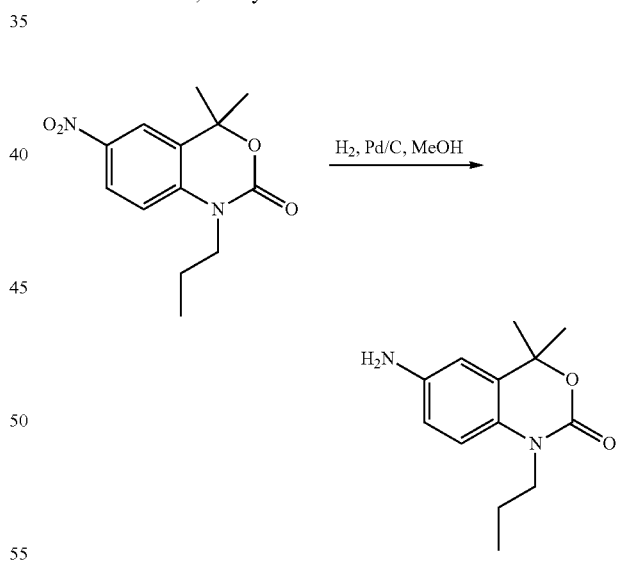

1.8 g of 4,4-dimethyl-6-nitro-1-propyl-1,4-dihydrobenzoxazole-2-one was added into 100 ml of methanol and 100 mg of palladium on carbon was added as a catalyst under a nitrogen atmosphere. The reaction system was recharged with hydrogen for three times. The mixture was stirred at room temperature for 8 hours. The reaction solution was filtered through a glass sand funnel charged with diatomaceous earth, the solid was removed and the filtrate was concentrated. Purification was performed through the silica gel column chromatography to give 1.4 g of a yellow-brown solid with a yield of 90%.

¹HNMR (400 MHz, CDCl₃): δ6.76 (d, 1H), 6.65 (dd, 1H), 6.53 (d, 1H), 3.84 (t, 2H), 3.34 (s, 2H), 1.74 (m, 2H), 1.64 (s, 6H), 0.99 (t, 3H) ppm.

2.6 Preparation of Compound 0304

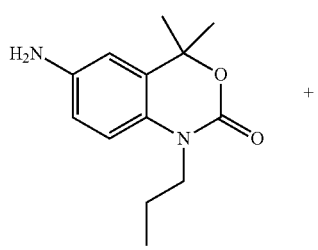

+

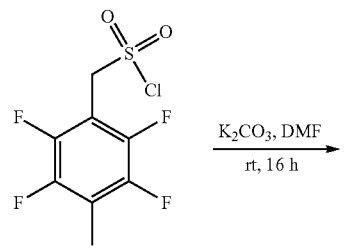

K₂CO₃, DMF
rt, 16 h

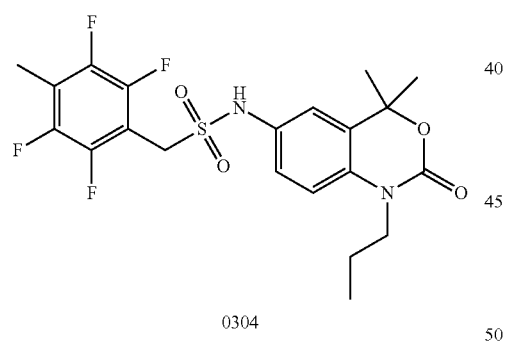

0304

0.8 g of 6-amino-4,4-dimethyl-1-propyl-1,4-dihydrobenzoxazole-2-one and 1.1 equivalents of 2,3,5,6-tetrafluoro-4-methylbenzylsulfonyl chloride was added in batches to DMF and 3 equivalents of potassium carbonate was added as an acid binding agent. The reaction was maintained at room temperature and stirred for 12-16 hours. After the reaction was completed, ice water was added, and the mixture was extracted with ethyl acetate and dried over anhydrous sodium sulfate. The organic phase was concentrated and the crude product was subjected to silica gel column chromatography to give 1.1 g of a light yellow solid with a yield of 70%.

¹HNMR (400 MHz, CDCl₃): δ7.23 (dd, 1H), 7.10 (d, 1H), 6.91 (d, 1H), 4.49 (s, 2H), 3.89 (t, 2H), 2.25 (s, 3H), 1.76 (m, 2H), 1.67 (s, 6H), 1.03 (t, 3H) ppm.

Example 3 Preparation of Compound 0706

3.1 Preparation of 4-methyl-6-nitro-1,4-dihydrobenzoxazole-2-one

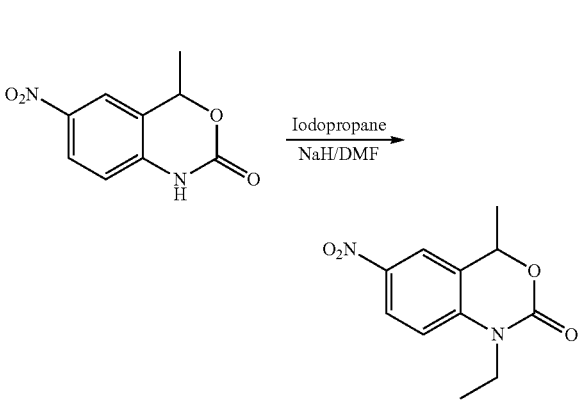

20 ml of sulfuric acid was added into a flask containing 3.0 g of 4-methyl-1,4-dihydrobenzoxazole-2-one under ice-water bath and stirred intensely for 0.5 hours; 1.1 equivalents of potassium nitrate in sulfuric acid solution was slowly added dropwise using a dropping funnel. The ice bath temperature was maintained and the reaction was performed for 1-2 hours; the reaction solution was poured into ice water and stirred for 0.5 h. It was filtered and the filter cake was washed with plenty of water. The crude product was recrystallized with ethanol to give 2.5 g of 4-methyl-6-nitro-1,4-dihydrobenzoxazole-2-one with a yield of 77%.

¹HNMR (400 MHz, DMSO-d₆): δ10.87 (s, 1H), 8.20-8.18 (d, 1H), 8.13 (s, 1H), 7.07-7.05 (d, 1H), 5.68-5.64 (m, 1H), 1.64-1.62 (d, 3H) ppm.

3.2 Preparation of 4-methyl-6-nitro-1-ethyl-1,4-dihydrobenzoxazole-2-one 3.0 g of 4-methyl-6-nitro-1,4-dihydrobenzoxazole-2-one was added into 80 ml of N,N-dimethylformamide and the mixture was stirred under ice-water bath, 1.05 equivalents of sodium hydride was added in batches, after the addition, the mixture was stirred for 0.5 h. 1.05 equivalents of iodoethane were added dropwise, the ice-water bath was removed and the reaction was performed for 12 hours; the reaction was quenched by adding saturated ammonium chloride solution, and extracted with ethyl acetate. The organic phase was combined, and washed with saturated aqueous sodium chloride, and the organic phase was dried over anhydrous sodium sulfate. The solvent and excess iodoethane were distilled off under reduced pressure to give 3.1 g of 4-methyl-6-nitro-1-ethyl-1,4-dihydrobenzoxazole-2-one. The next step was carried out without further purification and the crude yield was 85%.

3.3 Preparation of 6-amino-4-methyl-1-ethyl-1,4-dihydrobenzoxazole-2-one

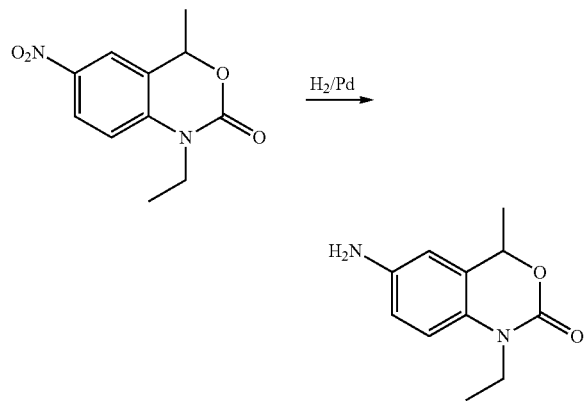

2.0 g of 4-methyl-6-nitro-1-ethyl-1,4-dihydrobenzoxazole-2-one was added into methanol and palladium carbon was added as a catalyst. The reaction system was recharged with hydrogen for three times. The mixture was stirred at room temperature for 8 hours. The reaction solution was filtered through a glass sand funnel charged with diatomaceous earth and the solid was removed to give 1.7 g of a solid. The crude product was not subjected to a further purification, and the crude field was 89%.

3.4 Preparation of Compound 0706

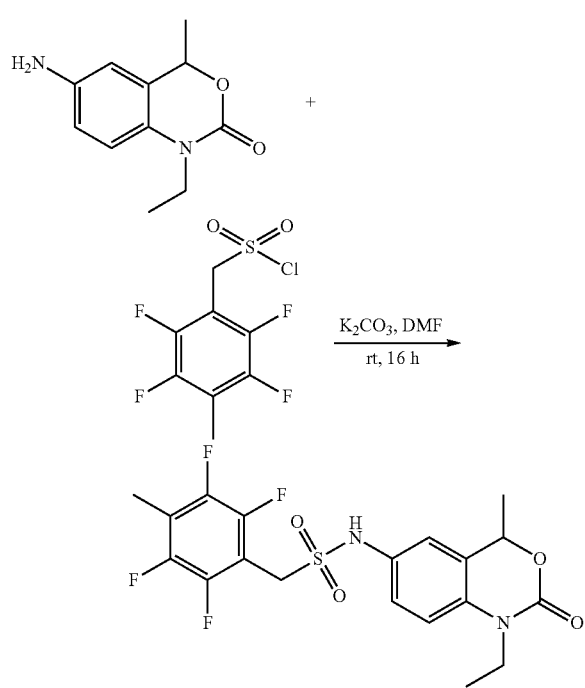

1.0 g of 6-amino-4-methyl-1-ethyl-1,4-dihydrobenzoxazole-2-one and 1 equivalent of 2,3,5,6-tetrafluoro-4-methylbenzylsulfonyl chloride was added to DMF and 3 equivalents of potassium carbonate was added as an acid-binding agent. The reaction was maintained at room temperature and the mixture was stirred for 12-16 hours. After the reaction was completed, ice water was added and the mixture was extracted with ethyl acetate and dried over anhydrous sodium sulfate and the organic phase was concentrated. The crude product was purified by silica gel column chromatography to give 1.8 g of a light yellow solid with a yield of 82%.

$^{1}$HNMR (400 MHz, DMSO-d$_6$): δ10.18 (s, 1H), 7.18-7.06 (m, 3H), 5.42 (m, 1H), 4.61 (s, 2H), 3.86 (q, 2H), 2.22 (s, 3H), 1.48 (d, 3H), 1.19 (t, 3H) ppm.

Example 4 Preparation of Compound 0708

The preparation method for the intermediate of 0708 was the same as that for 0706, except that 2-iodopropane was used instead of 1-iodoethane.

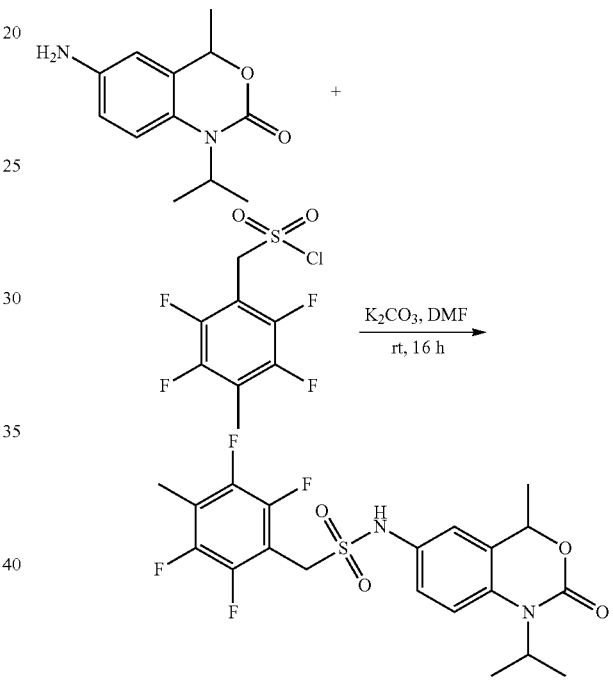

1.0 g of 6-amino-4-methyl-1-isopropyl-1,4-dihydrobenzoxazole-2-one and 1 equivalent of 2,3,5,6-tetrafluoro-4-methylbenzylsulfonyl chloride was added to DMF and 3 equivalents of potassium carbonate was added as an acid binding agent. The reaction was maintained at room temperature and the mixture was stirred for 12-16 hours. After the reaction was completed, ice water was added and the mixture was extracted with ethyl acetate and dried over anhydrous sodium sulfate and the organic phase was concentrated. The crude product was purified by silica gel column chromatography to give 1.6 g of a light yellow solid with a yield of 72%.

$^{1}$HNMR (400 MHz, DMSO-d$_6$): δ10.19 (s, 1H), 7.20-7.07 (m, 3H), 5.29 (m, 1H), 4.61 (s, 2H), 4.30 (m, 1H), 2.21 (s, 3H), 1.50-1.44 (m, 9H) ppm.

Example 5 Preparation of Compound 0713

The preparation method for the intermediate of 0713 was the same as that for 0706, except that 1-iodoisobutyl was used instead of 1-iodoethane.

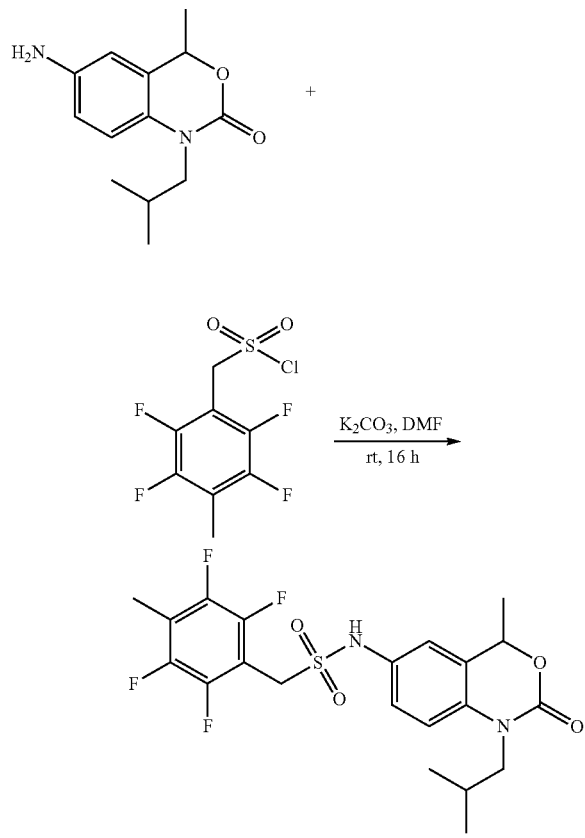

1.0 g of 6-amino-4-methyl-1-isobutyl-1,4-dihydrobenzoxazole-2-one and 1 equivalent of 2,3,5,6-tetrafluoro-4-methylbenzylsulfonyl chloride was added to DMF and 3 equivalents of potassium carbonate was added as an acid binding agent. The reaction was maintained at room temperature and stirred for 12-16 hours. After the reaction was completed, ice water was added and the mixture was extracted with ethyl acetate and was dried over anhydrous sodium sulfate and the organic phase was concentrated. The crude product was purified by silica gel column chromatography to give 1.3 g of a light yellow solid with a yield of 63%.

$^1$HNMR (400 MHz, DMSO-d6): δ10.14 (s, 1H), 7.10-7.02 (m, 3H), 5.34 (q, 1H), 4.57 (s, 2H), 3.69 (d, 2H), 2.23-2.17 (m, 4H), 1.46 (d, 3H), 0.87-0.84 (dd, 6H) ppm.

Example 6 Preparation of Compound 0715

The preparation method for the intermediate of 0715 was the same as that for 0706, except that 1-fluoro-3-iodopropane was used instead of 1-iodoethane.

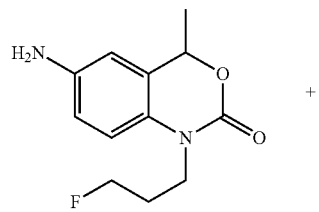

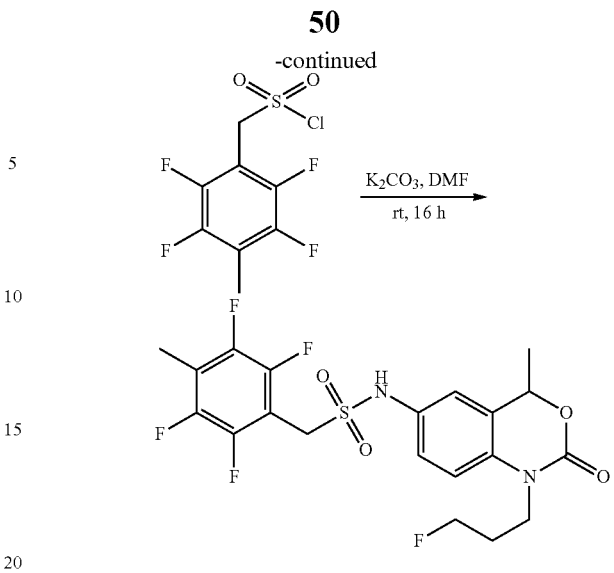

1.0 g of 6-amino-4-methyl-1-(3-fluoropropyl)-1,4-dihydrobenzoxazole-2-one and 1 equivalent of 2,3,5,6-tetrafluoro-4-methylbenzylsulfonyl chloride was added to DMF, and 3 equivalents of potassium carbonate was added as an acid binding agent. The reaction was maintained at room temperature and the mixture was stirred for 12-16 hours. After the reaction was completed, ice water was added and the mixture was extracted with ethyl acetate and dried over anhydrous sodium sulfate and the organic phase was concentrated. The crude product was purified by silica gel column chromatography to give 1.4 g of a light yellow solid with a yield of 71%.

$^1$HNMR (400 MHz, DMSO-d$_6$): δ10.19 (s, 1H), 7.18-7.06 (m, 3H), 5.42 (q, 1H), 4.61 (s, 2H), 4.61 (t, 1H), 4.50 (t, 1H), 3.95 (t, 2H), 2.22 (s, 3H), 2.06-1.94 (m, 2H), 1.51 (d, 3H) ppm.

Example 7 Preparation of Compound 0428

7.1 Preparation of 1,4-Dihydro-2H-3,1-benzoxazin-2-one

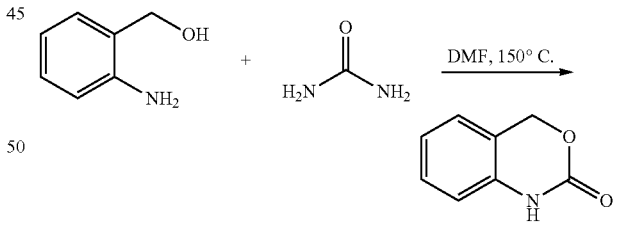

3.0 g of 2-aminobenzyl alcohol and 1.6 g of urea were added to 80 ml of DMF, and the temperature was raised to 150° C. The reaction was performed for 12 hours. The reaction was quenched by the addition of saturated sodium chloride solution, and extracted with ethyl acetate for three times. The organic phase was combined and washed with saturated aqueous sodium chloride solution and 2N hydrochloric acid to remove unreacted 2-aminobenzyl alcohol and urea. The organic phase was dried over anhydrous sodium sulfate and distilled to dry under reduced pressure to give 3.0 g of 1,4-dihydro-2H-3,1-benzoxazin-2-one. The purity detected by HPLC was 92%, and the next step was carried out without further purification. The yield was 83%.

$^1$H NMR (400 MHz, DMSO-d6): δ 5.27 (s, 2H), 6.85-7.27 (m, 4H), 10.15 (s, 1H) ppm.

7.2 Preparation of 1-propyl-1,4-dihydro-2H-3,1-benzoxazin-2-one

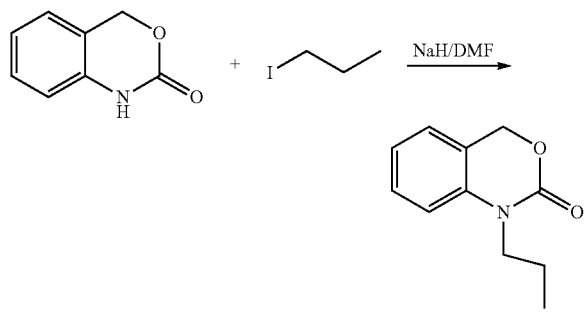

2.0 g of 1,4-dihydro-2H-3,1-benzoxazin-2-one was added to 80 ml of N,N-dimethylformamide, and 1.05 equivalents of sodium hydride was added at batches while stirred under ice-water bath. After the addition, the mixture was stirred for 0.5 hour; 1.05 equivalents of iodopropane was added dropwise, the ice-water bath was removed, and the reaction was performed for 12 hours; the reaction was quenched by adding saturated ammonium chloride solution, and extracted with ethyl acetate. The organic phase was combined, washed with saturated aqueous sodium chloride, and the organic phase was dried over anhydrous sodium sulfate. The solvent and excess iodopropane were distilled off under reduced pressure to give 2.2 g of 1-propyl-1,4-dihydro-2H-3,1-benzoxazin-2-one as an oil. The purity detected by HPLC was 92% and the next step was carried out without further purification. The yield was 88%.

7.3 Preparation of 6-nitro-1-propyl-1,4-dihydro-2H-3,1-benzoxazin-2-one

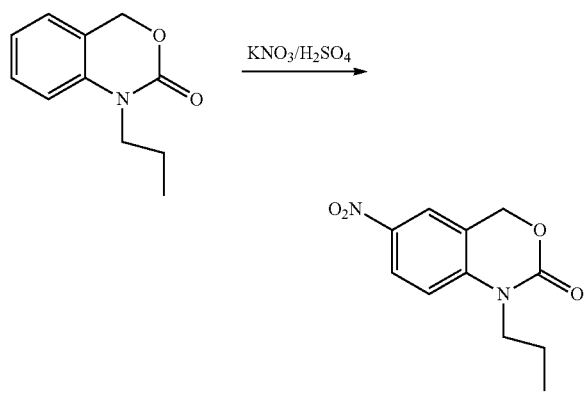

20 ml of sulfuric acid was added to a flask containing 2 g of 1-propyl-1,4-dihydro-2H-3,1-benzoxazin-2-one under ice-water bath, and stirred intensely for 0.5 h; 1.1 equivalents of potassium nitrate in sulfuric acid solution was slowly added dropwise using a dropping funnel. The ice bath temperature was maintained and the reaction was performed for 1-2 hours; the reaction solution was poured into ice water and stirred for 0.5 h. It was filtered and the filter cake was washed with plenty of water. Drying was performed under Infrared light, and the crude product was recrystallized with ethanol to give 1.8 g of 6-nitro-1-propyl-1,4-dihydro-2H-3,1-benzoxazin-2-one with a yield of 77%.

$^1$HNMR (400 MHz, DMSO-d6): δ 0.93 (t, 3H), 1.63 (m, 2H), 3.85 (t, 2H), 5.39 (s, 2H), 7.37 (m, 1H), 8.22 (m, 2H) ppm.

7.4 Preparation of 6-amino-1-propyl-1,4-dihydro-2H-3,1-benzoxazin-2-one

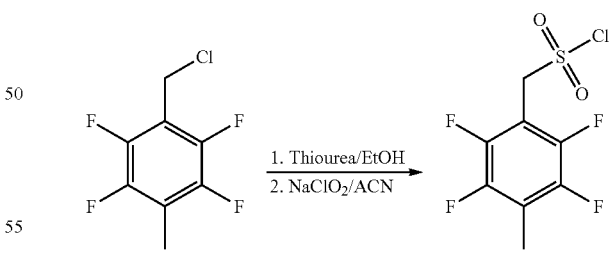

1.8 g of 6-nitro-1-propyl-1,4-dihydro-2H-3,1-benzoxazin-2-one was added to methanol, and palladium carbon was added as a catalyst. The reaction system was recharged with hydrogen for three times. The mixture was stirred at room temperature for 8 hours. The reaction solution was filtered through a glass sand funnel charged with diatomaceous earth and the solid was removed. The filtrate was concentrated to give 1.4 g of 6-amino-1-propyl-1,4-dihydro-2H-3,1-benzoxazin-2-one. The next step was carried out without further purification. The crude yield was 90%.

7.5 Preparation of 2,3,5,6-tetrafluoro-4-methylbenzylsulfonyl Chloride 1.0 g of 2,3,5,6-tetrafluoro-4-methylbenzyl chloride and 1 equivalent of thiourea were dissolved in 40 ml of ethanol and then slowly heated to reflux. After 4-6 hours of reaction, the reaction solution was concentrated to give a white solid. 10 ml of acetonitrile and 4 ml of concentrated hydrochloric acid were added. The temperature was controlled below 5-10° C., and 2.25 g of sodium chlorite was added at batches with intense stirring. The reaction was performed at 15-20° C. for 8-16 hours. The reaction was stopped by adding water and extracted with ethyl acetate for three times. The extract liquor was concentrated to give 2,3,5,6-tetrafluoro-4-methylbenzylsulfonyl chloride. The next step was carried out without further purification.

7.6 Preparation of Compound 0428

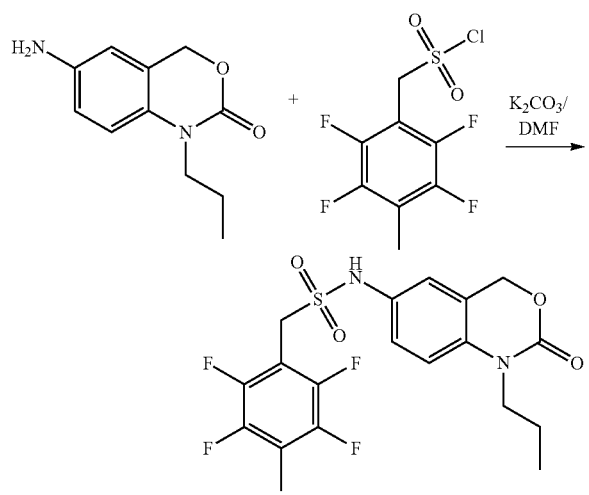

1.0 g of 6-amino-1-propyl-1,4-dihydro-2H-3,1-benzoxazin-2-one and 1.2 equivalents of 2,3,5,6-tetrafluoro-4-methylbenzylsulfonyl chloride were added to 20 ml of DMF, and 3 equivalents of potassium carbonate was added as an acid binding agent. The reaction was maintained at room temperature and stirred for 12-16 hours. After the reaction was completed, ice water was added and the mixture was extracted with ethyl acetate and dried over anhydrous sodium sulfate. The organic phase was concentrated. The crude product was subjected to silica gel column chromatography to give 1.5 g of compound 0428 with a yield of 70%.

$^1$HNMR (400 MHz, DMSO-d6): δ0.92 (t, 3H), 1.60 (m, 2H), 2.27 (s, 3H), 3.77 (t, 2H), 4.60 (s, 2H), 5.17 (s, 2H), 7.10-7.18 (m, 3H), 10.19 (s, 1H) ppm.

Example 8 Preparation of Compound 1022B

8.1 Preparation of 1-propyl-2(1H)-quinolinone

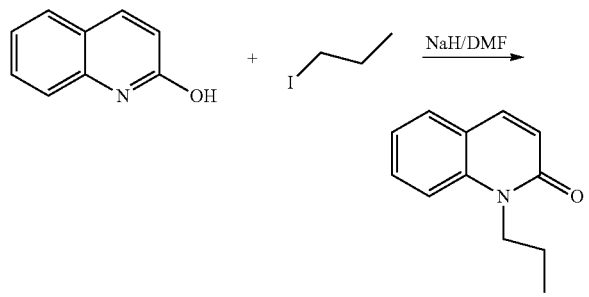

4.0 g of 2-hydroxyquinoline was added to 100 ml of DMF and stirred under ice-water bath. 1.1 equivalents of sodium hydride were added at batches. After the addition, the temperature was maintained and the mixture was stirred for 0.5 hour; 1.1 equivalents of iodopropane was added dropwise, and the ice-water bath was removed, the reaction was performed for 12 hours; the reaction was quenched with saturated ammonium chloride solution and extracted with ethyl acetate. The organic phase was combined, washed with saturated aqueous sodium chloride solution and dried over anhydrous sodium sulfate. The solvent and excess iodopropane were distilled off under reduced pressure to give an oily crude product. Separation was performed through silica gel column chromatography to give 3.3 g of 1-propyl-2(1H)-quinolinone as a colorless oily liquid with a yield of 62%.

$^1$HNMR (400 MHz, DMSO-d6): δ0.95 (t, 3H), 1.62 (m, 2H), 4.18 (t, 2H), 6.63 (d, 1H), 7.25 (t, 1H), 7.60 (m, 2H), 7.72 (d, 1H), 7.90 (d, 1H) ppm.

8.2 Preparation of 6-nitro-1-propyl-2(1H)-quinolinone

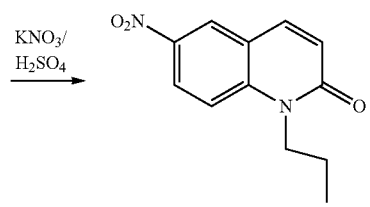

40 ml of sulfuric acid was added to a flask containing 2.0 g of 1-propyl-2(1H)-quinolinone under ice-water bath, and intensely stirred for 0.5 hour; 15 ml of 1.1 equivalents of potassium nitrate in sulfuric acid solution was slowly added dropwise with a dropping funnel. The ice bath temperature was maintained and the reaction was performed for 1-2 hours; the reaction solution was poured into ice water and stirred for 0.5 hour. It was filtered and the filter cake was washed with plenty of water. Drying was performed under infrared light. The crude product was recrystallized with ethanol to give 1.7 g of 6-nitro-1-propyl-2(1H)-quinolinone with a yield of 72%.

$^1$HNMR (400 MHz, DMSO-d6): δ0.95 (t, 3H), 1.63 (m, 2H), 4.24 (t, 2H), 6.76 (d, 1H), 7.76 (d, 1H), 8.12 (d, 1H), 8.35 (d, 1H), 8.71 (s, 1H) ppm.

8.3 Preparation of 6-amino-1-propyl-2(1H)-quinolinone

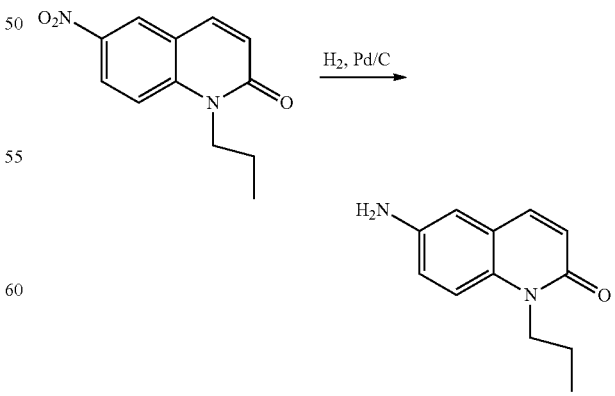

1.7 g of 6-nitro-1-propyl-2(1H)-quinolinone was added to 80 ml of methanol, and palladium carbon was added as a catalyst. The reaction system was recharged with hydrogen for three times. The mixture was stirred at room temperature for 2 hours. The reaction solution was filtered through a glass sand funnel charged with diatomaceous earth and the solid was removed. The filtrate was concentrated to give 1.4 g of 6-amino-1-propyl-2(1H)-quinolinone. The crude product was obtained without further purification and the yield was 90%.

¹HNMR (400 MHz, DMSO-d6): δ0.92 (t, 3H), 1.60 (m, 2H), 4.08 (t, 2H), 5.08 (s, 2H), 6.46 (d, 1H), 6.79 (s, 1H), 6.94 (d, 1H), 7.29 (d, 1H), 7.66 (d, 1H) ppm.

8.4 Preparation of p-methylhalobenzylsulfonyl Chloride

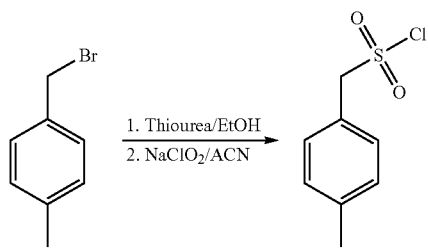

1.0 g of p-methylbenzyl bromide and 1 equivalent of thiourea were added to 40 ml of ethanol and then slowly heated to reflux and the solution turned clear. After 4-6 hours of reaction, the reaction solution was concentrated to give a white solid. 10 ml of acetonitrile and 4 ml of concentrated hydrochloric acid were added. The temperature was controlled below 5-10° C., 2.25 g of sodium chlorite was added in batches with intense stirring. The reaction was performed at 15-20° C. for 8-16 hours. The reaction was stopped by adding water and extracted with ethyl acetate for three times. The extract liquor was concentrated to give p-methylbenzylsulfonyl chloride. The crude product was used directly in the next step without purification.

8.5 Preparation of Compound 1022B

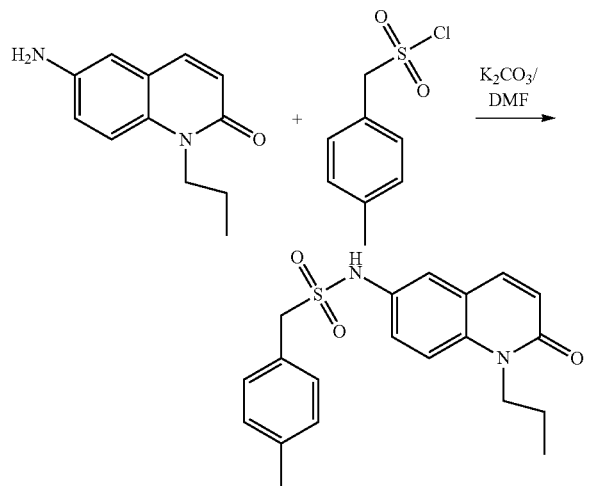

1.0 g of 6-amino-1-propyl-2(1H)-quinolinone and 1.2 equivalents of p-methylbenzylsulfonyl chloride were added to 20 ml of DMF, and 3 equivalents of potassium carbonate was added as an acid binding agent. The reaction was maintained at room temperature and stirred for 12-16 hours. After that, ice water was added and the mixture was extracted with ethyl acetate for three times and the organic phase was combined and dried over anhydrous sodium sulfate. The organic phase was concentrated and the crude product was subjected to silica gel column chromatography to give 1.3 g of compound 1022B with a yield of 70%.

¹HNMR (400 MHz, DMSO-d6): δ 0.95 (t, 3H), 1.62 (m, 2H), 2.27 (s, 3H), 4.18 (t, 2H), 4.42 (s, 2H), 6.60 (d, 1H), 7.12-7.17 (m, 4H), 7.40 (d, 1H), 7.45 (s, 1H), 7.55 (d, 1H), 7.83 (d, 1H) ppm; ¹³CNMR (100 MHz, DMSO-d6) δ 11.53, 20.99, 21.54, 43.35, 57.34, 116.08, 119.20, 121.17, 122.14, 124.01, 126.89, 129.46, 131.34, 133.02, 135.97, 138.12, 139.45, 161.12 ppm.

Example 9 Preparation of Compound NC0F4

9.1 Preparation of 2-aminomethyl-4-nitroaniline

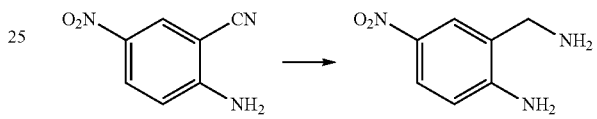

5.0 g of 2-cyano-4-nitroaniline was added to 200 ml of dry tetrahydrofuran, and 3.5 equivalents of borane tetrahydrofuran solution was added dropwise and stirred under ice-water bath. After the addition, the mixture was stirred at room temperature overnight; the reaction was quenched by slowly dropwise adding the saturated ammonium chloride solution. The mixture was extracted by adding dichloromethane. The organic phase was combined, washed with saturated aqueous sodium chloride, and the organic phase was dried over anhydrous sodium sulfate. The solvent and excess iodopropane were distilled off under reduced pressure to give 4.2 g of 2-aminomethyl-4-nitroaniline with a yield of 83%.

¹HNMR (400 MHz, DMSO-d6): δ8.05 (d, 1H), 7.88 (dd, 1H), 6.70-6.59 (m, 3H), 3.63 (s, 2H) ppm.

9.2 Preparation of 6-nitro-3,4-dihydroquinazoline-2(1H)-one

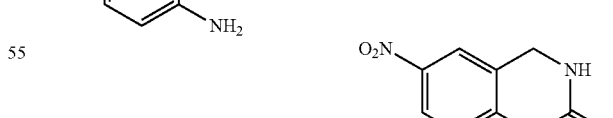

4.5 g of 2-aminomethyl-4-nitroaniline was added to 250 ml of dry tetrahydrofuran and 1.5 equivalents of CDI were added under stirring. After the addition, the mixture was warmed to reflux and stirred overnight; tetrahydrofuran was distilled off under reduced pressure and the mixture was extracted with water and dichloromethane. The organic phase was combined, washed with saturated aqueous sodium chloride, and the organic phase was dried over anhydrous sodium sulfate to give 6-Nitro-3,4-dihydroquinazoline-2(1H)-one with a yield of 74%.

¹HNMR (400 MHz, DMSO-d6): δ9.78 (s, 1H), 8.07 (s, 1H), 8.04 (m, 1H), 7.17 (d, 1H), 6.93 (d, 1H), 4.43 (s, 2H) ppm.

9.3 Preparation of 1-propyl-6-nitro-3,4-dihydroquinazoline-2(1H)-one

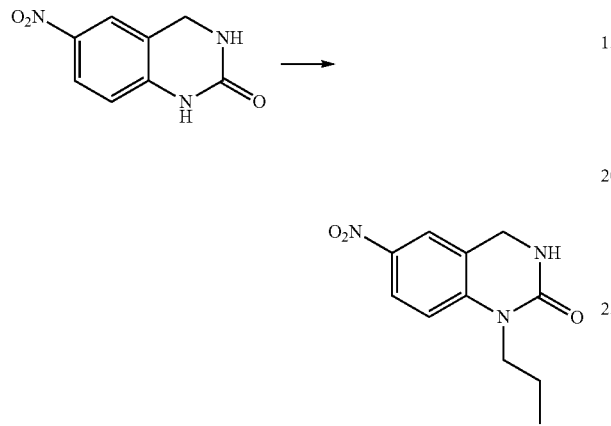

The synthesis method is the same as that in Example 7.2, except that 6-nitro-3,4-dihydroquinazoline-2(1H)-one is used instead of 1,4-dihydro-2H-3,1-benzoxazine-2-ketone. The crude product was directly subjected to the next step without further purification, and the crude yield was 56%.

9.4 Preparation of 1-propyl-6-amino-3,4-dihydroquinazoline-2(1H)-one

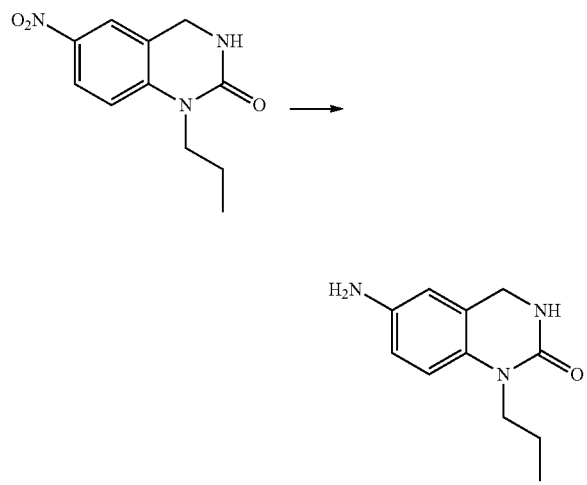 [SMILES: CCCN1C(=O)NCc2cc([N+](=O)[O-])ccc21 ; CCCN1C(=O)NCc2cc(N)ccc21]

The synthesis method is the same as that in Example 7.4, except that 1-propyl-6-nitro-3,4-dihydroquinazoline-2(1H)-one is used instead of 6-nitro-1-propyl 1,4-dihydro-2H-3,1-benzoxazine-2-one. The crude product was not subjected to a further purification, crude yield was 87%.

9.5 Preparation of NC0F4

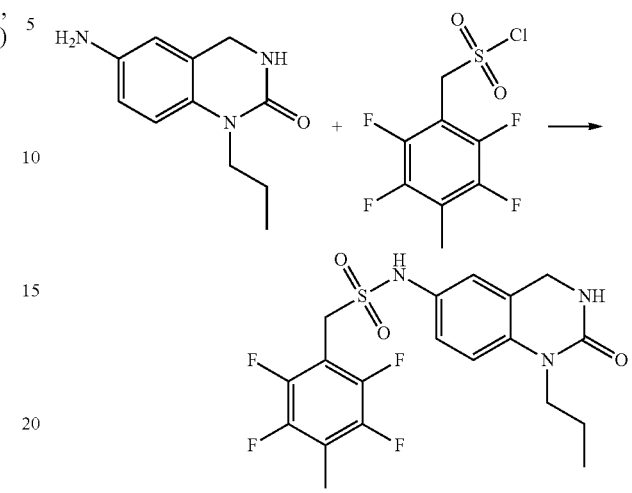

The synthesis method is the same as that in Example 7.6, except that 1-propyl-6-amino-3,4-dihydroquinazoline-2 (1H)-one is used instead of 6-amino-1-propyl-1,4-dihydro-2H-3,1-benzoxazine-2-one.

¹HNMR (400 MHz, DMSO-d6): δ10.0 (s, 1H), 7.06-6.90 (m, 4H), 4.56 (s, 2H), 4.20 (s, 2H), 3.69 (s, 2H), 2.24 (s, 3H), 1.52 (m, 2H), 0.89 (t, 3H) ppm.

Example 10 Preparation of Compound 1028c

10.1 Preparation of N-(1-(2-aminophenyl)ethylidene)-t-butylsulfinic Acid Amine

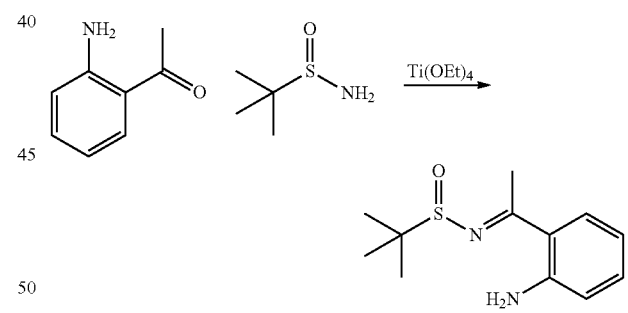

2.0 g of 2-aminoacetophenone and 1 equivalent of tert-butylsulfinamide were added to 2 equivalents of tetraethyl titanate, nitrogen was filled and the tube was sealed and heated to 75° C. and the mixture was stirred for 16 hours and cooled to room temperature, and poured into iced brine, the reaction was quenched and extracted with ethyl acetate. The organic phase was combined, washed with saturated aqueous sodium chloride solution and dried over anhydrous sodium sulfate. The organic phase was concentrated under reduced pressure, and purified by silica gel column chromatography to give 2.7 g of a light yellow solid with a yield of 74%.

¹HNMR (400 MHz, DMSO-d₆): δ 7.66 (d, 1H), 7.43 (s, 2H), 7.20 (t, 1H), 6.75 (d, 1H), 6.58 (t, 1H), 2.68 (s, 3H), 1.18 (s, 9H) ppm.

10.2 Preparation of N-(1-(2-aminophenyl)ethyl)-t-butylsulfinic Acid Amine

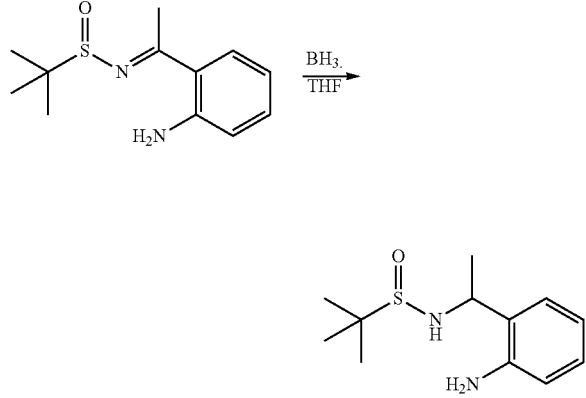

2.5 g of N-(1-(2-aminophenyl)ethylidene) t-butylsulfinic acid amine was dissolved in absolute anhydrous tetrahydrofuran, the solution was controlled at −78° C., and borane dimethyl sulfide complex in tetrahydrofuran solution was slowly added dropwise under a nitrogen atmosphere. After the addition, the mixture was stirred for 3 hours; the reaction was quenched by dropwise adding the saturated brine, and extracted with ethyl acetate. The organic phase was combined, washed with saturated aqueous sodium chloride, and the organic phase was dried over anhydrous sodium sulfate, and concentrated under reduced pressure and purified by silica gel column chromatography to give 2.3 g of a light yellow solid with a yield of 91%.

$^1$HNMR (400 MHz, DMSO-$d_6$): δ 7.16 (d, 1H), 6.96 (t, 1H), 6.64 (d, 1H), 6.56 (t, 1H), 5.37 (d, 1H), 4.95 (s, 2H), 4.40 (m, 1H), 4.14 (d, 3H) 1.11 (s, 9H) ppm.

10.3 Preparation of 2-(1-aminoethyl)aniline

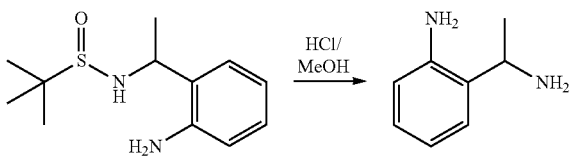

2.2 g of N-(1-(2-aminophenyl)ethyl)-t-butylsulfinic acid amine was dissolved in methanol and 4 M hydrochloric acid (1:1), and the solution was stirred overnight; and concentrated under reduced pressure, and the pH was adjusted to alkaline. The extracted reaction was performed by adding saturated brine/ethyl acetate. The organic phase was combined, washed with saturated aqueous sodium chloride, and the organic phase was dried over anhydrous sodium sulfate, and concentrated under reduced pressure to give 1.2 g product with a yield of 91%.

$^1$HNMR (400 MHz, DMSO-d6): δ 7.05 (d, 1H), 6.89 (t, 1H), 6.56 (d, 1H), 6.50 (t, 1H), 5.27 (s, 2H), 4.03 (q, 1H), 3.37 (in water peak) 1.27 (d, 3H) ppm.

10.4 Preparation of 4-methyl-3,4-dihydroquinazoline-2(1H)-one

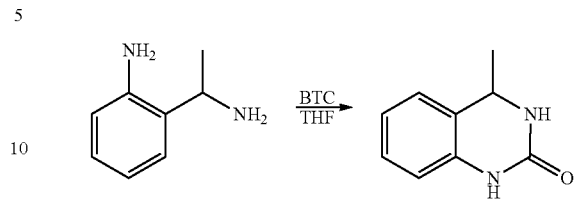

1.2 g of 2-(1-aminoethyl)aniline was dissolved into 70 ml of anhydrous tetrahydrofuran, 1.2 equivalents of triphosgene (BTC) was added in batches and the reaction was performed at room temperature for 12 hours; the reaction was quenched by adding 1 M HCl solution and extracted with ethyl acetate. The organic phase was combined, washed with saturated aqueous sodium chloride solution and dried over anhydrous sodium sulfate. The solvent was distilled off under reduced pressure to give 1.2 g of a light yellow solid with a yield of 82%.

$^1$HNMR (400 MHz, DMSO-$d_6$): δ 9.06 (s, 1H), 7.12-6.84 (m, 4H), 6.77 (d, 1H), 4.45 (m, 1H), 1.31 (d, 3H) ppm.

10.5 Preparation of 4-methyl-1-propyl-1,4-dihydroquinazoline-2(1H)-one

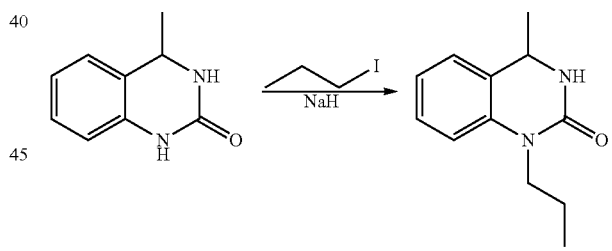

1.2 g of 4-methyl-3,4-dihydroquinazoline-2(1H)-one was added to 80 ml of N,N-dimethylformamide, and 1.05 equivalents of sodium hydride was added in batches and stirred under ice-water bath. After the addition, the mixture was stirred for 0.5 h; 1.05 equivalents of iodopropane was added dropwise, the ice-water bath was removed, and the reaction was performed for 12 hours; the reaction was quenched by adding the saturated ammonium chloride solution and extracted with ethyl acetate, and the organic phase was combined and washed with saturated sodium chloride solution. The organic phase was dried over anhydrous sodium sulfate. The solvent and excess iodopropane were distilled off under reduced pressure to give 1.4 g of oily product, which was not subjected to a further purification, and the yield was 92%.

10.6 Preparation of 4-methyl-6-nitro-1-propyl-1,4-dihydroquinazoline-2(1H)-one

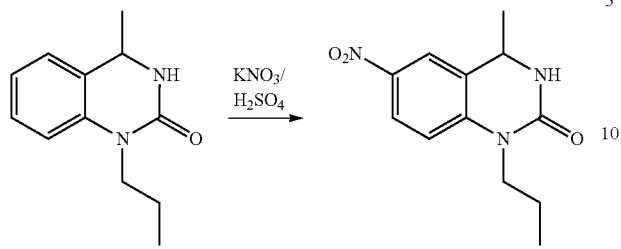

20 ml of sulfuric acid was added to a flask containing 1.2 g of 4-methyl-1-propyl-3,4-dihydroquinazoline-2(1H)-one under ice bath and the mixture was stirred intensely for 0.5 hours; 1.1 equivalents of potassium nitrate in sulfuric acid solution was slowly added dropwise through a dropping funnel, the ice bath temperature was maintained and the reaction was performed for 1-2 hours; the reaction solution was poured into ice water and stirred for 0.5 hours. It was filtered and the filter cake was washed with plenty of water. The crude product was recrystallized with ethanol to give 1.1 g of 4-methyl-6-nitro-1-propyl-1,4-dihydroquinazoline-2(1H)-one with a yield of 72%.

$^1$HNMR (400 MHz, DMSO-d$_6$): δ8.11 (dd, 1H) 8.10 (s, 1H), 7.54 (d, J=1.6 Hz, 1H), 7.18 (d, J=8.8 Hz, 1H), 4.62 (m, 1H), 3.81 (m, 2H), 1.55 (m, 2H), 1.33 (d, 3H), 0.90 (t, 3H) ppm.

10.7 Preparation of 6-amino-4-methyl-1-propyl-1,4-dihydroquinazoline-2(1H)-one

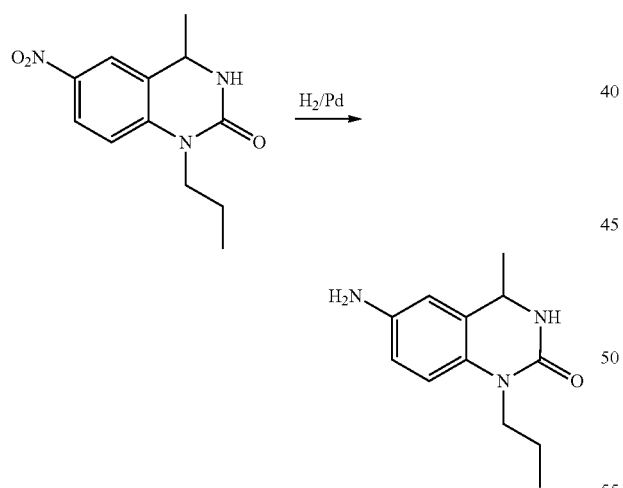

1.1 g of 4-methyl-6-nitro-1-propyl-1,4-dihydroquinazoline-2(1H)-one was added to 100 ml of methanol, and 40 mg of palladium carbon was added as a catalyst under a nitrogen atmosphere. The reaction system was recharged with hydrogen for three times. The mixture was stirred at room temperature for 8 hours. The reaction solution was filtered through a glass sand funnel charged with diatomaceous earth and the solid was removed and the filtrate was concentrated. Purification was performed through the silica gel column chromatography to give 1.2 g of a yellow-brown solid with a yield of 93%.

$^1$H NMR (400 MHz, DMSO-d6): δ6.75 (s, 1H), 6.65 (d, J=8.8 Hz, 1H), 6.46 (dd, 1H), 6.37 (d, J=2.0 Hz, 1H), 4.75 (s, 2H), 4.26 (m, 1H), 3.67 (m, 2H), 1.51 (m, 2H), 1.25 (d, J=6.4 Hz, 3H) 0.86 (t, J=7.2 Hz, 3H) ppm.

10.8 Preparation of 1028c

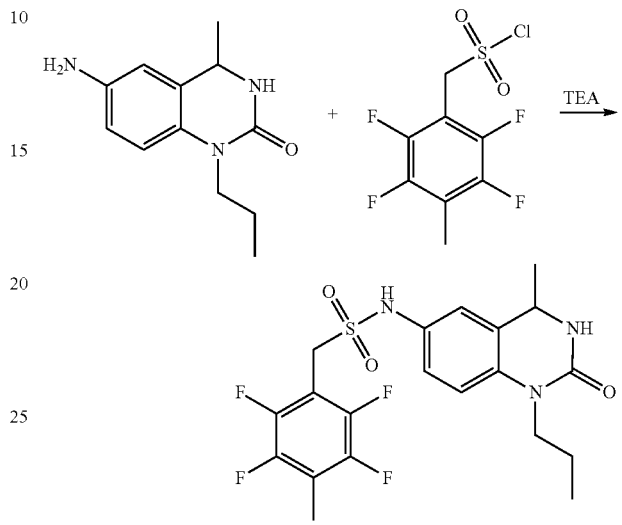

1.0 g of 6-amino-4-methyl-1-propyl-1,4-dihydroquinazoline-2(1H)-one and 1.1 equivalents of 2,3,5,6-tetrafluoro-4-methylbenzylsulfonyl chloride was added in batches to DMF and 3 equivalents of triethylamine (TEA) was added as an acid binding agent. The reaction was maintained at room temperature and the mixture was stirred for 12-16 hours. After the reaction was completed, ice water was added, and the mixture was extracted with ethyl acetate and dried over anhydrous sodium sulfate. The organic phase was concentrated and the crude product was subjected to silica gel column chromatography to give 1.1 g of a light yellow solid with a yield of 70%.

$^1$HNMR (400 MHz, DMSO-d$_6$): δ10.0 (s, 1H), 7.07-7.04 (m, 2H), 6.98 (d, J=2.4 Hz, 1H), 6.92 (d, J=8.8 Hz, 1H), 4.56 (s, 2H), 4.35 (m, 1H), 3.75 (m, 2H), 3.03 (s, 3H), 1.52 (m, 2H), 1.25 (d, J=6.4 Hz, 3H), 0.87 (t, J=7.2 Hz, 3H) ppm.

Example 11 In-Vitro Assay on Activity of Compound 0224, 0304, 0706, 0708, 0713, 0715, 1028c, 0428, 1022B and NC0F4

In-vitro biochemical experiments suggested that a multiple of compounds of the present invention, as the efficient PYL receptor agonists, had high binding affinities to a plurality of PYL receptors and promoted the bind of PYL receptors and inhibited the activity of PP2C protein phosphatase.

11.1 In-Vitro Biochemical Experiments and PP2C Protein Phosphatase Activity Test The results were shown in FIG. 1a-1g. The experiment of activity of HAB1 protein phosphatase, wherein a SnRK2.6 phosphorylated polypeptide was used as a substrate, showed that all of the compounds 0224, 0304, 0706, 0708, 0713, 0715, 1028c, 0428, 1022B and NC0F4 could promote the binding between PYL2 receptor and PP2C protein phosphatase (HAB1), thus inhibiting the dephosphorylation effect of HAB1 on SnRK2.6 phosphorylated polypeptide. Further, at a low concentration, the effect of most compounds was better or significantly better than that of ABA at the same concentration.

11.2 AlphaScreen Experiment

AlphaScreen technology was used to test the ability of the compounds of the present invention to promote PYL receptor binding to PP2C protein phosphatase (HAB1).

Figure 1:
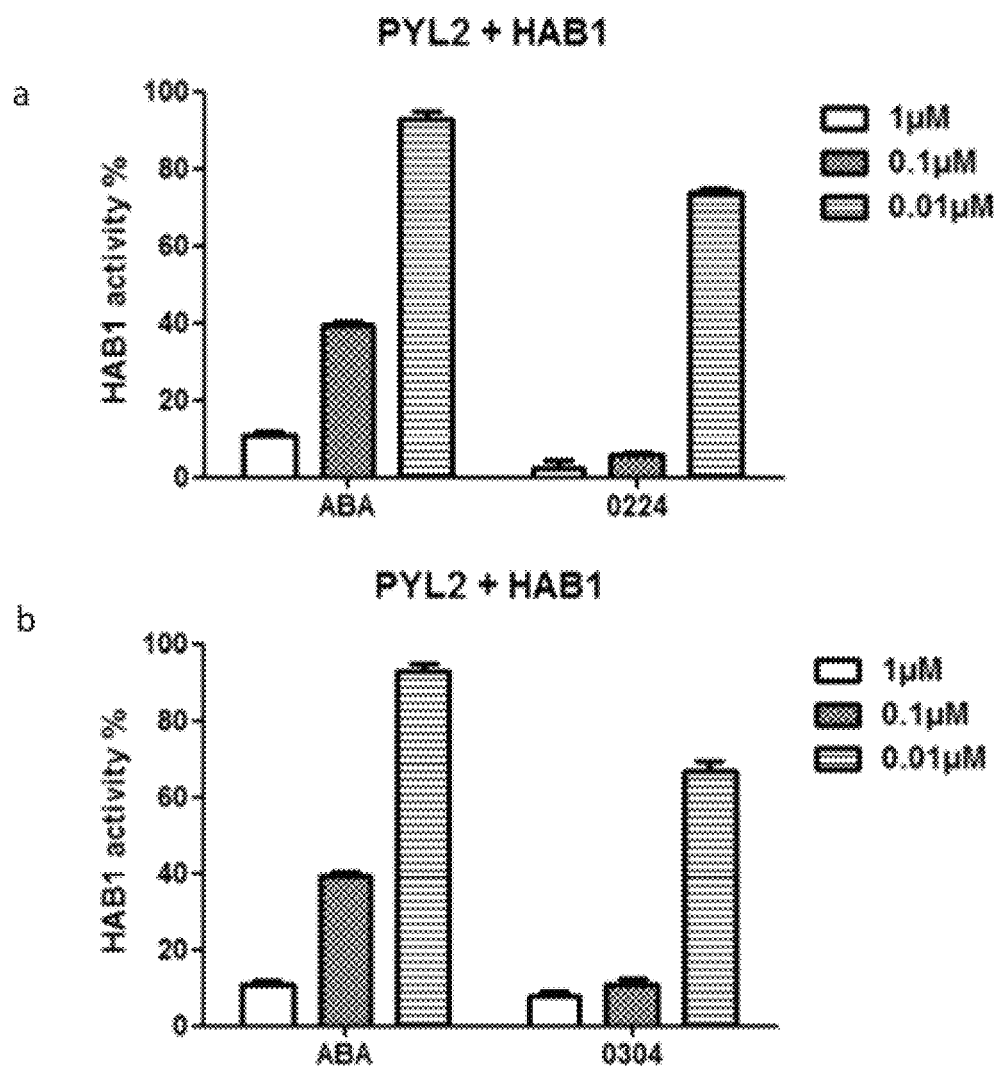
FIG. 1 shows multiple compounds of the present invention, including 0224 (FIG. 1a), 0304 (FIG. 1b), 0706, 0708, 0713, 0715 (FIG. 1c), 1028c (FIG. 1d), 0428 (1e), 1022B (1f) and NC0F4 (1g) can bind to a PYL2 receptor-HAB1 complex of *Arabidopsis thaliana*, thereby inhibiting the activity of protein phosphatase HAB1. At lower concentrations, all of the above compounds exhibit inhibitory effects, and the inhibitory effects of most compounds are better or significantly better than that of ABA.
Figure 1:
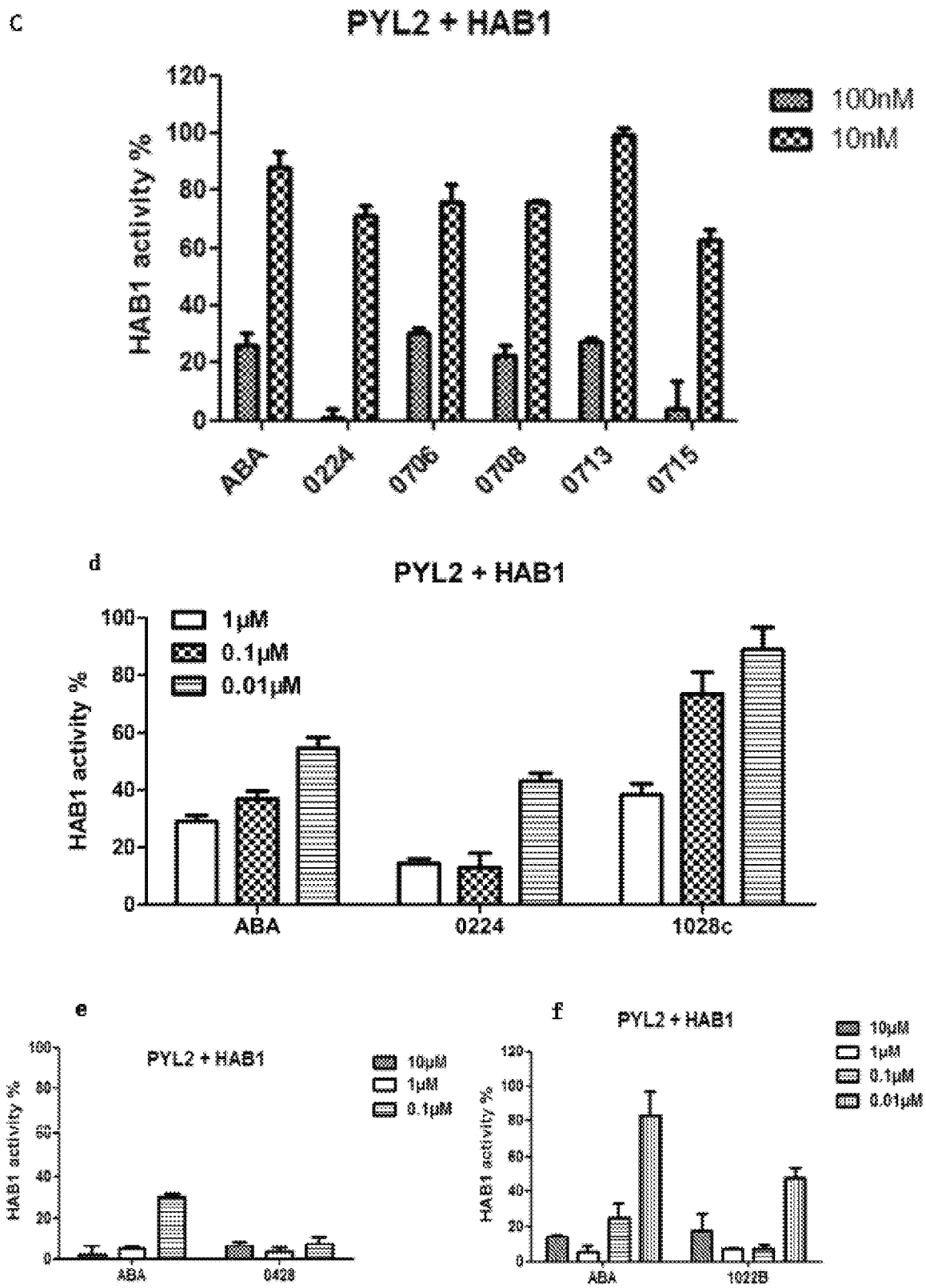
Figure 1:
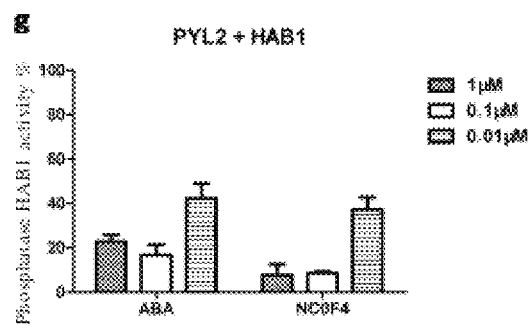
Figure 2:
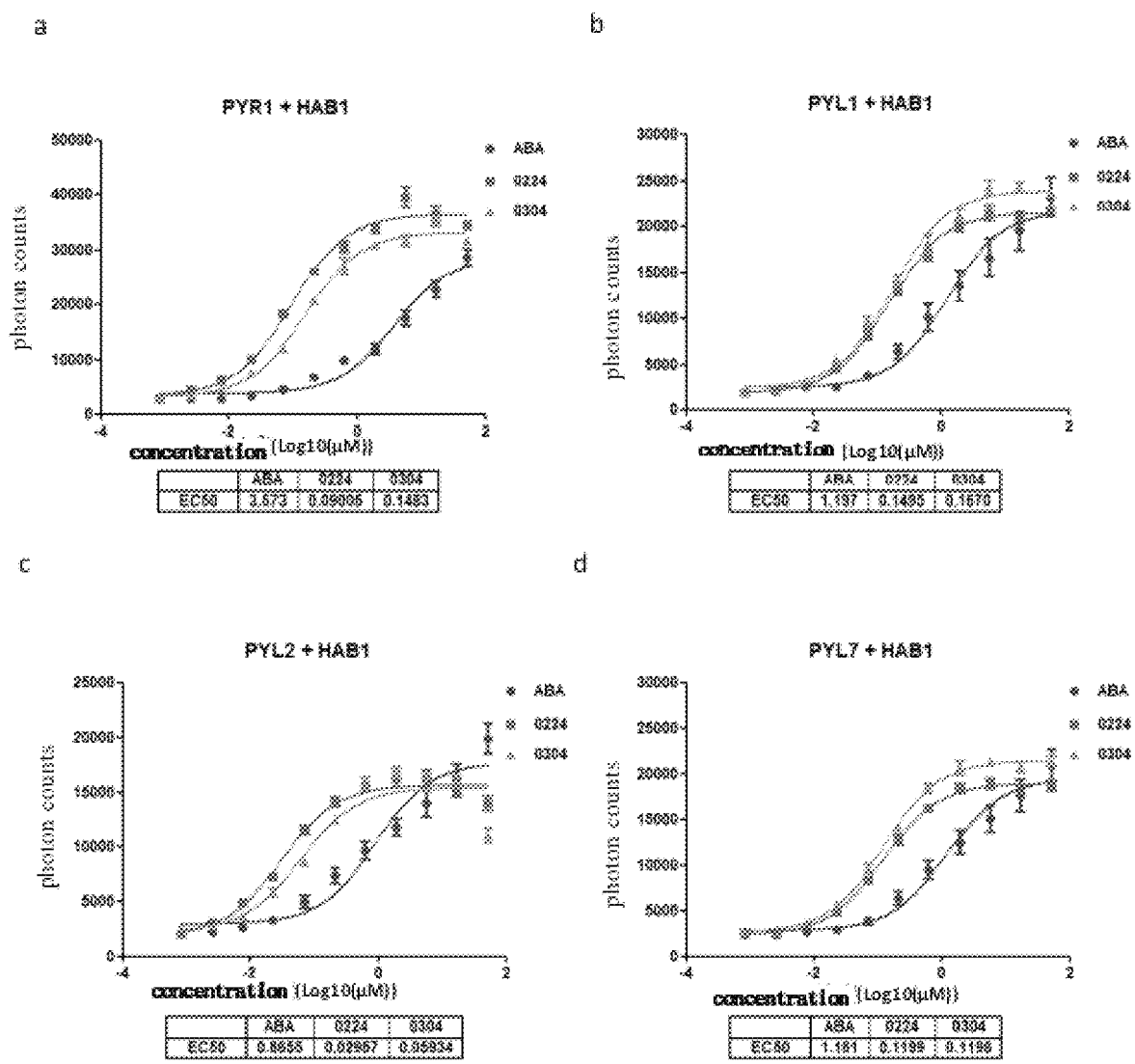
FIG. 2 shows a multiple of compounds of the present invention exhibit a dose-dependent effect as a PYL receptor agonist. Wherein a dose response curve of 0224 and 0304 with PYR1 (FIG. 2a), PYL1 (FIG. 2b), PYL2 (FIG. 2c) and PYL7 (FIG. 2d) receptors of *Arabidopsis thaliana*, and dose response curves of four compounds (0706, 0708, 0713 and 0715) (FIG. 2e), compounds 0428 (FIG. 2f), 1022B (FIG. 2g) and NCOF (FIG. 2h) with a receptor agonist of PYL2 receptor of *Arabidopsis thaliana* show that the compounds as described above can promote the interaction of protein phosphatase HAB1 and the PYL receptors of *Arabidopsis thaliana*, and the interaction exhibit a dose-dependent effect. The $EC_{50}$ values show that the affinity of the above compounds with the corresponding receptors is significantly higher than that of ABA.
Figure 2:
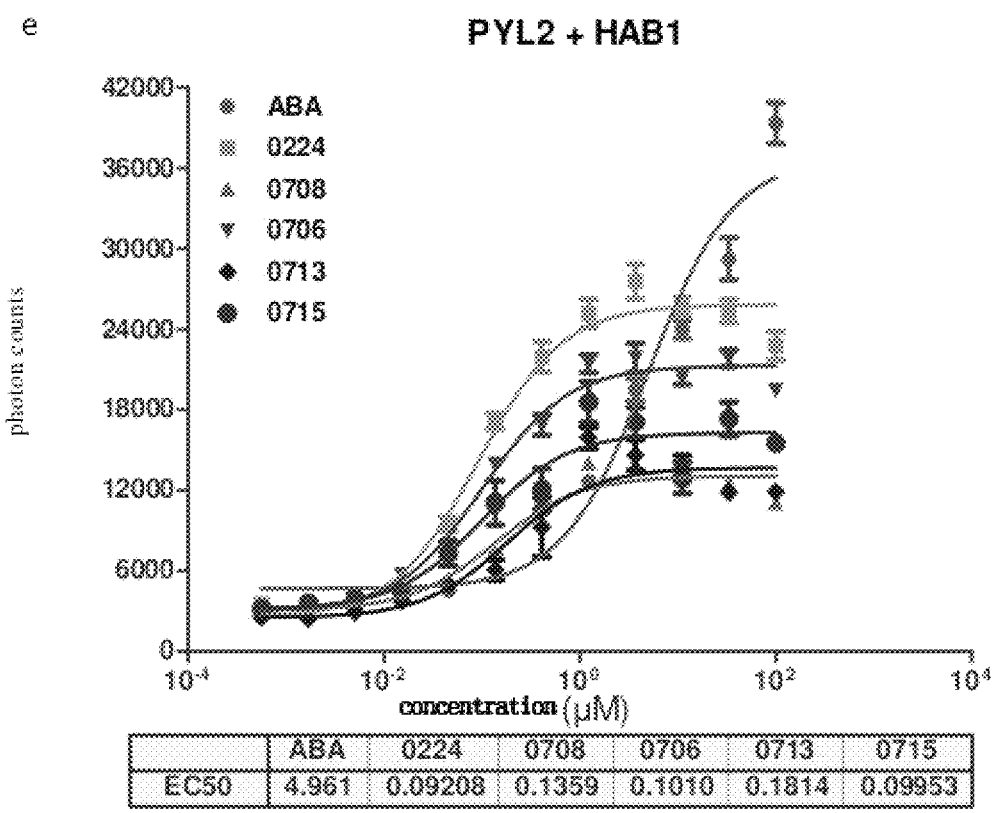
Figure 2:
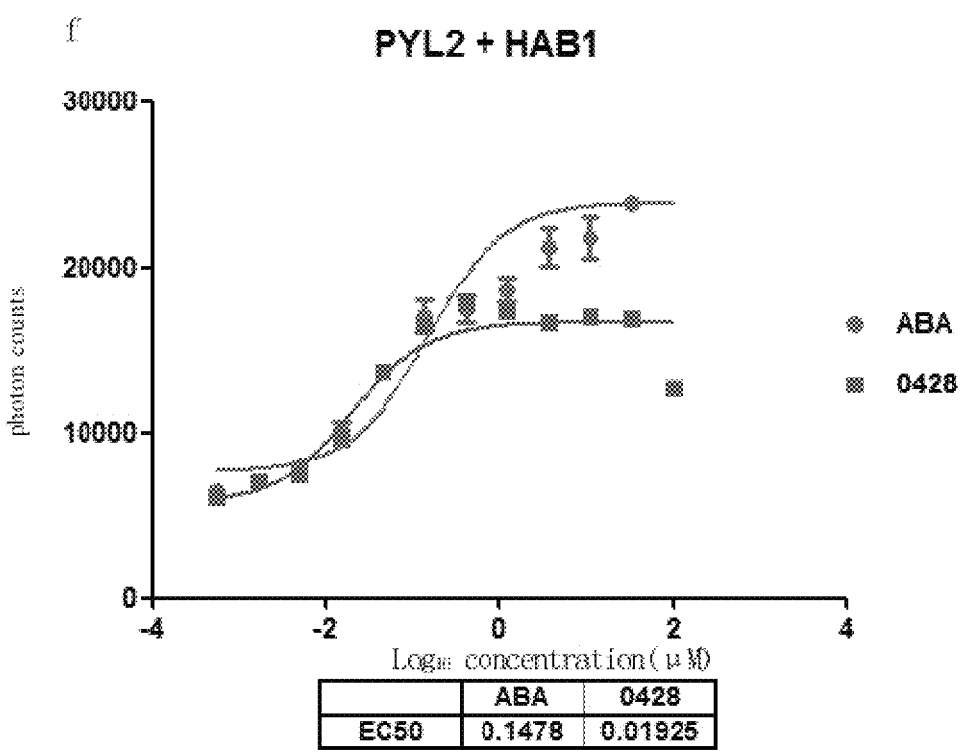
Figure 2:
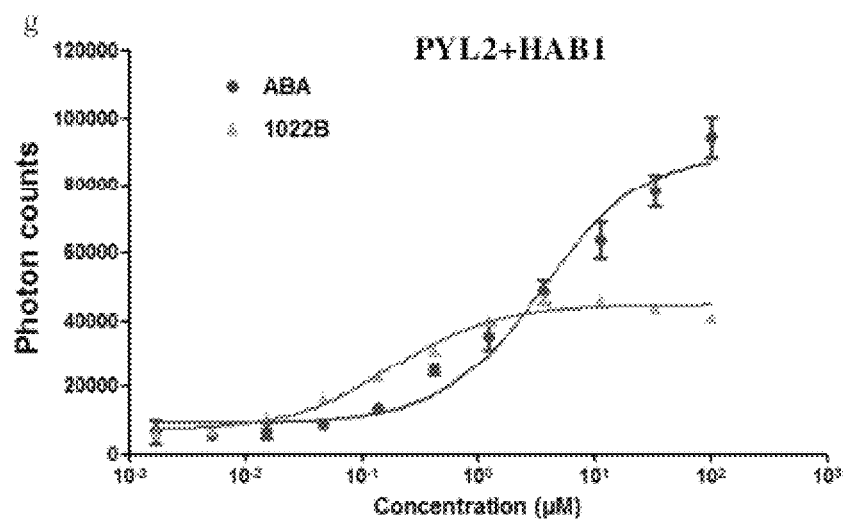
Figure 2:
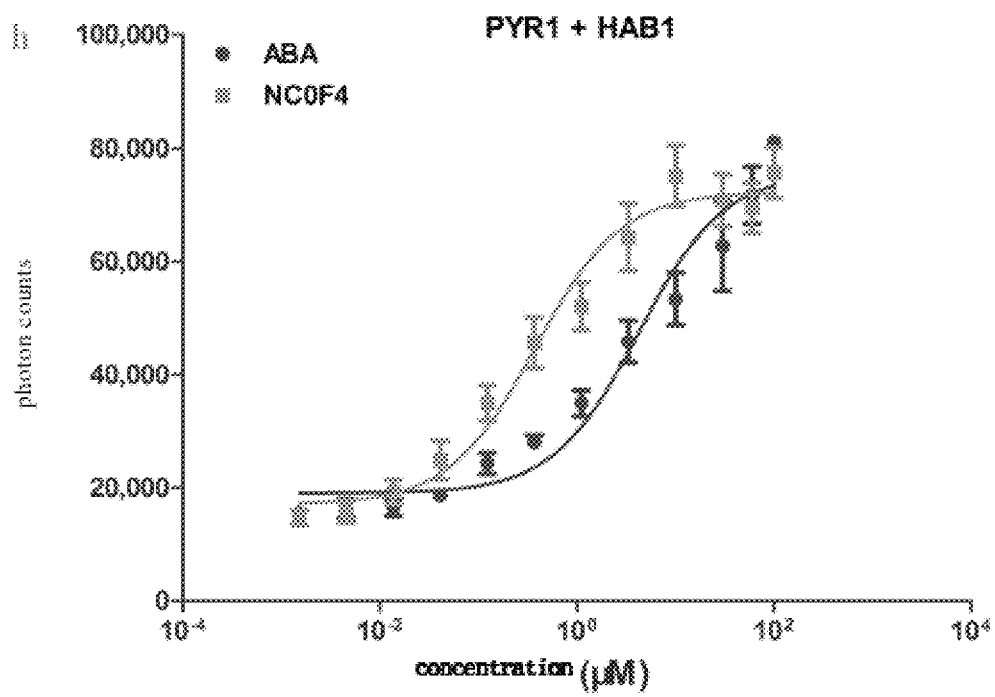

Experimental results showed that there was a dose-dependent effect of compounds 0224 and 0304 on the binding ability of the PYL receptors-HAB1 protein phosphatase complex. For Arabidopsis PYR1, PYL1, PYL2, PYL7 receptor, both of the compounds 0224 and 0304 had significantly better affinity for receptors than ABA, wherein the $EC_{50}$ value of 0224 and 0304 with PYR1 receptor-HAB1 protein phosphatase complex was 1/40 and 1/24 of ABA, respectively (FIG. 2a), the $EC_{50}$ value of 0224 and 0304 with PYL1 receptor-HAB1 protein phosphatase complex was 1/8 and 1/7 of ABA, respectively (FIG. 2b), the $EC_{50}$ value of 0224 and 0304 with PYL2 receptor-HAB1 protein phosphatase complex was 1/29 and 1/15 of ABA, respectively (FIG. 2c), the $EC_{50}$ value of 0224 and 0304 with PYL7 receptor-HAB1 protein phosphatase complex was 1/10 of ABA (FIG. 2d). The compounds 0706, 0708, 0713, 0715, 0428, 1022B and NC0F4 also showed better PYL2 receptor affinity over ABA, wherein the $EC_{50}$ value of 0706, 0708, 0713, and 0715 was approximately 1/5-1/8 of ABA (FIG. 2e). The $EC_{50}$ value of compound 0428 was about 1/8 of that of ABA (FIG. 2f), the $EC_{50}$ value of 1022B was one order of magnitude lower than that of ABA (FIG. 2g), and the binding ability of PYL2 receptor to HAB1 has a dose-dependent effect with the above compounds. Compound NC0F4 showed better PYR1 receptor affinity over ABA with an $EC_{50}$ value of about 1/11 of ABA (FIG. 2h).

The above results suggested that the compounds 0224, 0304, 0706, 0708, 0713, 0715, 1028c, 0428, 1022B and NC0F4 were the PYL receptor agonists that more efficient than ABA.

In addition, experiments using soybean GmPYL6 (homologous gene for Arabidopsis PYL2) and rice OsPYL2 (homologous gene for Arabidopsis PYL2) and Arabidopsis AtHAB1 showed that compound 0428 also had significantly higher affinities for soybean GmPYL6 protein and rice OsPYL2 protein than that of ABA, and the $EC_{50}$ value was only about 1/14 and 1/3 of ABA, respectively.

The above results suggested that the above multiple of compounds of the present invention were a series of PYL receptor agonists that more efficient than existing compounds such as ABA.

In addition, when the concentrations of other compounds of the present invention tested in vitro ranged from 0.01 to 100 μM, the compounds of the present invention all exhibited significant affinity for PYR/PYL receptor.

Example 12 Germination Inhibition and Drought Resistance Activity Test for a Plurality of Compounds of the Present Invention (Such as 0428, 0224, 0304, 0706, 0715, Etc.)

12.1 Inhibition Effect on Arabidopsis Seed Germination

Figure 3:
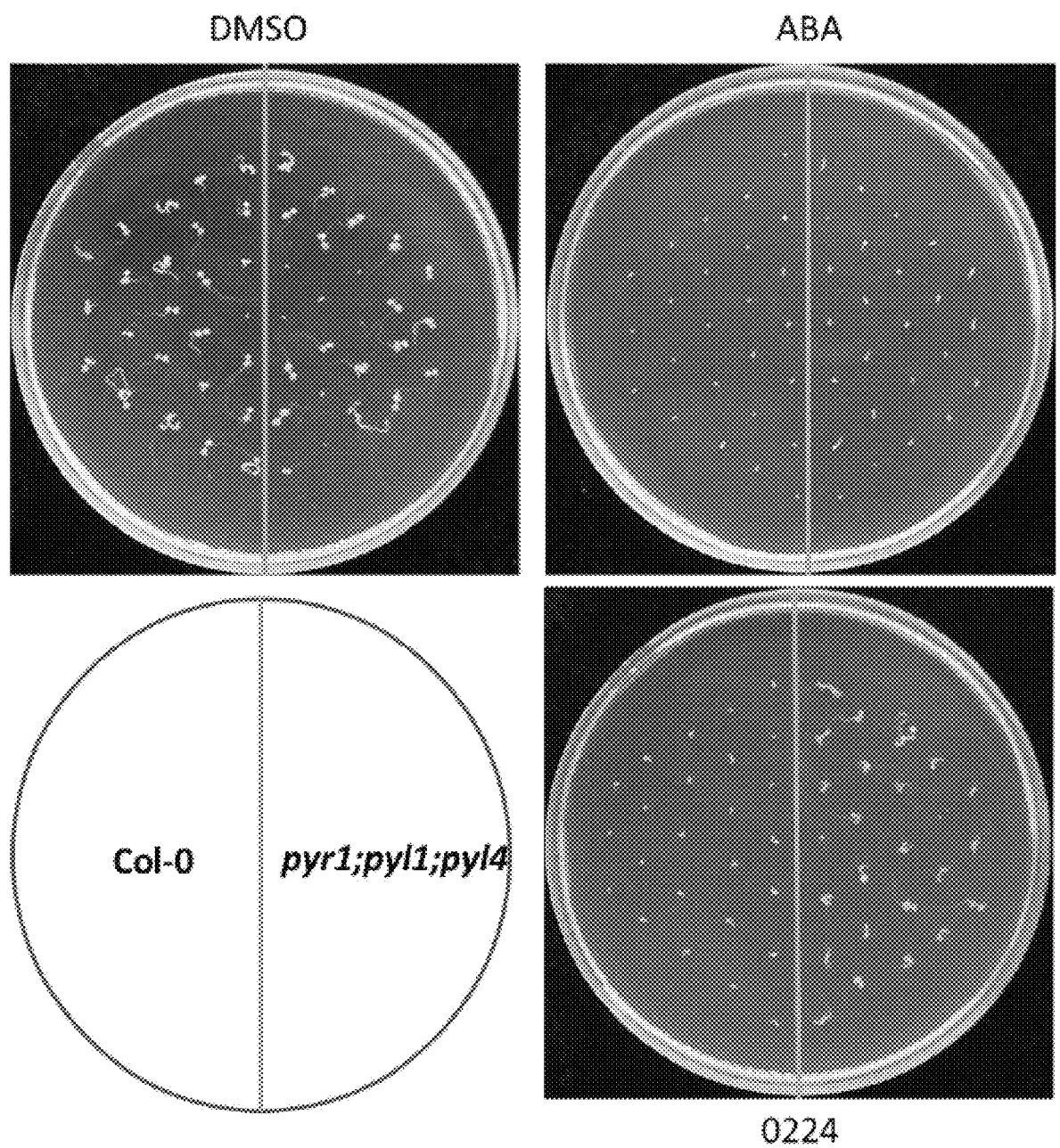
FIG. 3 shows the effects of compound 0224 and ABA on seed germination of Col-0 and pyr1;pyl1;pyl4 triple mutants at a concentration of 1 µM. Col-0 is sown on the left half and the pyr1;pyl1;pyl4 triple mutant is sown on the right half in each culture dish. 4 days after seed germination (6 days after sowing) of the pyr1;pyl1;pyl4 triple mutants, the photos are taken. DMSO treatment is a control group. The results show that the compound 0224 can inhibit the seed germination of Col-0, while the inhibitory effect on the seed germination of the pyr1;pyl1;pyl4 triple mutant is significantly reduced, indicating that the inhibition of compound 0224 on seed germination in *Arabidopsis thaliana* is mediated through ABA receptors, rather than toxic effects.

The results were shown in FIG. 3 and FIG. 15. Compounds 0224 and 0428 were taken as examples. 1 μM compound 0224 or 2 μM compound 0428 could inhibit the seed germination of Col-0 ecotype, but could not inhibit the seed germination of PYR/PYL triple mutant pyr1; pyl1; pyl4. The above results showed that the germination inhibitory effect of the compounds of the present invention (such as compounds 0224 and 0428) was due to activation of an intrinsic ABA signaling pathway in plant, rather than causing toxicity to the plant seed.

12.2 Inhibition of Leaf Transpiration in Arabidopsis, Soybean, Cotton and Wheat In this experiment, the temperature change of leaf surface was observed and recorded by an infrared camera, thus reflecting the strength of plant transpiration. The stronger the transpiration, the lower the leaf temperature.

Figure 4:
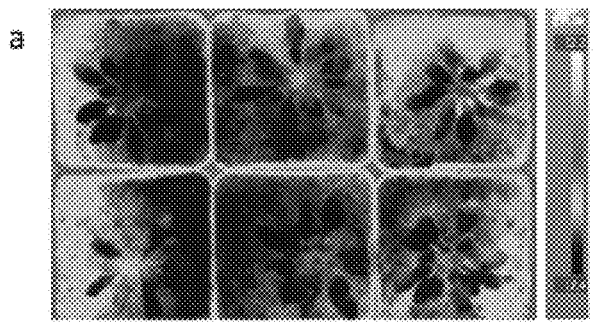
Figure 4:
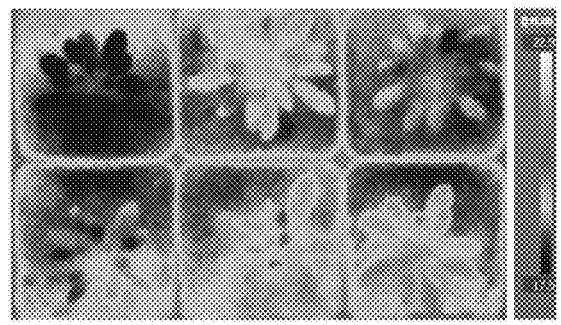
Figure 4:
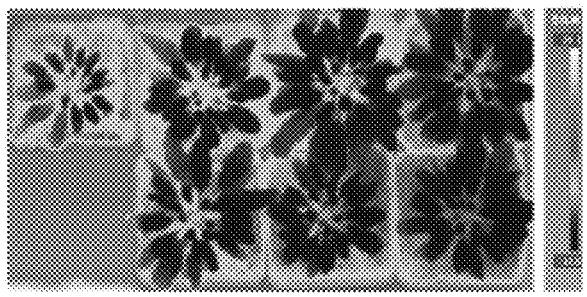
Figure 4:
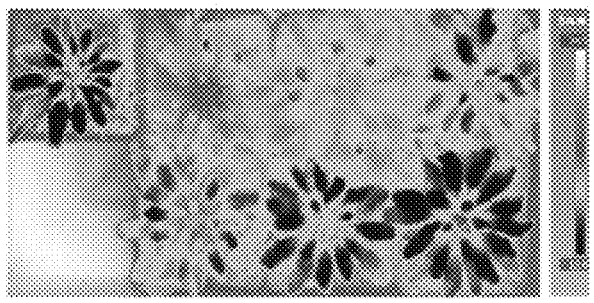
Figure 4:
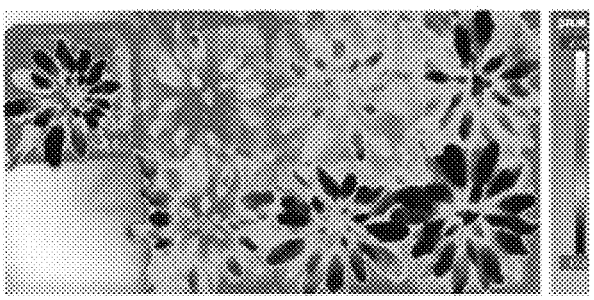
Figure 4:
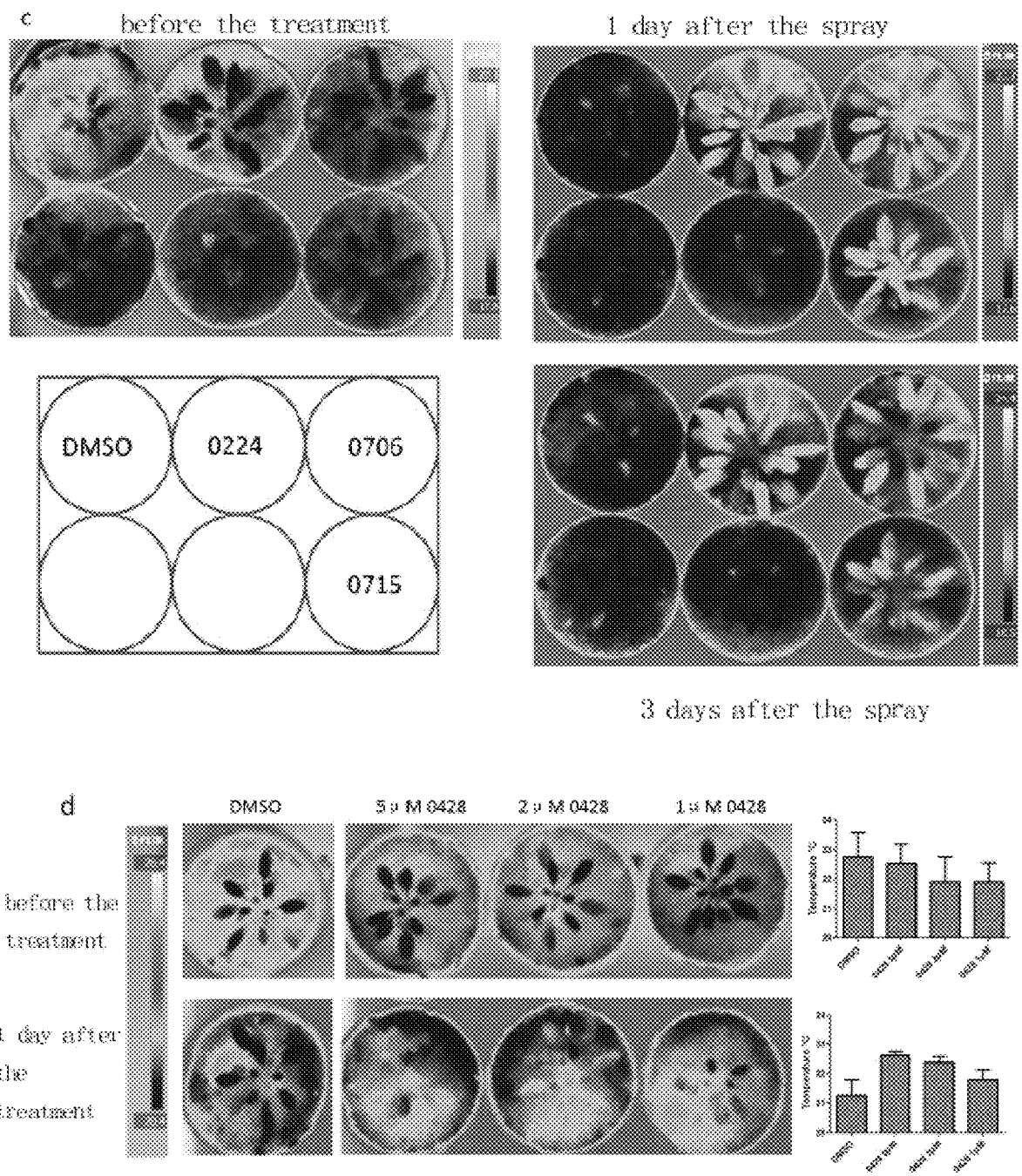

The results of Arabidopsis leaf transpiration experiment were shown in FIG. 4. After 5 μM ABA, compound 0224 (FIG. 4a) or compound 0304 (FIG. 4b) was sprayed on Arabidopsis aba2-1, the leaf temperature was higher than that in the DMSO control group, indicating that the compound-treated plants had a weaker transpiration. Four days after spraying, the leaf temperature of the plants sprayed with compound 0224 or 0304 was still significantly higher than that in the DMSO control, even after the concentration dropped to 2 μM or 1 μM, four days after spraying, the leaf temperature of the plants sprayed with the corresponding concentration of compound 0224 was still significantly higher than that in the DMSO control (FIG. 4b), while four days after spraying, leaf surface temperature of the plant sprayed with 5 μM ABA had dropped to the level before spraying. The above results showed that the inhibitory effect of compounds 0224 and 0304 on the leaf transpiration of Arabidopsis thaliana were better than that of ABA, and there was a dose-dependent effect on the inhibition of transpiration, wherein 0224 had a better effect. After Arabidopsis aba2-1 was sprayed with 5 μM compound 0706 or 0715, the leaf temperature was also significantly increased compared to the control (DMSO) treatment and the duration was equivalent to 0224 (FIG. 4c). On the other hand, the temperature of leaf treated with 5 μM/2 μM/1 μM 0428 compound for one day was also higher than that in the DMSO control group, indicating that the transpiration of the compound-treated plants was weakened, and meanwhile the compound 0428 had a dose-dependent effect on the inhibition on transpiration (FIG. 4d).

Figure 5:
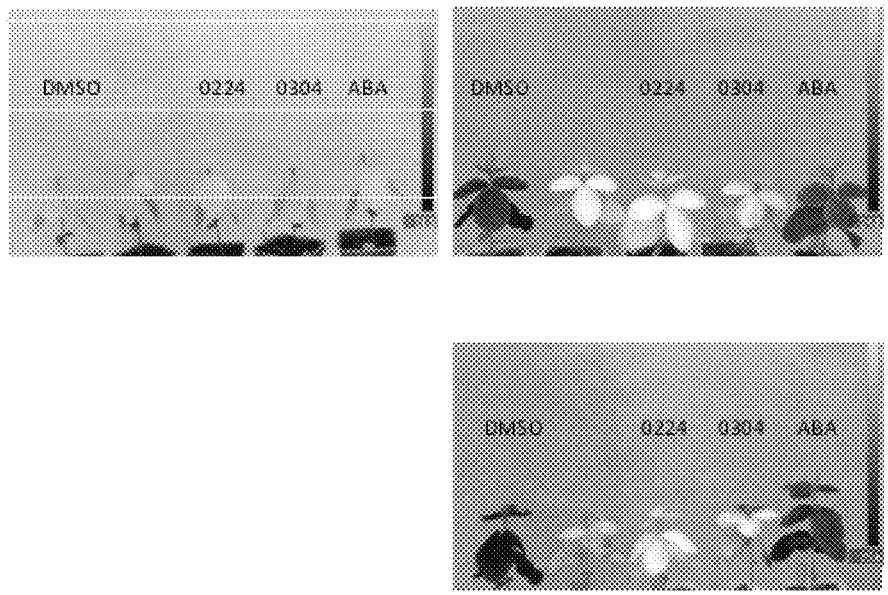
FIG. 5 shows that after treating with compounds 0224 and 0304 of the present invention, the transpiration rate of soybean leaf is significantly reduced, resulting in an increased leaf temperature. 14 days after sowing, the soybean plants are stopped watering and sprayed with compound 0224, or 0304 of the present invention or ABA. Compared with the control group (DMSO), 20 µM compound 0224 or 0304 can both significantly reduce the transpiration rate of soybean leaf, and the inhibitory effect is better than that of ABA at the same concentration.
Figure 6:
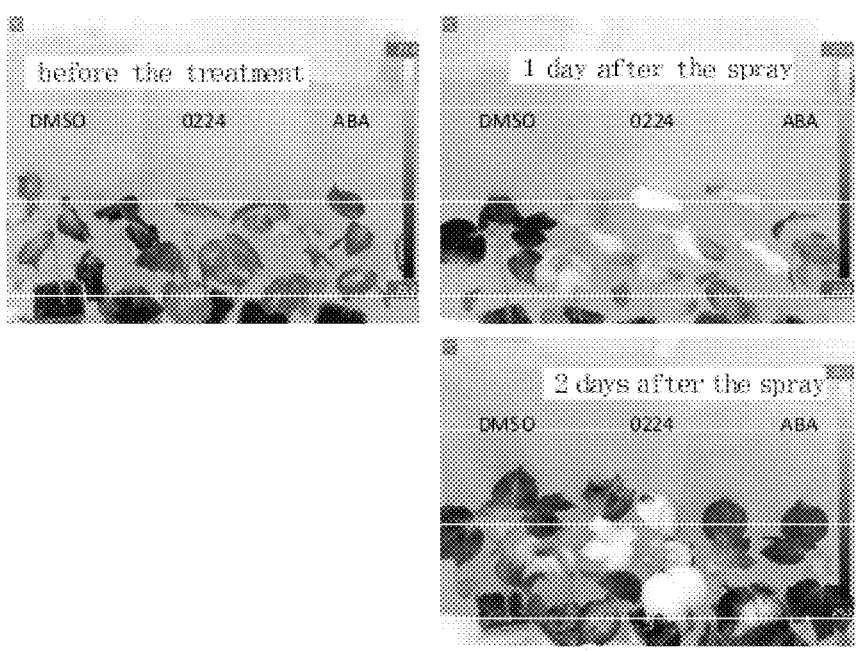
FIG. 6 shows that treatment with the compound 0224 of the present invention has significantly reduced the transpiration rate of the cotton leaf, resulting in an increased leaf temperature. 25 days after sowing, the cotton plants were stopped watering and sprayed with the compound 0224 of the present invention or ABA. Compared with the control group (DMSO), 20 µM compound 0224 can significantly reduce the transpiration rate of the cotton leaf, and the inhibitory effect is better than that of ABA at the same concentration.

The results of the leaf transpiration experiments in soybean, cotton, and wheat were shown in FIG. 5 and FIG. 6. The experiments on the inhibition of leaf transpiration in soybean showed that two days after spraying, for the plants sprayed with 20 μM of compound 0224 or 0304, the leaf temperature was still significant higher than that of plants in DMSO-sprayed control group, indicating that the transpiration of the soybean leaves was still inhibited at this time, whereas the leaf temperature of the plants sprayed with the same concentration of ABA had no difference from that in the control group (FIG. 5). The experiments on the inhibition of leaf transpiration in cotton showed that two days after spraying, for the plants sprayed with 20 μM of compound 0224, the leaf temperature was still significant higher than that of plants in DMSO-sprayed control group, whereas the leaf temperature of the plants sprayed with the same concentration of ABA had no difference from that in the control group (FIG. 6). The experiments on the inhibition of leaf transpiration in wheat showed that one day after spraying, for the plants sprayed with 100 μM of compound 0224 or ABA, the leaf temperature was still significant higher than that of plants in DMSO-sprayed control group, indicating that the transpiration of the wheat leaves was still inhibited at this time (FIG. 16). The results showed that compound 0224 can not only inhibit leaf transpiration in the dicot crops, such as soybean and cotton, but also can inhibit leaf transpiration in monocot crops, such as wheat. The above results showed that compounds 0224 and 0304 in soybean and compound 0224 in cotton and wheat also had the same effect of inhibiting leaf transpiration as that in *Arabidopsis thaliana*.

12.3 the Enhanced Drought-Resistance in *Arabidopsis*, Soybean, Cotton, Corn and Wheat

Figure 7:
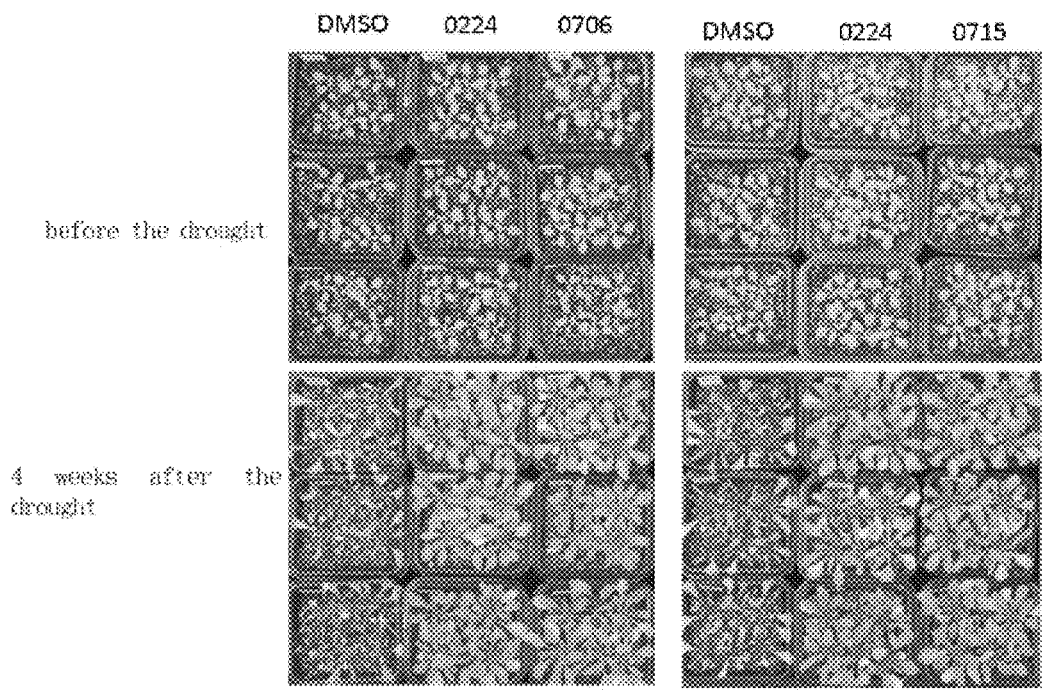
FIG. 7 shows the results of soil drought experiments on *Arabidopsis thaliana*. *Arabidopsis thaliana* is photographed before drought and four weeks after drought. The *Arabidopsis thaliana* in the control group (treated with DMSO) has withered four weeks after drought, while the *Arabidopsis* treated with compound 0224, 0706 or 0715 still grows normally.
Figure 12:
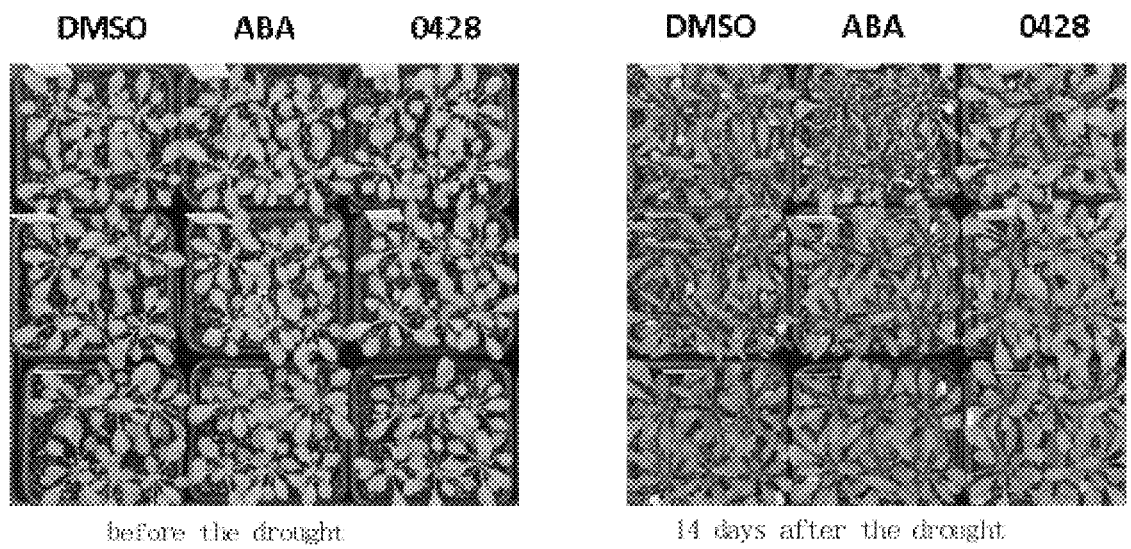
FIG. 12 shows the results of soil drought experiments on *Arabidopsis*. Wild-type *Arabidopsis* plants (Col-0) grown for 3 weeks in a short-day environment are stopped watering and sprayed with 5 µM ABA or the compound 0428 of the present invention. The growth condition of the plant on the day and 14 days after the first spraying of the compounds is shown in the figure, respectively. The plant sprayed with the DMSO solution is used as a negative control. The results show that the plant sprayed with compound 0428 exhibits a better growth condition than that in the control group and that sprayed with ABA.
Figure 13:
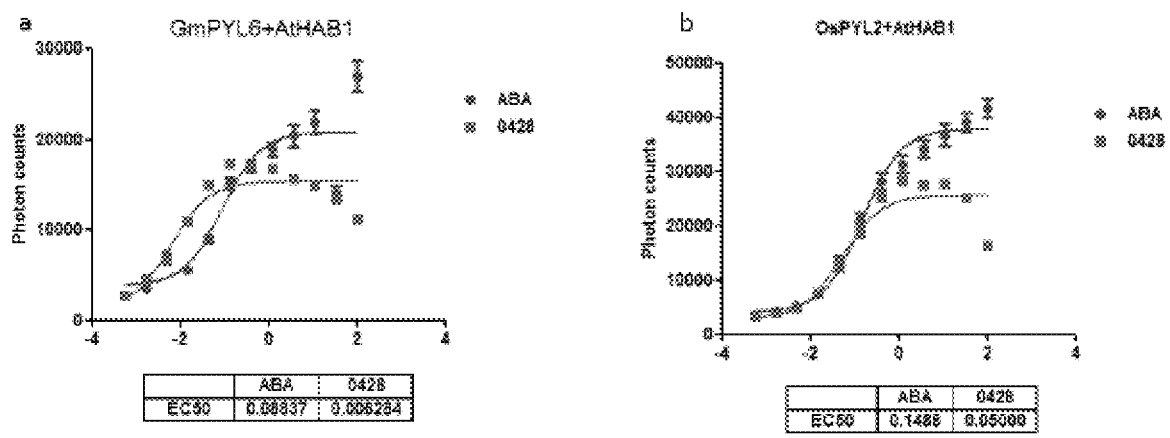
FIG. 13 shows a dose-response curve of soybean GmPYL6 and rice OsPYL2 receptor agonists of the compounds of the present invention (such as compound 0428)

*Arabidopsis thaliana* Col-0 ecotype that had been growing in the soil for two weeks was stopped watering, the leaf was sprayed with a solution containing 5 μM compound 0224/0706/0715 or 0.05% DMSO (control) once every week during the drought, with a spray amount of 2 ml solution/pot, twice in total and a 0.05% (v/v) surfactant Tween-20 was added to the solution to enhance the penetrating effect of the spray agent on the leaf epidermis. After four weeks of drought treatment, the DMSO-sprayed control group had all died of drought, while the plants sprayed with 5 μM compound 0224/0706/0715 still survived (FIG. 7). The same method was performed for drought treatment and (+)-ABA or 0428-treated *Arabidopsis* was photographed two weeks after the drought. As shown in FIG. 12, due to the low concentration, the growth of the plants sprayed with 5 μM (+)-ABA had no difference from that of plants in the DMSO-sprayed control group, whereas the growth of *Arabidopsis* sprayed with 5 μM 0428 was significantly better than that of plants in DMSO-sprayed control group and plants sprayed with 5 μM (+)-ABA.

Figure 8:
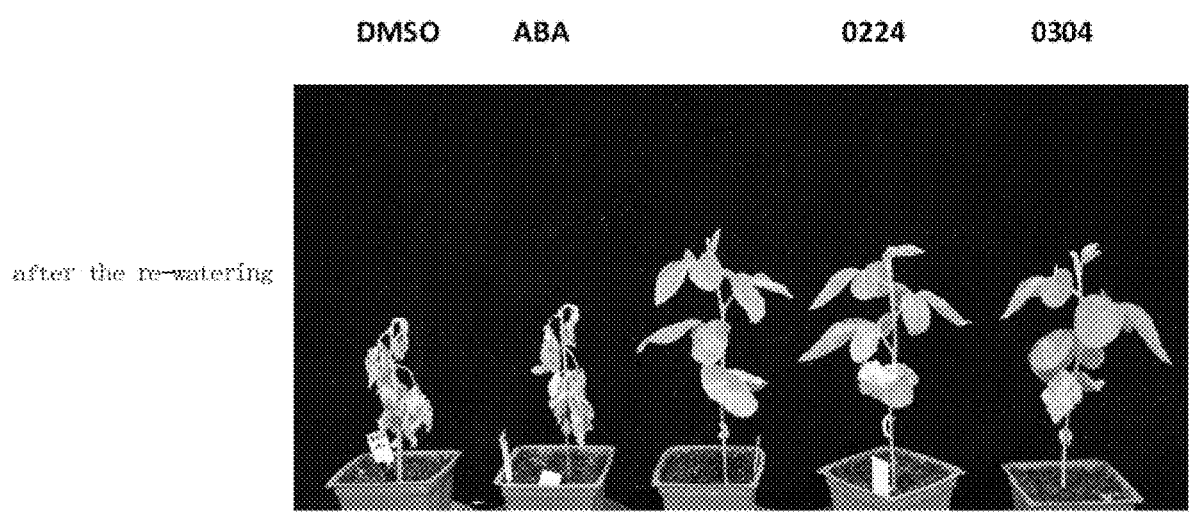
FIG. 8 shows the results of soil drought experiments on soybean. The soybean in FIG. 5 is re-watered after 6 days of drought. The photos show the growth condition of soybean one day after re-watering. The growth of the soybean treated with compound 0224 or 0304 is significantly better than that of the control group (DMSO) or that of the soybean treated with same concentration of ABA.
Figure 9:
FIG. 9 shows the results of soil drought experiments on cotton. The cotton in FIG. 6 is re-watered after 6 days of drought, and the compound 0224 of the present invention or ABA is sprayed once every 3 days during this period. The photos show the growth condition of cotton before re-watering and one day after re-watering. The growth of cotton treated with compound 0224 is significantly better than that of the control group (DMSO) or that of the cotton treated with the same concentration of ABA.
Figure 9:

Soybeans were sown for 14 days and cotton was sown for 25 days, respectively. Plants with the same size were selected for soil drought experiments. Soybeans were sprayed with an aqueous solution containing 20 μM of compound ABA/0224/0304 or 0.05% DMSO (control) once after the start of drought, whereas cotton was sprayed with an aqueous solution containing 20 μM of compound ABA/0224 or 0.05% once every 3 days after the start of drought. 0.1% (v/v) surfactant Tween-20 was added to the above solution to enhance the penetrating effect of the spray agent on the leaf epidermis. Re-watering after 6 days of the drought, soybeans sprayed with 20 μM compound 0224 or 0304 (FIG. 8) and cotton sprayed with 20 μM compound 0224 (FIG. 9) had significantly better growth after re-watering than that in the DMSO-sprayed control group and the plants sprayed with the same concentration of ABA.

In another group of experiments, soil drought experiments were performed on soybeans with three leaves in three groups or corn plants during the small trumpet period of the same size. After the start of the drought, an aqueous solution containing 50 μM compound 0428 or 0.05% DMSO (control) was sprayed once a day for two days, and 0.1% (v/v) surfactant Tween-20 was also added to the solution, Re-watering was performed after 4 days of the drought treatment for corn and after 9 days of the drought treatment for soybean, respectively, the soybeans (FIG. 14a) and corn (FIG. 14b) sprayed with 50 μM compound 0428 had significantly better growth after re-watering than that in the DMSO-sprayed control group.

In another group of experiments, wheat was sown for 16 days and plants of the same size were selected for soil drought experiments. Wheat was sprayed with an aqueous solution containing 100 μM of compound ABA/0224 or 0.1% DMSO (control) once every 3 days after the start of drought, and 0.1% (v/v) surfactant Tween-20 was added to the above solution to enhance the penetrating effect of the spray agent on the leaf epidermis. After 6 days of drought, the wheat in the control group was wilted, whereas the wheat treated with 100 μM of compound 0224 or ABA remained upright, and the growth was significantly better than that in the control group (DMSO) (FIG. 16).

The above results showed that the compounds of the present invention had a significant effect of enhancing drought resistance in both dicotyledonous and monocotyledonous plants.

Example 13 Compound 1022B could Induce the Expression of ABA-Responsive Stress-Related Gene The inventors analyzed the effect of exogenously added compound 1022B on the expression of plant genes.

Figure 10:
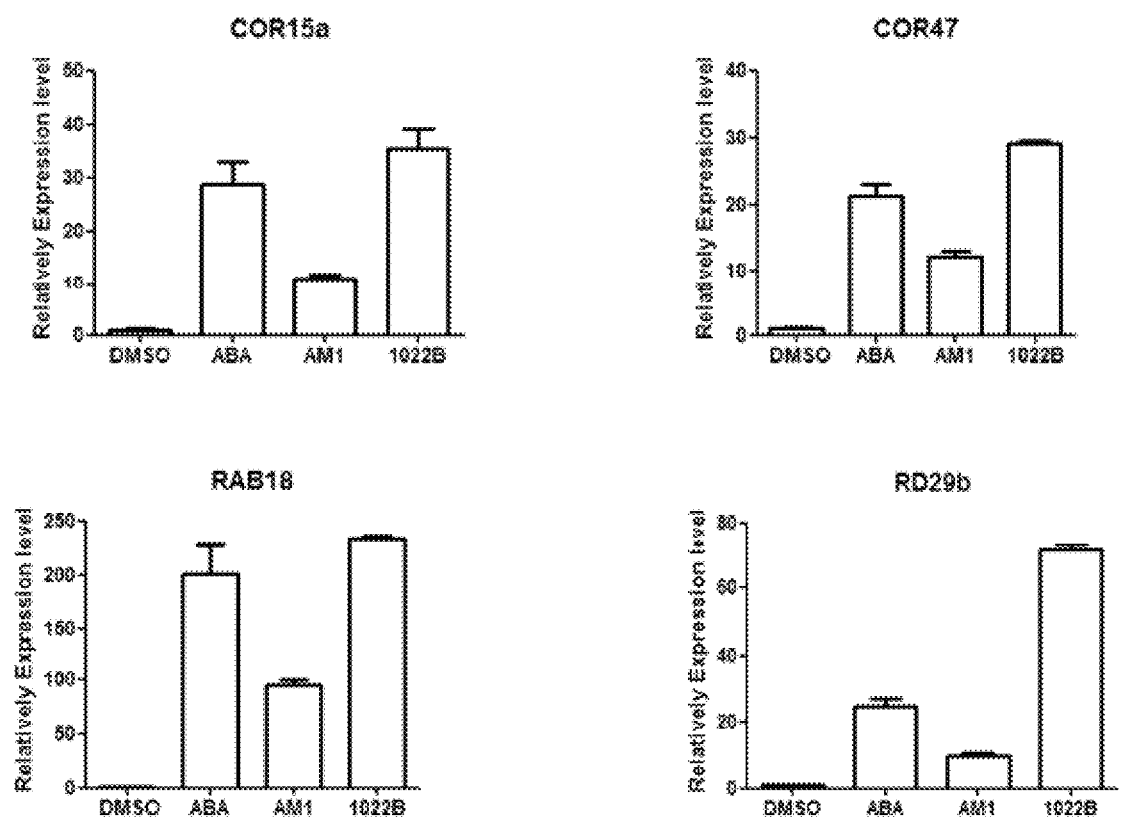
FIG. 10 shows a transcriptional change of stress-related genes induced by ABA in wild-type *Arabidopsis thaliana* after treating with 10 µM compound 1022B of the present invention for 6 hours. Treatment with DMSO and same concentration of ABA are used as negative and positive control group, respectively. The results show that the transcriptional levels of the four stress-related genes induced by the compound 1022B of the present invention are all higher than those of ABA.

The results of gene expression analysis showed that compound 1022B could induce the expression of ABA-responsive stress-related gene, and most of the expression levels were up to or higher than that induced by exogenous ABA at the same concentration (FIG. 10). Among 10-day-aged seedling plants of wild-type *Arabidopsis thaliana* (Col-0), the expression level of 4 known ABA-induced environmental stress-related gene (COR15a, COR47, RAB18 and RD29b) were significantly increased after treatment with 10 μM of 1022B compound, which significantly exceeded the level in the plants treated with 10 μM ABA at the same time.

The results showed that the induction effect of compound 1022B on most environmental stress-related genes was significantly better than that of ABA.

Example 14 Structure of PYL2-0428-HAB1 Complex

The crystal structure of PYL2-0428-HAB1 complex formed with 0428 compound of the present invention was examined using the protein crystal analysis method described in the general method. The resolution of the PYL2-0428-HAB1 complex crystal is 2.4 angstroms, and the control is ABA. The part sketches of two-dimensional structure of two complex crystals were shown in FIGS. 11a and 11b.

Figure 11A:
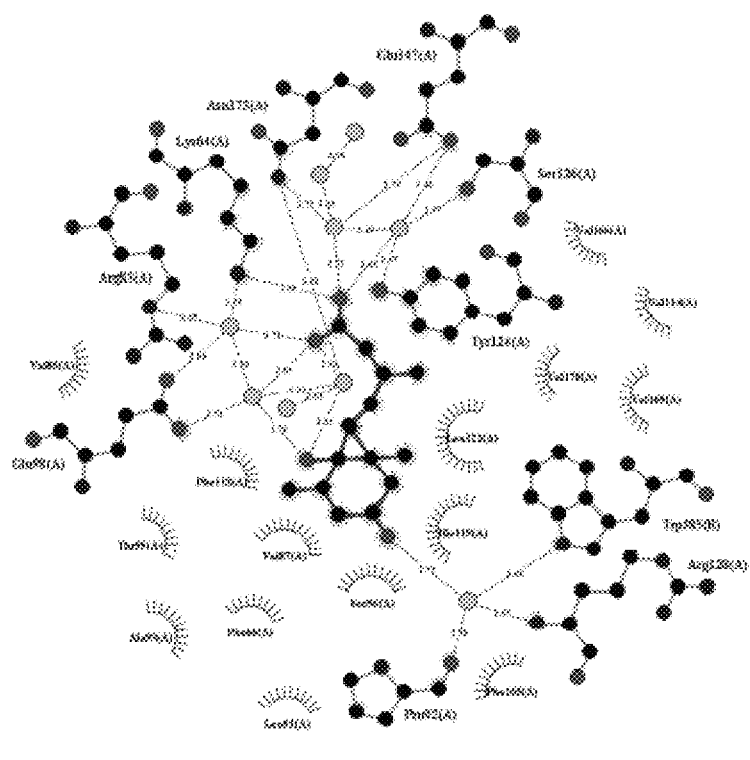
FIGS. 11a and 11b show a two-dimensional structure of the interaction between ABA (a), or the compounds of the present invention (0428) (b) and multiple amino acid residues within the pocket structure of PYL2-HAB1 complex, respectively. Water molecules, nitrogen atoms, oxygen atoms and halogen atoms are shown in the figure, the dotted lines represent hydrogen bonds, and the numbers indicate the distance between two atoms/molecules (the unit is Angstroms (Å)). The results show that, similar to ABA, the compound 0428 of the present invention form several hydrogen bonds with the amino acid residues within the PYL2 pocket structure, except that the formation of these hydrogen bonds does not require the mediation of water molecule, which allows a closer binding of compound 0428 to the PYL2-HAB1 complex.
Figure 11B:
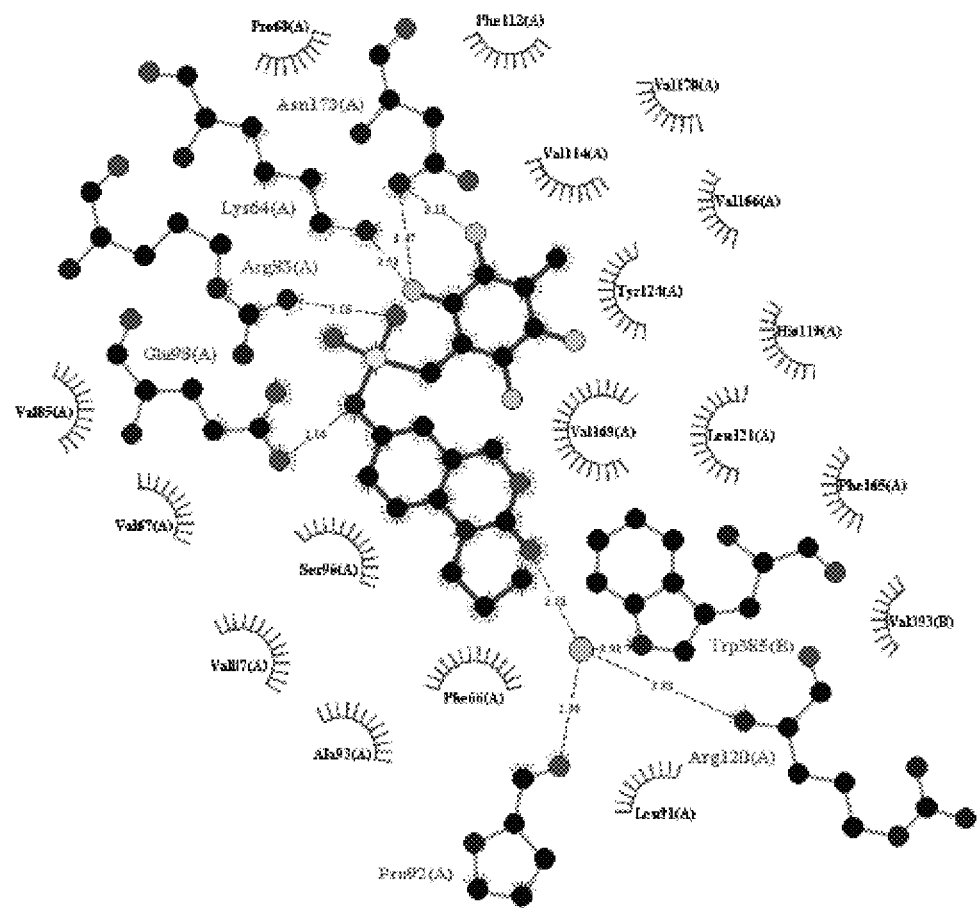

As seen from FIGS. 11a and 11b, 0428 was present in the pocket structure of PYL2, and four oxygen atoms on the ABA structure could form hydrogen bonds with multiple amino acid residues in the PYL2 pocket structure and HAB1 by means of several water molecules. The oxygen atoms and nitrogen atoms on the sulfonamide group of compound 0428 as well as oxygen atoms on the quinoline ring could also form hydrogen bonds. In addition, the halogen substituents (fluorine atom) on p-xylene also could form hydrogen bonds with amino acid residues in the PYL2 pocket structure for further enhancement of the affinity of compound 0428 to the PYL2 receptor.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A compound represented by formula (I), or a salt, or an optical isomer or a racemate, or a solvate, thereof,

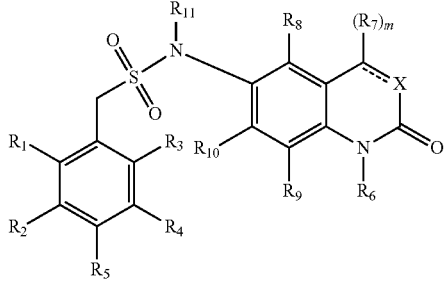

(I)

wherein,
$R_1$ is H, halogen, $C_1$-$C_3$ alkyl, or $C_1$-$C_3$ haloalkyl;
$R_2$ is H, halogen, $C_1$-$C_3$ alkyl, or $C_1$-$C_3$ haloalkyl;
$R_3$ is H, halogen, $C_1$-$C_3$ alkyl, or $C_1$-$C_3$ haloalkyl;
$R_4$ is H, halogen, $C_1$-$C_3$ alkyl, or $C_1$-$C_3$ haloalkyl;
$R_5$ is halogen, $C_1$-$C_3$ alkyl, $C_1$-$C_3$ haloalkyl, $SF_5$ or $C_3$-$C_8$ cycloalkyl;
$R_6$ is substituted or unsubstituted $C_1$-$C_7$ alkyl, substituted or unsubstituted $C_2$-$C_7$ alkenyl, substituted or unsubstituted $C_2$-$C_7$ alkynyl, substituted or unsubstituted $C_3$-$C_7$ cycloalkyl, or substituted or unsubstituted —$R_a$—O—$R_b$, wherein $R_a$ is $C_1$-$C_2$ alkylene and $R_b$ is H, $C_1$-$C_3$ alkyl; and substituted means substituted with one or more substituents selected from the group consisting of: halogen, —$OR_b$, —CN, —$N(R_b)_2$, and nitro;
$R_7$ is selected from the group consisting of: H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_5$-$C_{10}$ heterocyclyl, $R_c$—C(O)—, —$OR_b$, —CN, and —$N(R_b)_2$; $R_c$ is selected from the group consisting of: hydroxyl, mercapto, substituted or unsubstituted $C_1$-$C_6$ alkyl, substituted or unsubstituted $C_1$-$C_6$ alkoxy; wherein the heterocyclyl contains 1 to 2 heteroatoms selected from N, O, S, and substituted means substituted with one or more substituents selected from the group consisting of: halogen, —$OR_b$, —CN, —$N(R_b)_2$, and nitro;
$R_8$, $R_9$, $R_{10}$ are each independently selected from the group consisting of:
(i) H;
(ii) substituted or unsubstituted $C_1$-$C_6$ alkyl, $C_3$-$C_8$ alkoxy, substituted or unsubstituted $C_3$-$C_8$ cycloalkyl, halogen, $R_c$—C(O)—, —OH, —$NH_2$; $R_{11}$ is selected from the group consisting of: hydroxyl, mercapto, substituted or unsubstituted $C_1$-$C_6$ alkyl, substituted or unsubstituted $C_1$-$C_6$ alkoxy; wherein substituted means substituted with one or more substituents selected from the group consisting of: halogen, —$OR_b$, —CN, —$N(R_b)_2$, and nitro;
$R_{11}$ is H, $C_1$-$C_3$ alkyl, or $C_1$-$C_3$ haloalkyl;
X is $NR_{13}$, O, or S, $R_{13}$ is none, or selected from the group consisting of: H, halogen, $C_1$-$C_3$ alkyl, $C_2$-$C_3$ alkenyl, $C_2$-$C_3$ alkenyl, and $C_1$-$C_3$ haloalkyl;
m=1 or 2;
"═" represents a single bond or a double bond.

2. The compound of claim 1, wherein the compound has a structure of formula Ia:

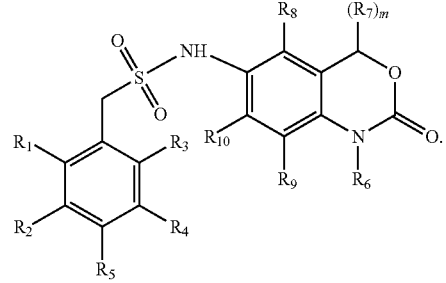

Ia

3. The compound of claim 1, wherein the compound has a structure of formula Ib:

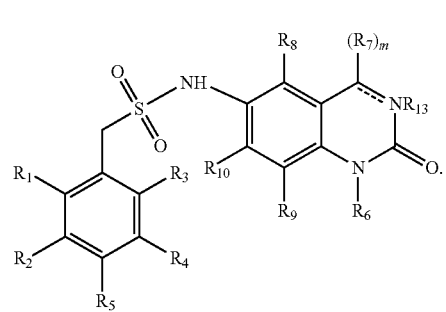

Ib

4. The compound of claim 1, wherein the compound has a structure of formula Ic:

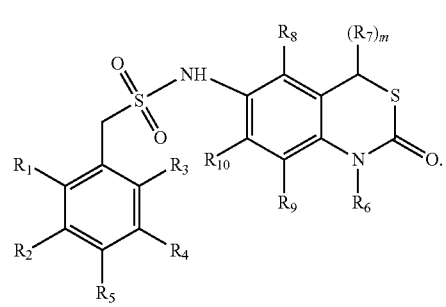

Ic

5. The compound of claim 1, wherein the compound is selected from the group consisting of:

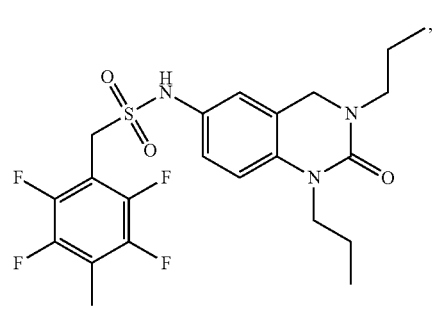

NC3F4

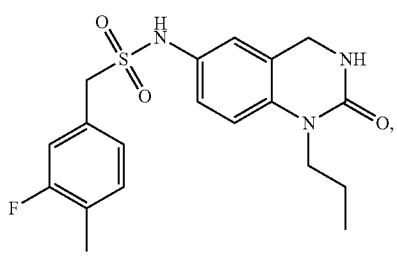 NC0FD1
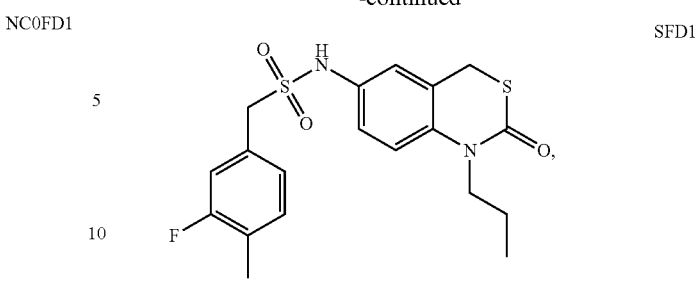 SFD1
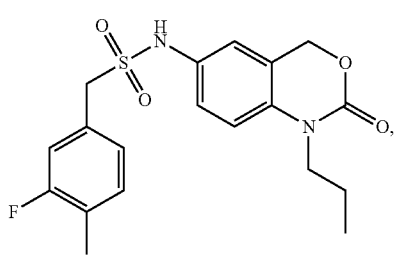 OFD1
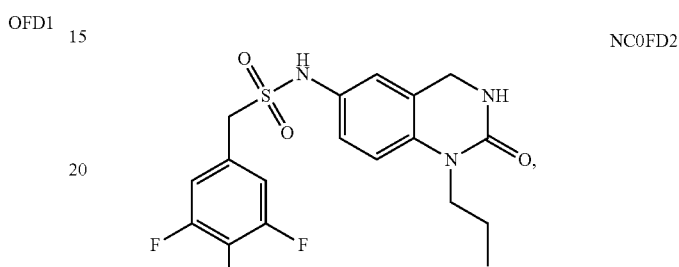 NC0FD2
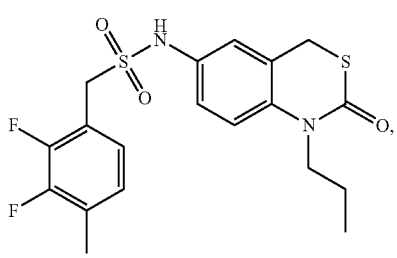 SFS2
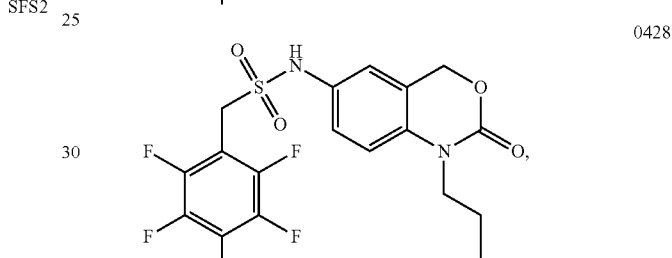 0428
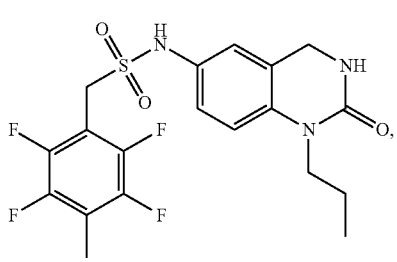 NC0F4
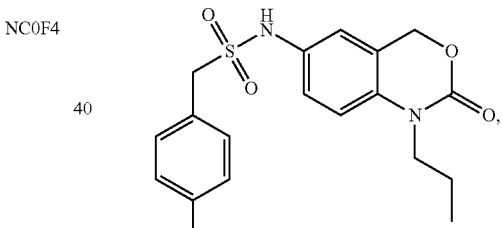 OF0
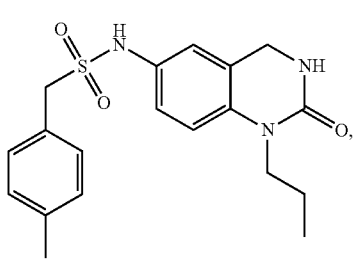 NC0F0
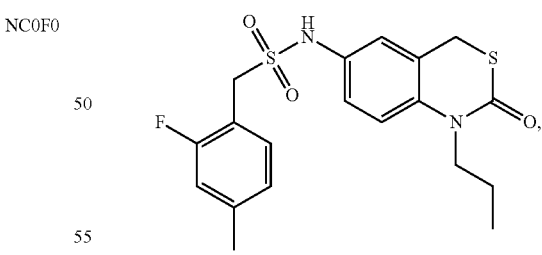 SFU1
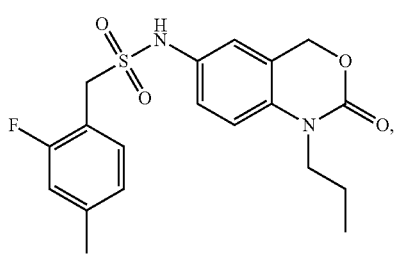 OFU1
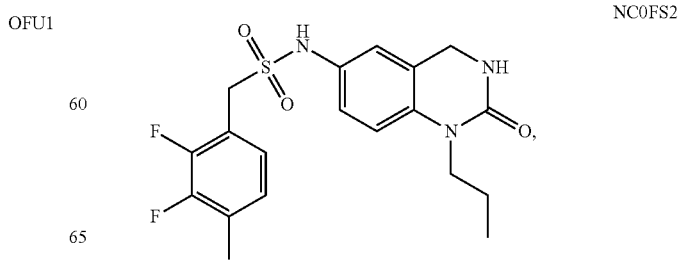 NC0FS2

OFS2
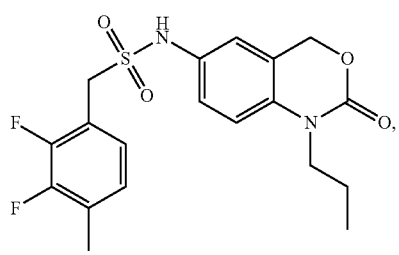
SF4
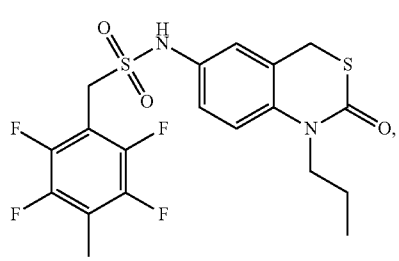
SF0
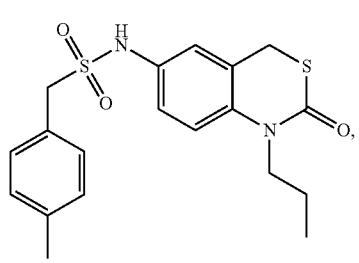
NC0FU1
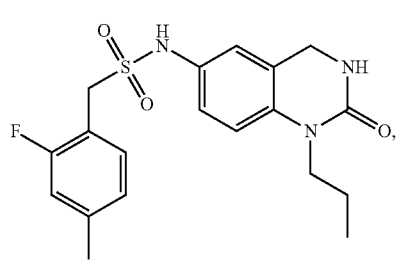
OFD2
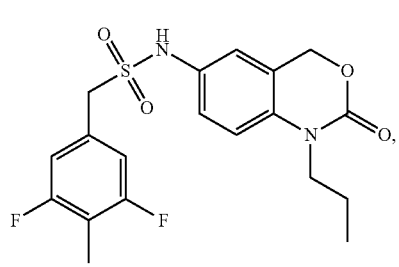
SFD2
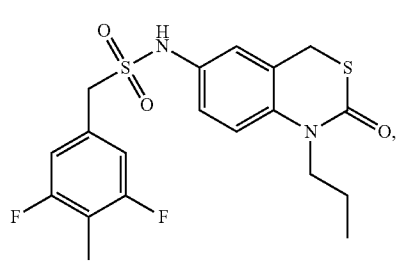
NDFUF1
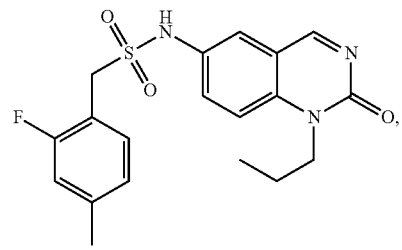
NDFDF1
NDF0
NDF4
NDFD2
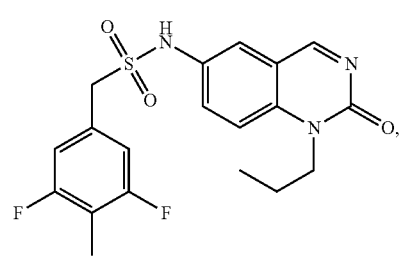
NDFS2
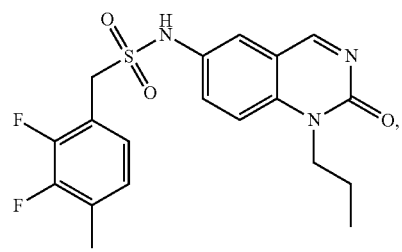

1-3 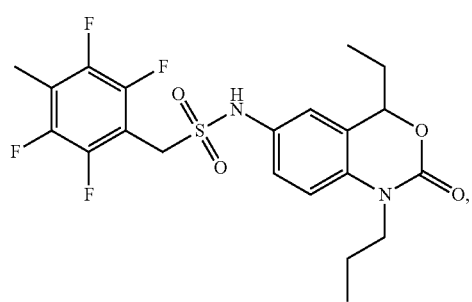
1-4 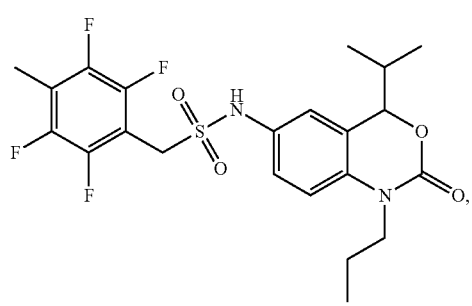
1-5 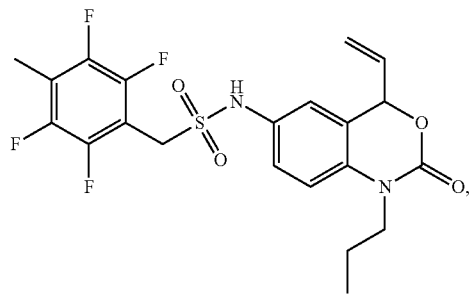
1-6 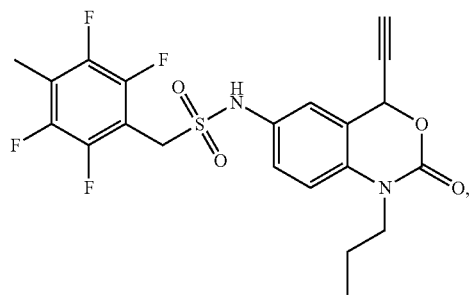
2-1 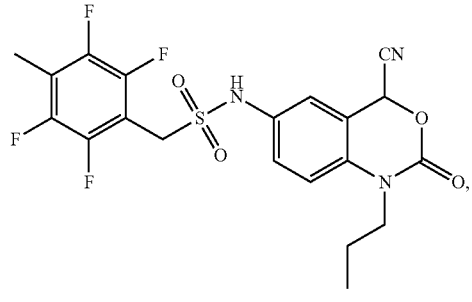
2-2 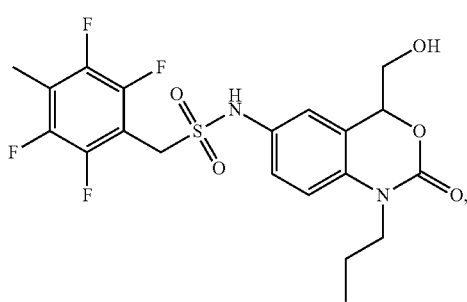
2-3 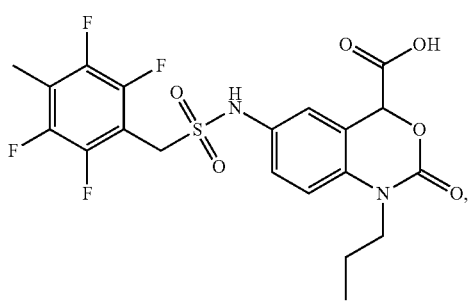
2-4 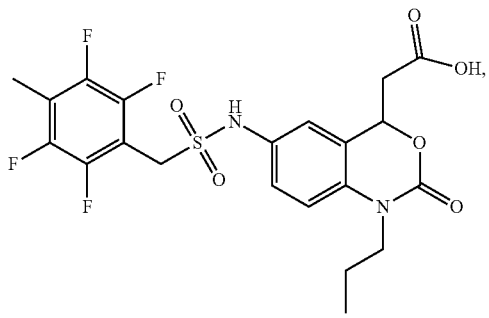
3-1 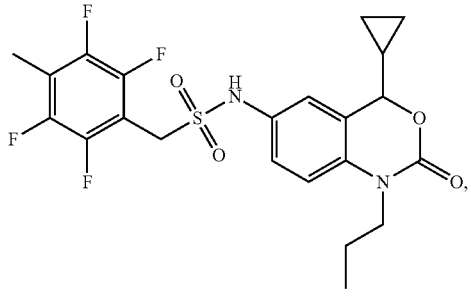
3-2 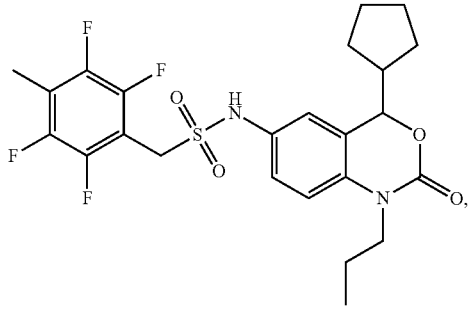

3-3
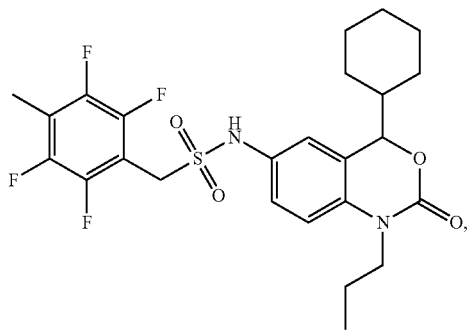
3-4
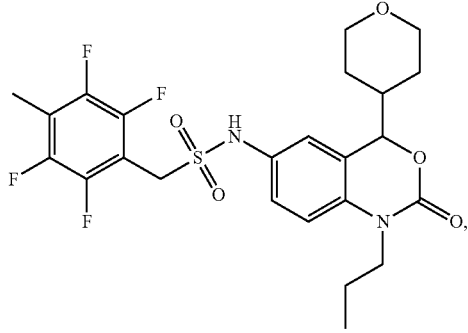
4-OH
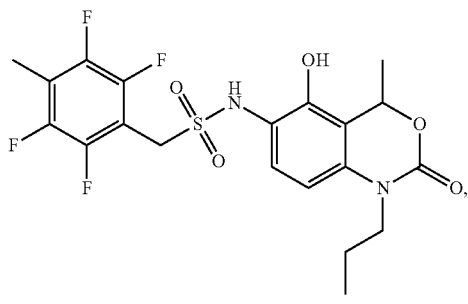
4-F
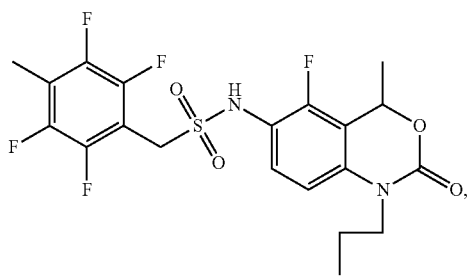
4-NH2
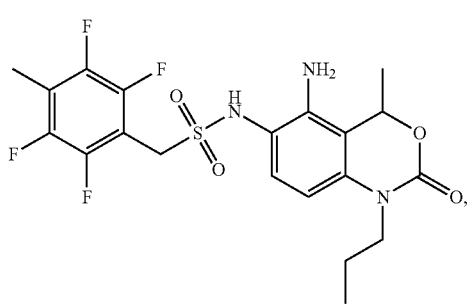
4-CH3
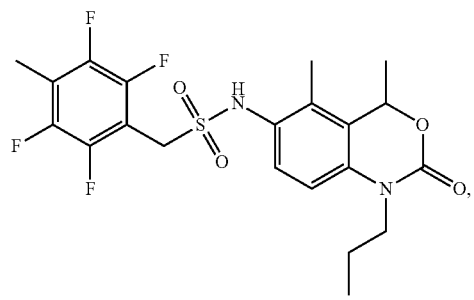
4-COOH
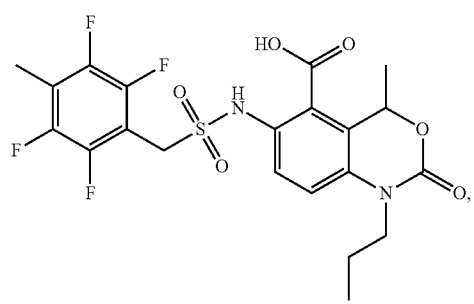
4-CH2OH
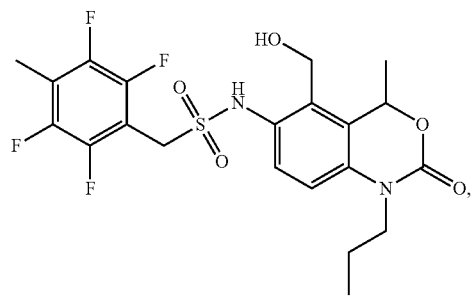
5-OH
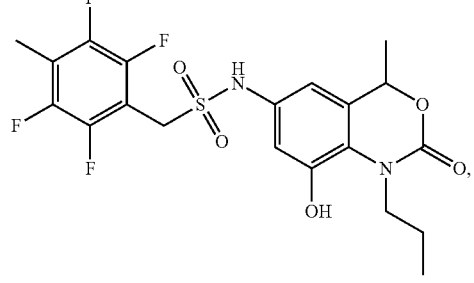
5-CH3
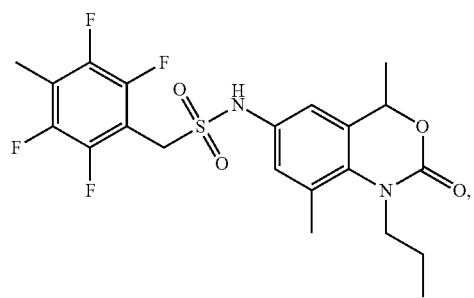

77
-continued
5-NH2
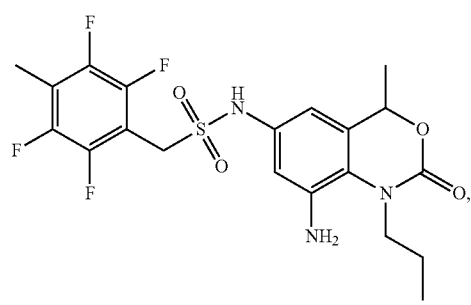
5-F
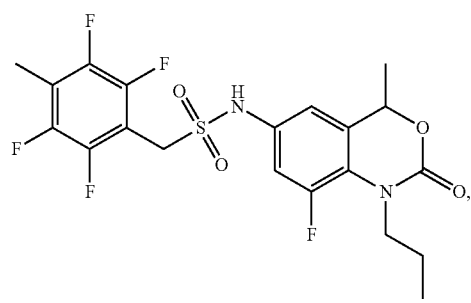
5-COOH
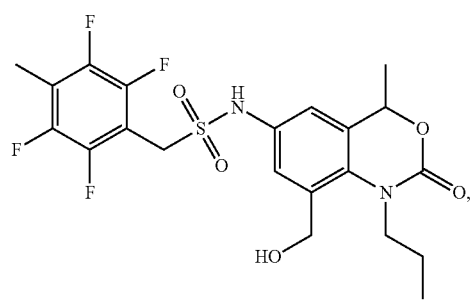
5-CH2OH
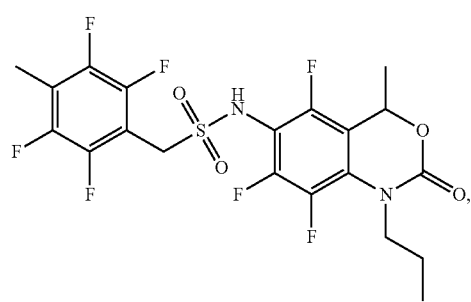
6-ALLF
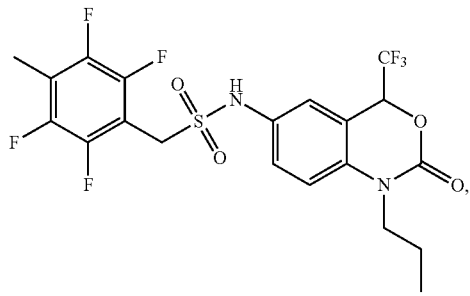
78
-continued
7-CF3
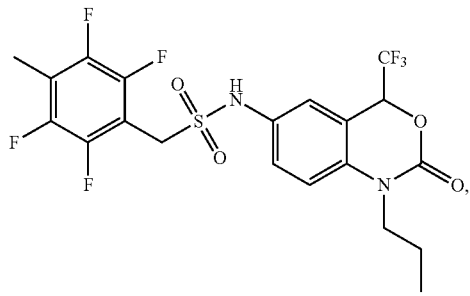
7-CF3
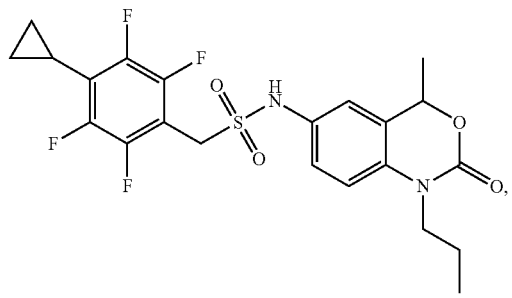
8-Tri-H
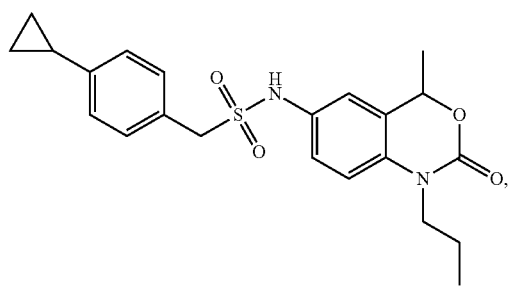
8-Tri-F
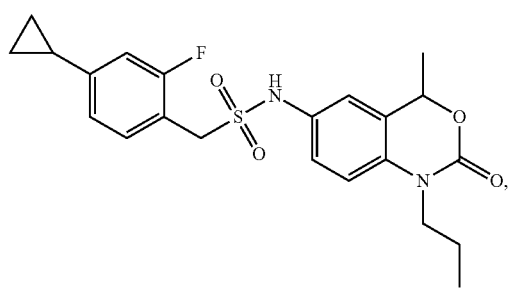
8-Tri-Fd
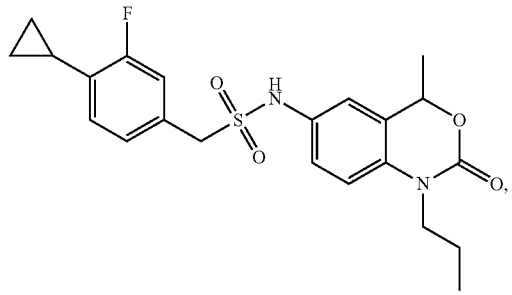

8-Tris-2F
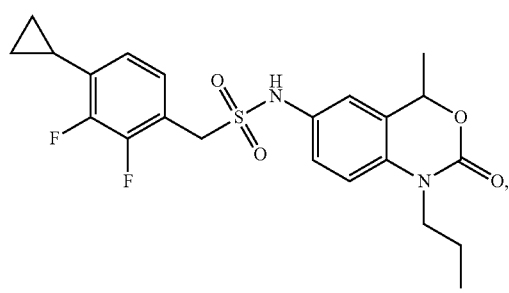
8-Tris-2Fd
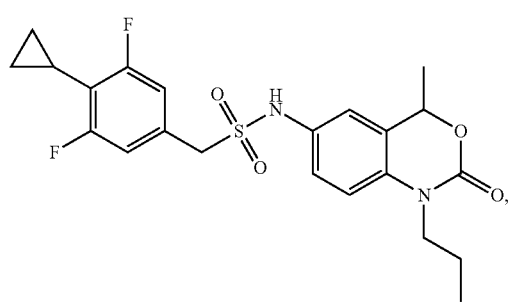
0224
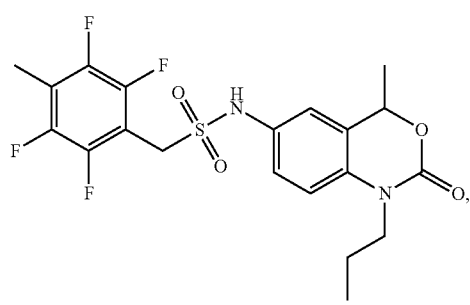
0304
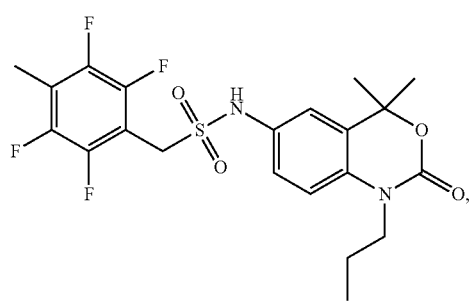
0706
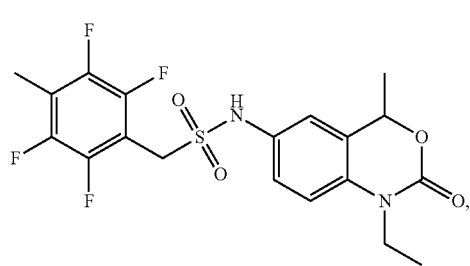
0708
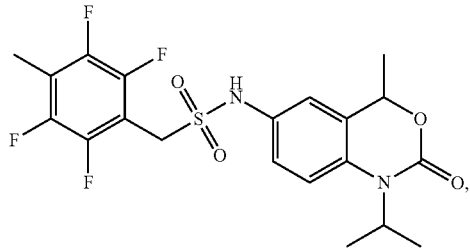
0713
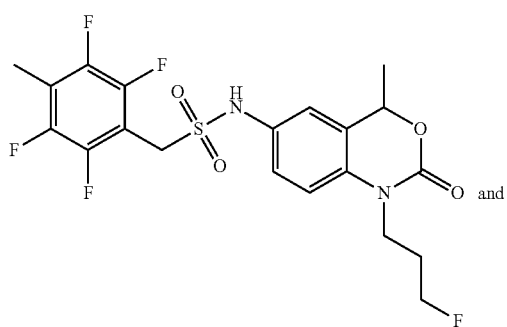
0715
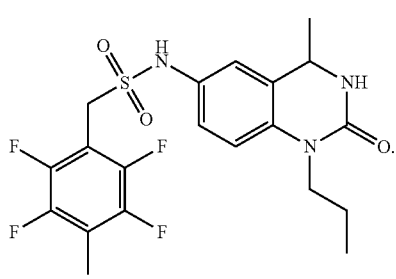 and
1028c
6. An agricultural formulation which comprises:
   (i) a compound represented by formula (I), or a salt, or an optical isomer, or a racemate, or a solvate thereof of claim 1; and
   (ii) an agriculturally acceptable carrier.
7. The compound represented by formula (I) of claim 1, wherein the compound is selected from the group consisting of:

[0224]
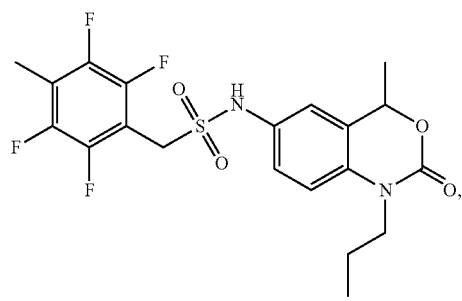
[0304]
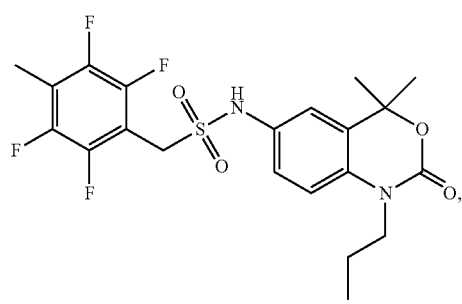
[0706]
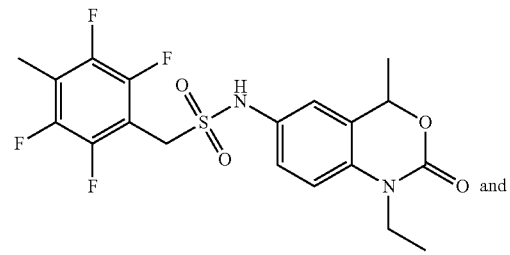
and
[0715]
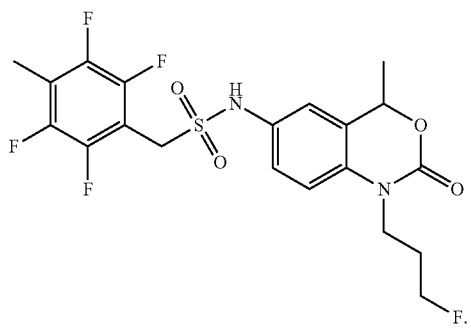
* * * * *